United States Patent
Berka et al.

(10) Patent No.: US 11,725,307 B2
(45) Date of Patent: Aug. 15, 2023

(54) IMMUNO-PETE

(71) Applicant: Roche Sequencing Solutions, Inc., Pleasanton, CA (US)

(72) Inventors: Jan Berka, Pleasanton, CA (US); Brian Godwin, Livermore, CA (US); Carolina Dallett, Oakland, CA (US); Sedide Ozturk, Pleasanton, CA (US); Joseph Platzer, Oakland, CA (US); Seoyoung Kim, Foster City, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 270 days.

(21) Appl. No.: 17/307,912

(22) Filed: May 4, 2021

(65) Prior Publication Data

US 2021/0254157 A1    Aug. 19, 2021

Related U.S. Application Data

(63) Continuation of application No. 15/611,507, filed on Jun. 1, 2017, now Pat. No. 11,098,360.

(60) Provisional application No. 62/344,330, filed on Jun. 1, 2016.

(51) Int. Cl.
| | |
|---|---|
| *C40B 50/06* | (2006.01) |
| *C12Q 1/68* | (2018.01) |
| *C12Q 1/6881* | (2018.01) |
| *C12N 15/10* | (2006.01) |
| *C12Q 1/6886* | (2018.01) |

(52) U.S. Cl.
CPC .......... *C40B 50/06* (2013.01); *C12N 15/1065* (2013.01); *C12Q 1/68* (2013.01); *C12Q 1/6881* (2013.01); *C12Q 1/6886* (2013.01); *C12Q 2600/16* (2013.01)

(58) Field of Classification Search
None
See application file for complete search history.

(56) References Cited

U.S. PATENT DOCUMENTS

| | | |
|---|---|---|
| 5,624,825 A | 4/1997 | Walker et al. |
| 8,932,831 B2 | 1/2015 | Korfhage et al. |
| 9,315,863 B2 | 4/2016 | Nadeau |
| 9,546,399 B2 | 1/2017 | Amorese et al. |
| 10,590,471 B2 | 3/2020 | Godwin |
| 2005/0123956 A1 | 6/2005 | Blume et al. |
| 2005/0266439 A1 | 12/2005 | Hjorleifsdottir |
| 2007/0020640 A1 | 1/2007 | McCloskey et al. |
| 2008/0102470 A1 | 5/2008 | Dawson et al. |
| 2010/0330571 A1 | 12/2010 | Robins |
| 2012/0077684 A1 | 3/2012 | O'Hara et al. |

(Continued)

FOREIGN PATENT DOCUMENTS

| | | |
|---|---|---|
| EP | 0684315 A1 | 11/1995 |
| EP | 0672173 B1 | 8/2002 |

(Continued)

OTHER PUBLICATIONS

European Partial Search Report in PCT/US2017/035516 dated Sep. 4, 2017; 14 pages.

(Continued)

*Primary Examiner* — Christian C Boesen
(74) *Attorney, Agent, or Firm* — Kilpatrick Townsend and Stockton LLP

(57) ABSTRACT

Methods and compositions are described herein for primer extension target enrichment of immune receptor (BCR or TCR) sequences.

10 Claims, 7 Drawing Sheets

Specification includes a Sequence Listing.

(56) References Cited

U.S. PATENT DOCUMENTS

| | | |
|---|---|---|
| 2012/0289414 A1 | 11/2012 | Mitra et al. |
| 2013/0231253 A1 | 9/2013 | Amorese et al. |
| 2013/0303461 A1 | 11/2013 | Iafrate et al. |
| 2014/0193860 A1 | 7/2014 | Bevilacqua |
| 2015/0119261 A1 | 4/2015 | Richard |
| 2015/0211050 A1 | 7/2015 | Lafrate et al. |
| 2016/0024493 A1 | 1/2016 | Robins |
| 2016/0138011 A1 | 5/2016 | DeWitt et al. |
| 2016/0203259 A1 | 7/2016 | Scolnick et al. |
| 2016/0222427 A1 | 8/2016 | So et al. |
| 2017/0016056 A1 | 1/2017 | Tan et al. |
| 2017/0159040 A1 | 6/2017 | Lock et al. |

FOREIGN PATENT DOCUMENTS

| | | |
|---|---|---|
| WO | 2009148560 A2 | 12/2009 |
| WO | 2012/027503 A2 | 3/2012 |
| WO | 2012/027503 A3 | 3/2012 |
| WO | 2012/048340 A2 | 4/2012 |
| WO | 2012048341 A1 | 4/2012 |
| WO | 2013/086450 A1 | 6/2013 |
| WO | 2013169339 A1 | 11/2013 |
| WO | 2013181170 A1 | 12/2013 |
| WO | 2014/145992 A1 | 9/2014 |
| WO | 2016118719 A1 | 7/2016 |
| WO | 2016149837 A1 | 9/2016 |
| WO | 2017021449 A1 | 2/2017 |

OTHER PUBLICATIONS

Feuchtenberger, M. et al.; "Semiquantitative and qualitative assessment of B-lymphocyte VH repertoire by a fluorescent multiplex PCR"; Journal of Immunological Meth.; vol. 276, No. 1-2; May 1, 2003; pp. 121-127.
Pasqual, N. et al.; "Quantitative and qualitative changes in V-J alpha rearrangements during mouse thymocytes differentiation: implication for a limited T cell receptor alpha chain repertoire"; The Journal of Experimental Medicine; Rockefeller University Press, US; vol. 196, No. 9; Nov. 4, 2002; pp. 1163-1173.
Ritgen, M. et al.; "Unmutated immunoglobulin variable heavy-chain gene status remains an adverse prognostic factor after autologous stem cell transplantation for chronic lymphocytic leukemia"; Blood; vol. 101, No. 5; Oct. 31, 2002; pp. 2049-2053.
International Search Report in PCT/US2017/035516 dated Feb. 9, 2018; 21 pages.
Robins, H. et al.; "Comprehensive assessment of T-cell receptor beta-chain diversity in alpha beta T cells"; Blood; vol. 114, No. 19; Nov. 5, 2009; pp. 4099-4107.
Campbell, et al.; "Locked vs. unlocked nucleic acids (LNA vs. UNA): contrasting structures work towards common therapeutic goals"; Chem. Soc. Rev.; vol. 40; 2011; pp. 5680-5689.
Jabara, CB et al.; "Accurate sampling and deep sequencing of the HIV-1 protease gene using a Primer ID"; Proc. Natl. Acad. Sci. USA; vol. 108, No. 50; Dec. 13, 2011; pp. 20166-20171; Epub Nov. 30, 2011.
Jabara, et al.; "Supplemental Information"; PNAS; vol. 108, No. 50; pp. 20166-20171; 2011.
Meyer, et al.; "A high-coverage genome sequence from an archaic Denisovan individual"; Science; vol. 338, No. 6104; Oct. 12, 2012; pp. 222-226; Epub Aug. 30, 2012.
Meyer, et al.; "Supplemental Information"; Science; vol. 338, No. 6104; pp. 222-226; 2012.
Croucher, NJ et al.; "A simple method for directional transcriptome sequencing using Illumina technology"; Nucleic Acids Res.; vol. 37, No. 22; Dec. 2009; pp. 3148.
Ganova-Raeva, L. et al.; "Primer Extension Enrichment Reaction (PEER): a new subtraction method for identification of genetic differences between biological specimens"; Nuc. Acid Res.; vol. 34, Issue 11; 2006; pp. 376.
Ganova-Raeva, L.M.; "Nucleic Acids Hybridization: modern applications, Primer Extension Enrichment Reaction (Peer) and other Methods for Difference Screening"; Springer; vol. 34, Issue 11; 2007; pp. 125-165.
International Search Report and Written Opinion dated Feb. 14, 2019 in PCT/EP2018/085727; pp. 1-14.
International Search Report and Written Opinion dated Jul. 22, 2015 in PCT/EP2015/052723.
Gupta et al.; "Synthesis and surface engineering of iron oxide nanoparticles for biomedical applications"; Biomaterials; vol. 26; 2005; pp. 3995-4021.
Kim et al.; "Multifunctional Uniform Nanoparticles Composed of a Magnetite Nanocrystal Core and a Mesoporous Silica Shell for Magnetic Resonance and Fluorescence Imaging and for Drug Delivery"; Angewandte Chemie International Edition; vol. 46; 2008; pp. 6438-6441.
Liu, et al.; "Shape Evolution and Tunable Properties of Monodisperse Magnetite Crystals Synthesized by a Facile Surfactant-Free Hydrothermal Method"; European Journal of Inorganic Chemistry; 2010; pp. 4499-4505.
Narayanan et al.; "Enhanced Bio-Compatibility of Ferrofluids of Self-Assembled Superparamagnetic Iron Oxide-Silica core-Shell Nanoparticles"; Journal of Nanoscience and Nanotechnology; vol. 11; 2011; pp. 1958-1967.
Alon, S. et al.; "Barcoding bias in high-throughput multiplex sequencing of miRNA"; Genome Research; 2011; pp. 1506-1511.
Fu, GK et al.; "Molecular indexing enables quantitative targeted RNA sequencing and reveals poor efficiencies in standard library preparations"; PNAS; vol. 111, No. 5; 2014; pp. 1891-1896.
Hashimshony, T. et al.; "CEL-Seq: Single-Cell RNA-Seq by Multiplexed Linear Amplification"; Cell Reports; vol. 2, No. 3; Sep. 27, 2012; pp. 666-673; Epub Aug. 30, 2012.
Hashimshony, T.; "CEL-Seq Protocol, Supplemental Information Document"; 2012; pp. 1-9.
Head, S.R. et al.; "Library construction for next-generation sequencing: Overviews and Challenges"; BioTechniques; vol. 56; 2014; pp. 61-77.
Heger, M.; "Roche Acquires AbVitro's Sample Prep Tech to Integrate with Genia and PacBio Systems"; genomeweb; 2014; pp. 1-2.
Islam, S. et al.; "Highly multiplexed and strand-specific single-cell RNA 5' end sequencing"; Nature Protocol; vol. 7, No. 5; 2012; pp. 813-828.

IMMUNO-PETE

CROSS-REFERENCE TO RELATED PATENT APPLICATIONS

This application is a continuation of U.S. patent application Ser. No. 15/611,507, filed Jun. 1, 2017, which claims benefit of priority to U.S. Provisional Patent Application No. 62/344,330, filed on Jun. 1, 2016, both of which are incorporated by reference for all purposes.

REFERENCE TO A SEQUENCE LISTING

The Sequence Listing written in file Sequence_Listing_098599-1247330-P33638US4.txt created on May 3, 2021, 77,384 bytes, machine format IBM-PC, MS-Windows operating system, is hereby incorporated by reference in its entirety for all purposes.

BACKGROUND OF THE INVENTION

The adaptive immune system can generate a wide array of diverse binding molecules. For example, recombination, random insertion, deletion and substitution, has the potential to create between $10^{15}$ and $10^{20}$ T-cell receptor (TCR) clonotypes and considerably more B cell receptor (BCR) clonotypes due to the greater number of VDJ sequences as well as somatic hypermutation. Naïve B or T cell clonotypes can be subject to positive and negative selection pressures, where cells expressing certain immune receptor sequences are expanded or deleted respectively. As such, the repertoire of BCR or TCR sequences can include information regarding immunological development, diseases state, the status of an organ transplant (e.g., tolerated or rejected), or the presence or absence of an autoimmune disorder, cancer, or infection. Moreover, high throughput sequencing of BCR or TCR repertoires has become a powerful tool to study or monitor basic immunology, disease state, autoimmune disorders, cancer, infection, organ transplantation and the like.

BRIEF SUMMARY OF THE INVENTION

Described herein are improved methods and compositions for primer extension target enrichment (PETE) of immune receptor (TCR or BCR, or a combination thereof) sequences. Methods and compositions described herein can be used, e.g., for high-throughput sequencing and/or immune repertoire profiling. In some cases, the methods and compositions described herein can provide increased sensitivity, decreased background, or increased efficiency in high-throughput sequencing library preparation of immune receptor polynucleotides. In some cases, the methods and compositions described herein can provide increased detection of rare immune cell clonotypes, reduced sample requirements, or a combination thereof. In some embodiments, the improvement is provided by the sequential use of two flanking primers for enrichment of immune receptor sequences by PETE, where a first flanking primer hybridizes to a target polynucleotide and is extended with a polymerase, and a second flanking primer hybridizes to the extended first flanking primer and is extended with a polymerase. Thus, the sample is enriched for target polynucleotides containing the first primer hybridization site and a complement of the second primer hybridization site.

In a first aspect, the present invention provides a composition comprising: i) a plurality of structurally distinct immune cell receptor V gene specific primers, wherein the plurality comprises at least 10 structurally distinct primers having the following regions from 5' to 3': [5'-Phos], [SPLINT], [BARCODE], and [FW], wherein: [5'-Phos] comprises a 5' phosphate; [SPLINT] comprises an adaptor hybridization site of 2-8 nucleotides in length; [BARCODE] comprises a barcode region of at least 6 nucleotides in length, wherein each nucleotide of the barcode region is independently selected from the group consisting of N and W; and [FW] of each immune cell receptor V gene specific primer comprises a structurally distinct region that specifically hybridizes to a framework 1, framework 2, or framework 3 region of an immune cell receptor V gene.

In some embodiments, [BARCODE] comprises a barcode region of from 6 to 16 nucleotides in length. In some embodiments, the [FW] of each immune cell receptor V gene specific primer specifically hybridizes to a framework 1, framework 2, or framework 3 region of a T cell receptor V gene. In some embodiments, the [FW] of each immune cell receptor V gene specific primer specifically hybridizes to a framework 1, framework 2, or framework 3 region of a B cell receptor V gene. In some embodiments, the plurality comprises at least 10 of the primers set forth in SEQ ID Nos:1-121.

In some embodiments, the [SPLINT] consists of 6 consecutive nucleotides, preferably of the sequence CGA TCT. In some embodiments, [BARCODE] consists of thirteen consecutive nucleotides selected from the group consisting of N and W, preferably of the sequence WNN NNN WNN NNN W. In some embodiments, the composition comprises at least 50, preferably all of the primers set forth in SEQ ID NOs:1-121.

In a second aspect, the present invention provides a reaction mixture comprising: i) a plurality of structurally different target polynucleotides, wherein individual target polynucleotides of the plurality each comprise immune cell receptor V gene regions, optionally D gene regions, optionally C gene regions, and J gene regions; and ii) a plurality of immune cell receptor V gene specific primers according to any one of the preceding aspects or embodiments. In some embodiments, the plurality of immune cell receptor V gene specific primers are each hybridized to one of the plurality of structurally different target polynucleotides.

In some embodiments, a portion of the individual target polynucleotides of the plurality each comprise immune cell receptor D gene regions and a portion of the individual target polynucleotides of the plurality do not comprise immune cell receptor D gene regions. In some embodiments, the individual target polynucleotides of the plurality each comprise immune cell receptor D gene regions. In some embodiments, a portion of the individual target polynucleotides of the plurality each comprise immune cell receptor C gene regions and a portion of the individual target polynucleotides of the plurality do not comprise immune cell receptor C gene regions. In some embodiments, the individual target polynucleotides of the plurality each comprise immune cell receptor C gene regions. In some embodiments, the reaction mixture comprises a plurality of immune cell receptor C gene specific (C-segment) primers. In some embodiments, the plurality of immune cell receptor C gene specific primers are hybridized to one of the structurally different target polynucleotides.

In a third aspect, the present invention provides a reaction mixture comprising: i) a plurality of immune cell receptor specific first primer extension products, wherein the individual first primer extension products each comprise the following from regions from 5' to 3': a sequencer-specific adapter sequence, optionally a multiplex identifier (MID)

barcode, a unique molecular identifier (UID) barcode, at least a portion of an immune cell receptor framework 3 region, an immune cell receptor CDR3 region, an optional immune cell receptor diversity (D) region, an optional immune cell receptor constant (C) region, and at least a portion of an immune cell receptor J region; and ii) a plurality of J-gene specific primers, wherein each of the plurality of J-gene specific primers is hybridized to the immune cell receptor J region of one of the individual first primer extension products or a plurality of C gene specific primers, wherein each of the plurality of C gene specific primers is hybridized to the immune cell receptor C region of one of the individual first primer extension products.

In some embodiments, the reaction mixture further comprises a DNA polymerase. In some embodiments, the individual first primer extension products each comprise the multiplex identifier (MID) barcode. In some embodiments, a portion of the individual first primer extension products comprise the immune cell receptor D region and a portion of the first primer extension products do not comprise the immune cell receptor D region. In some embodiments, the individual target polynucleotides each comprise the immune cell receptor D region. In some embodiments, the plurality of J-gene specific primers comprise at least 10 of the primers set forth in SEQ ID Nos:122-204. In some embodiments, the plurality of J-gene specific primers comprise at least 50, preferably all of the primers set forth in SEQ ID Nos:122-204. In some embodiments, the individual target polynucleotides each comprise the immune cell receptor C region. In some embodiments, the plurality of C gene specific primers comprise at least two of the primers set forth in SEQ ID NOs:205-213. In some embodiments, the plurality of C gene specific primers comprise at least five, preferably all, of the primers set forth in SEQ ID NOs:205-213.

In a fourth aspect, the present invention provides a reaction mixture comprising: i) a plurality of first primer extension products, the individual first primer extension products each comprising the following from 5' to 3': a) a 5' phosphate; b) a SPLINT region comprising an adaptor hybridization site of 2-8 nucleotides in length; c) a unique molecular identifier (UID) barcode; d) at least a portion of an immune cell receptor framework 3 region; e) an immune cell receptor CDR3 region; f) an optional immune cell receptor diversity region; g) at least a portion of an immune cell receptor J region; and h) an optional immune cell receptor constant region; and i) a plurality of double-stranded splint adapters, each comprising: a) a 5' single-stranded overhang region hybridized to the SPLINT region of an individual first primer extension product; b) optionally a multiplex identifier (MID) barcode; and c) a sequencer-specific universal primer sequence.

In some embodiments, the reaction mixture further comprises ligase. In some embodiments, the double-stranded splint adapters each comprise a multiplex identifier (MID) barcode.

In a fifth aspect, the present invention provides a method for enriching from a sample a plurality of structurally different target polynucleotides, wherein individual target polynucleotides of the plurality comprise immune cell receptor V, J, and optionally C and/or D gene regions, the method comprising: a) providing a reaction mixture according to any one of the preceding aspects or embodiments that provide a reaction mixture, wherein the immune cell receptor V gene specific primers are hybridized to the V gene regions of the target polynucleotides; b) extending the hybridized immune cell receptor V gene specific primers with a polymerase, and then removing un-extended immune cell receptor V gene specific primers, if present, wherein the extended immune cell receptor V gene specific primers comprise at least a portion of the immune cell receptor V region, optionally the immune cell receptor D region, and at least a portion of the immune cell receptor J region; c) hybridizing a first universal adaptor to the [SPLINT] adaptor hybridization site of the extended immune cell receptor V gene specific primers; d) ligating the hybridized first universal adapters to the extended immune cell receptor V gene specific primers, and then removing un-ligated adapters, if present; e) hybridizing a plurality of immune cell receptor J gene specific primers to the J region portions of the extended immune cell receptor V gene specific primers, wherein the immune cell receptor J gene specific primers comprise a 3' J gene hybridizing region and a 5' second universal adapter region; and f) extending the hybridized immune cell receptor J gene specific primers with a polymerase, thereby forming a plurality of structurally different double-stranded products, each comprising at least a portion of the immune cell receptor V region, optionally the immune cell receptor D region, and at least a portion of the immune cell receptor J region flanked by a first and second universal adapter sequence.

In some embodiments, e) and f) are repeated 2 to 15 times by heating to denature double-stranded products, cooling to hybridize un-extended immune cell receptor J gene specific primers to the J region portions of the extended immune cell receptor V gene specific primers, and extending hybridized primers. In some embodiments, the removing un-extended immune cell receptor V gene specific primers comprises digesting single-stranded DNA exonuclease digestion. In some embodiments, the method further comprises amplifying double-stranded products comprising first and second universal adapters by universal PCR. In some embodiments, the structurally different target polynucleotides are cDNA. In some embodiments, prior to step a), a cDNA synthesis step is included to prepare cDNA from total RNA or mRNA. In some embodiments, step e) is modified such that the plurality of immune cell receptor J gene specific primers are substituted for a plurality of immune cell receptor C gene specific primers, thereby forming a plurality of structurally different double-stranded products, each comprising at least a portion of the immune cell receptor V region and at least a portion of the immune cell receptor C region.

DEFINITIONS

Figure 1:
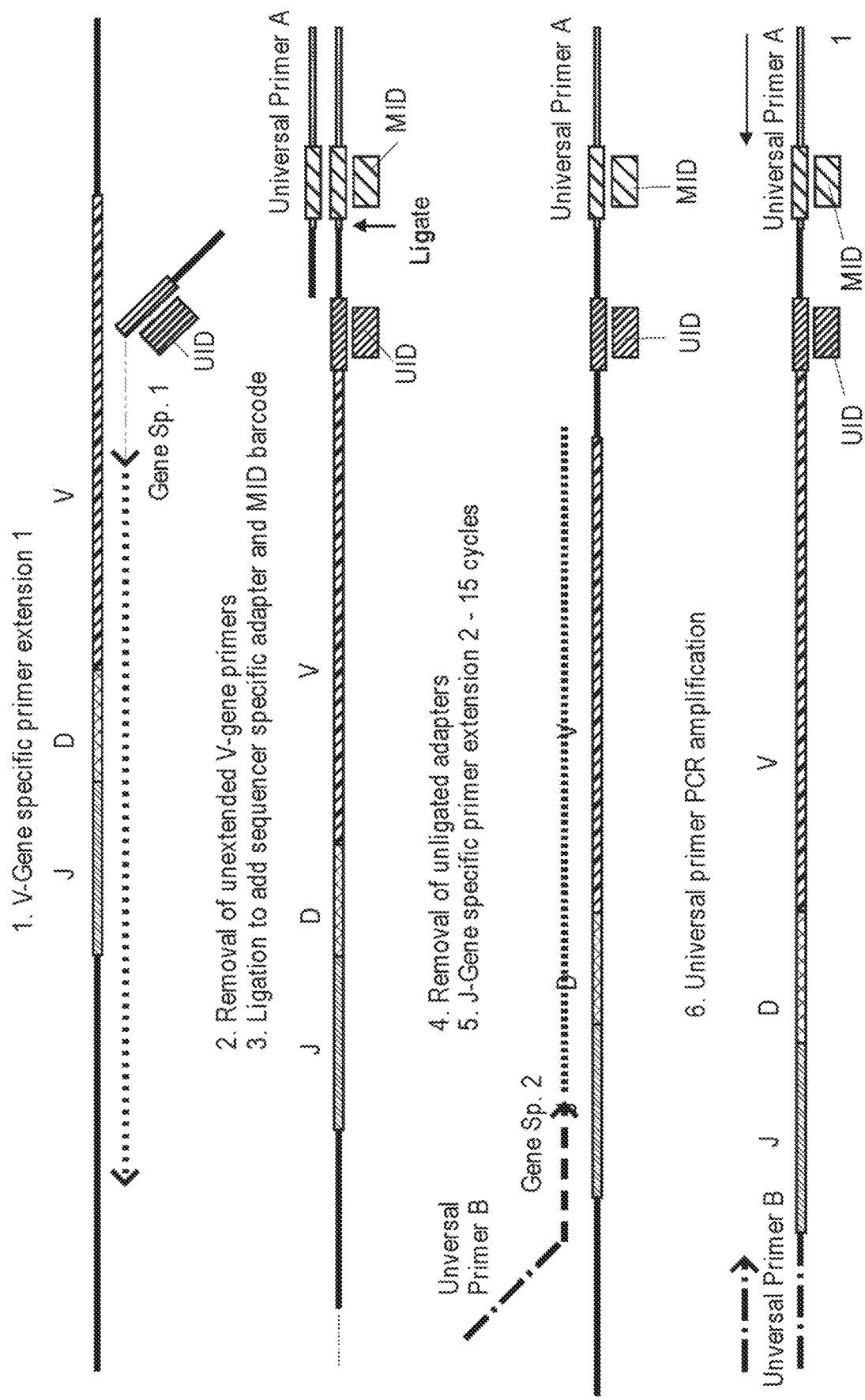
FIG. 1 illustrates an embodiment of an immuno-PETE reaction. The embodiment illustrated is a two-primer T cell receptor (TCR) primer extension target enrichment (PETE) reaction.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Spring Harbor Lab Press (Cold Spring Harbor, N.Y. 1989). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

As used herein, the term "substantially all" in reference to removing substantially all of a component of a reaction mixture means removing at least 90%, 95%, 99%, or more of a component.

As used herein, the term "immune cell receptor" refers to a T cell receptor (TCR), or a B cell receptor (BCR) (i.e., antibody). The BCR can be in a membrane bound form or a secreted form.

"T cell receptor" or "TCR" refers to the antigen recognition complex of a T cell. The TCR is composed of two different protein chains (e.g., alpha and beta or gamma and delta). Each chain is composed of two extracellular domains containing a variable region (V), a joining region (J), and a constant region (C). The variable region contains hypervariable complementarity determining regions (CDRs). Beta and delta TCR chains further contain a diversity region (D) between the V and J regions. Further TCR diversity is generated by VJ (for alpha and gamma chains) and VDJ (for beta and delta chains) recombination. The terms also refer to various recombinant and heterologous forms, including soluble TCRs expressed from a heterologous system.

The B cell receptor or "BCR" refers to the secreted or membrane bound antigen recognition complex of a B cell. The BCR is composed of two different protein chains (e.g., heavy and light). Each chain contains a variable region (V), a joining region (J), and a constant region (C). The variable region contains hypervariable complementarity determining regions (CDRs). Heavy chains can further contain a diversity region (D) between the V and J regions. Further BCR diversity is generated by VJ (for light chains) and VDJ (for heavy chains) recombination as well as somatic hypermutation of recombined chains. The terms also refer to various recombinant and heterologous forms.

As used herein, the term "barcode" refers to a nucleic acid sequence that can be detected and identified. Barcodes can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides long. Barcodes can employ error correcting codes such that one or more errors in synthesis, replication, and/or sequencing can be corrected to identify the barcode sequence. Examples of error correcting codes and their use in barcodes and barcode identification and/or sequencing include, but are not limited to, those described in U.S. 2010/0,323,348; and U.S. Pat. No. 8,715,967. In some cases, the barcodes are designed to have a minimum number of distinct nucleotides with respect to all other barcodes of a population. The minimum number can be 1, 2, 3, 4, 5, 6, 7, 8, 9, 10, 11, 12, 13, 14, 15, or more. Thus, for example, a population of barcodes having a minimum number of at least 5 distinct nucleotides will differ at at least 5 nucleotide positions from all other barcodes in the population.

As used herein, the term "multiplex identifier," "MID," and the like, refers to a barcode that identifies a source or sample. As such, all or substantially all, MID barcoded polynucleotides from a single source or sample will share an MID of the same sequence; while all, or substantially all (e.g., at least 90% or 99%), MID barcoded polynucleotides from different sources or samples will have a different MID barcode sequence. Polynucleotides from different sources or samples and having different MIDs can then be mixed and sequenced in parallel while maintaining source/sample information. Thus sequence reads can be assigned to individual samples.

As used herein, the term "universal identifier," "universal molecular identifier," "unique molecular identifier," "UID," and the like, refers to a barcode that identifies a polynucleotide to which it is attached. Typically, all, or substantially all (e.g., at least 90% or 99%), UID barcodes in a mixture of UID barcoded polynucleotides are unique.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologues, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

"Polymerase" refers to an enzyme that performs template-directed synthesis of polynucleotides. A DNA polymerase can add free nucleotides only to the 3' end of the newly forming strand. This results in elongation of the newly forming strand in a 5'-3' direction. No known DNA polymerase is able to begin a new chain (de novo). DNA polymerase can add a nucleotide only on to a pre-existing 3'—OH group, and, therefore, needs a primer at which it can add the first nucleotide. Non-limiting examples of polymerases include prokaryotic DNA polymerases (e.g. Pol I, Pol II, Pol III, Pol IV and Pol V), eukaryotic DNA polymerase, telomerase, reverse transcriptase and RNA polymerase. Reverse transcriptase is an RNA-dependent DNA polymerase which synthesizes DNA from an RNA template. The reverse transcriptase family contain both DNA polymerase functionality and RNase H functionality, which degrades RNA base-paired to DNA. RNA polymerase is an enzyme that synthesizes RNA using DNA as a template during the process of gene transcription. RNA polymerase polymerizes ribonucleotides at the 3'-end of an RNA transcript.

In some embodiments, a polymerase from the following may be used in a polymerase-mediated primer extension, end-modification (e.g., terminal transferase, degradation, or polishing), or amplification reaction: archaea (e.g., *Thermococcus litoralis* (Vent, GenBank: AAA72101), *Pyrococcus furiosus* (Pfu, GenBank: D12983, BAA02362), *Pyrococcus woesii, Pyrococcus* GB-D (Deep Vent, GenBank: AAA67131), *Thermococcus kodakaraensis* KODI (KOD, GenBank: BD175553, BAA06142; *Thermococcus* sp. strain KOD (Pfx, GenBank: AAE68738)), *Thermococcus gorgonarius* (Tgo, Pdb: 4699806), *Sulfolobus solataricus* (GenBank: NC002754, P26811), *Aeropyrum pernix* (GenBank: BAA81109), *Archaeglobus fulgidus* (GenBank: 029753), *Pyrobaculum aerophilum* (GenBank: AAL63952), *Pyrodictium occultum* (GenBank: BAA07579, BAA07580), *Thermococcus* 9 degree Nm (GenBank: AAA88769, Q56366), *Thermococcus fumicolans* (GenBank: CAA93738, P74918), *Thermococcus hydrothermalis* (GenBank: CAC18555), *Thermococcus* sp. GE8 (GenBank: CAC12850), *Thermococcus* sp. JDF-3 (GenBank: AX135456; WO0132887), *Thermococcus* sp. TY (GenBank: CAA73475), *Pyrococcus abyssi* (GenBank: P77916), *Pyrococcus glycovorans* (GenBank: CAC12849), *Pyrococcus horikoshii* (GenBank: NP 143776), *Pyrococcus* sp. GE23 (GenBank: CAA90887), *Pyrococcus* sp. ST700 (GenBank: CAC 12847), *Thermococcus pacificus* (GenBank: AX411312.1), *Thermococcus zilligii* (GenBank: DQ3366890), *Thermococcus aggregans, Thermococcus barossii, Thermococcus celer* (GenBank: DD259850.1), *Thermococcus profundus* (GenBank: E14137), *Thermococcus siculi* (GenBank: DD259857.1), *Thermococcus thioreducens, Thermococcus onnurineus* NA1, *Sulfolobus acidocaldarium, Sulfolobus tokodaii, Pyrobaculum calidifontis, Pyrobaculum islandicum* (GenBank: AAF27815), *Methanococcus jannaschii* (GenBank: Q58295), *Desulforococcus* species TOK, *Desulfurococcus, Pyrolobus, Pyrodictium, Staphylothermus, Vulcanisaetta, Methanococcus* (GenBank: P52025) and other archaeal B polymerases, such as GenBank AAC62712, P956901, BAAA07579)), thermophilic bacteria *Thermus* species (e.g., *flavus, ruber, thermophilus, lacteus, rubens, aquaticus*), *Bacillus stearothermophilus, Thermotoga maritima, Methanothermus fervidus*, KOD polymerase, TNA1 polymerase, *Thermococcus* sp. 9 degrees N-7, T4, T7, phi29, *Pyrococcus furiosus, P. abyssi, T. gorgonarius, T. litoralis, T. zilligii, T.* sp. GT, P. sp. GB-D, KOD, Pfu, *T. gorgonarius, T. zilligii, T. litoralis* and *Thermococcus* sp. 9N-7 polymerases.

In some embodiments, the polymerase can include a RNA polymerase from an eukaryote such as RNA polymerase I, RNA polymerase II, RNA polymerase III, RNA polymerase IV or RNA polymerase V. The polymerase can include a bacterial RNA polymerase as well as phage and viral RNA polymerases. In some aspects, the RNA polymerase can include a T7 RNA polymerase, T3 RNA polymerase, K11 RNA polymerase, K1F RNA polymerase, N4 RNA polymerase or SP6 RNA polymerase. In some embodiments, the RNA polymerase (e.g., *E. coli* RNA polymerase) can include a wild-type, mutant or artificially engineered RNA polymerase. As used herein, "an artificially engineered RNA polymerase" consists, or comprises, of at least one amino acid substitution, deletion or insertion with respect to the wild-type or naturally occurring RNA polymerase from which the artificially engineered RNA polymerase is obtained or derived.

In some embodiments, the polymerase can include a reverse transcriptase (RT). RT is an RNA-dependent DNA polymerase which synthesizes double-stranded DNA (cDNA) from a single-stranded RNA template. The RT family contain both DNA polymerase functionality and RNase H functionality, which degrades RNA base-paired to DNA. RT's are predominately associated with retroviruses although non-retroviruses also use RT (e.g., Hepatitis B virus). In some aspects, the polymerase can include a RT from Human Immunodeficiency Virus (e.g., HIV-1), Moloney Murine Leukemia Virus (e.g., M-MLV), Human T-Lymphotrophic Virus (e.g., HTLV), Avian Myeloblastosis Virus (e.g., AMV), Rous Sarcoma Virus (e.g., RSV), SuperScript RT (e.g., SuperScript IV), or Telomerase RT (e.g., TERT). In some embodiments, the RT can include a recombinant RT (e.g., an RT having one or more amino acid substitutions, deletions or additions as compared to the corresponding wild-type or naturally occurring RT). In some aspects, the RT includes transcription of RNA fragments of various sizes (e.g., 1 kb, 5 kb, 10 kb, 15 kb, 20 kb, or more).

The term "thermostable polymerase," refers to an enzyme that is stable to heat, is heat resistant, and retains sufficient activity to effect subsequent polynucleotide extension reactions and does not become irreversibly denatured (inactivated) when subjected to the elevated temperatures for the time necessary to effect denaturation of double-stranded nucleic acids. The heating conditions necessary for nucleic acid denaturation are well known in the art and are exemplified in, e.g., U.S. Pat. Nos. 4,683,202, 4,683,195, and 4,965,188, which are incorporated herein by reference. As used herein, a thermostable polymerase is suitable for use in a temperature cycling reaction such as the polymerase chain reaction ("PCR"), a primer extension reaction, or an end-modification (e.g., terminal transferase, degradation, or polishing) reaction. Irreversible denaturation for purposes herein refers to permanent and complete loss of enzymatic activity. For a thermostable polymerase, enzymatic activity refers to the catalysis of the combination of the nucleotides in the proper manner to form polynucleotide extension products that are complementary to a template nucleic acid strand. Thermostable DNA polymerases from thermophilic bacteria include, e.g., DNA polymerases from *Thermotoga maritima, Thermus aquaticus, Thermus thermophilus, Thermus flavus, Thermus fliformis, Thermus* species sps17, *Thermus* species Z05, *Thermus caldophilus, Bacillus caldotenax, Thermotoga neopolitana, Thermosipho africanus*, and other thermostable DNA polymerases disclosed above.

In some cases, the nucleic acid (e.g., DNA or RNA) polymerase may be a modified naturally occurring Type A polymerase. A further embodiment of the invention generally relates to a method wherein a modified Type A polymerase, e.g., in a primer extension, end-modification (e.g., terminal transferase, degradation, or polishing), or amplification reaction, may be selected from any species of the genus *Meiothermus, Thermotoga*, or *Thermomicrobium*. Another embodiment of the invention generally pertains to a method wherein the polymerase, e.g., in a primer extension, end-modification (e.g., terminal transferase, degradation or polishing), or amplification reaction, may be isolated from any of *Thermus aquaticus* (Taq), *Thermus thermophilus, Thermus caldophilus*, or *Thermus filiformis*. A further embodiment of the invention generally encompasses a method wherein the modified Type A polymerase, e.g., in a primer extension, end-modification (e.g., terminal transferase, degradation, or polishing), or amplification reaction, may be isolated from *Bacillus stearothermophilus, Sphaerobacter thermophilus, Dictoglomus thermophilum*, or *Escherichia coli*. In another embodiment, the invention generally relates to a method wherein the modified Type A polymerase, e.g., in a primer extension, end-modification (e.g., terminal transferase, degradation, or polishing), or amplification reaction, may be a mutant Taq-E507K polymerase. Another embodiment of the invention generally pertains to a method wherein a thermostable polymerase may be used to effect amplification of the target nucleic acid.

As used herein the term "primer" refers to an oligonucleotide which binds to a specific region of a single stranded template nucleic acid molecule and initiates nucleic acid synthesis via a polymerase-mediated enzymatic reaction, extending from the 3' end of the primer and complementary to the sequence of the template molecule. PCR amplification primers can be referred to as 'forward' and 'reverse' primers, one of which is complementary to a nucleic acid strand and the other of which is complementary to the complement of that strand. Typically a primer comprises fewer than about 100 nucleotides and preferably comprises fewer than about 30 nucleotides. Exemplary primers range from about 5 to about 25 nucleotides. Primers can comprise, for example, RNA and/or DNA bases, as well as non-naturally-occurring bases. The directionality of the newly forming strand (the daughter strand) is opposite to the direction in which DNA polymerase moves along the template strand.

As used herein, the term "universal primer" and "universal primers" refers to a primer that can hybridize to and support amplification of target polynucleotides having a shared complementary universal primer binding site. Similar, the term "universal primer pair" refers to a forward and reverse primer pair that can hybridize to and support PCR amplification of target polynucleotides having shared complementary forward and reverse universal primer binding sites. Such universal primer(s) and universal primer binding site(s) can allow single or double-primer mediated universal amplification (e.g., universal PCR) of target polynucleotide regions of interest.

As used herein the term "sample" refers to any biological sample that comprises nucleic acid molecules, typically comprising DNA and/or RNA. Samples may be tissues, cells or extracts thereof, or may be purified samples of nucleic acid molecules. Use of the term "sample" does not necessarily imply the presence of target sequence within nucleic acid molecules present in the sample. In some cases, the "sample" comprises immune cells (e.g., B cells and/or T cells), or a fraction thereof (e.g., a fraction enriched in genomic DNA, total RNA, or mRNA). In some embodiments, a sample can comprise a FACS sorted population of cells (such as human T cells) or a fixed formalin paraffin embedded (FFPE) tissue sample.

As used herein, the phrase "stringent hybridization conditions" refers to conditions under which a primer/probe will hybridize to its target, typically in a complex mixture of nucleic acids, but not to other nucleic acid sequences present in the complex mixture. Stringent conditions are sequence-dependent and will be different under different circumstances. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, high stringent conditions are selected to be about 5-10° C. lower than the thermal melting point ($T_m$) for the specific sequence at a defined ionic strength pH. Low stringency conditions are generally selected to be about 15-30° C. below the $T_m$. The $T_m$ is the temperature (under defined ionic strength, pH, and nucleic concentration) at which 50% of the primers/probes complementary to the target sequence hybridize to the target sequence at equilibrium. Stringent conditions include those in which the salt concentration is less than about 1.0 M sodium ion, typically about 0.01 to 1.0 M sodium ion concentration (or other salts) at pH 7.0 to 8.3 and the temperature is at least about 30° C. for short primers/probes (e.g., 10 to 50 nucleotides) and at least about 60° C. for long primers/probes (e.g., greater than 50 nucleotides). Stringent conditions may also be achieved with the addition of destabilizing agents such as formamide.

DETAILED DESCRIPTION OF THE INVENTION

I. Introduction

The present invention provides a primer extension target enrichment (PETE) method that includes two flanking primers and compositions for performing and using the flanking primer PETE (FP-PETE) method. The use of two flanking primers increases the stringency of the enrichment step as compared to methods that require only a single primer or single bait for enrichment of each structurally distinct target polynucleotide. Thus, in some cases, the FP-PETE method provides improved or synergistic target enrichment in comparison to other target enrichment methods such as, e.g., single primer extension target enrichment methods.

Moreover, in contrast to multiplex PCR based methods in which multiple first and second amplification primers are in the same reaction mixture at the same time, the FP-PETE method can include a step of removing un-extended first primers before introducing second primers into a reaction mixture. Thus, in some cases, the method can reduce or eliminate competition between first and second primers. As such, in some cases, the first or second primers, or both can be used at significantly higher concentrations in the FP-PETE reaction mixture as compared to, e.g., multiplex PCR based methods. Additionally, or alternatively, an increased number of first or second primers can be used in the FP-PETE reaction mixture as compared to, e.g., multiplex PCR based methods.

The use of a large number of first or second primers, a high concentration of first or second primers, or a combination thereof, can provide improved enrichment for, e.g., high-throughput sequencing sample workflows in which a large number of different polynucleotide sequences are targeted and flanking hybridization sequences for the target sequences are known. Such high-throughput sequencing sample workflows include, but are not limited to, immune repertoire profiling workflows in which B cell receptor (BCR) or T cell receptor (TCR) sequences are enriched from a sample, sequenced, and analyzed. Flanking primer extension target enrichment methods for immune repertoire profiling workflows is termed "immuno-PETE."

Hybridization conditions including those exemplified herein are readily determinable by one of ordinary skill in the art, and can include calculating primer/probe length, salt concentration, and preferential temperature to limit non-specific hybridization. In general, longer primers/probes require higher temperatures for correct annealing, while shorter primer/probes require lower temperatures. Hybridization generally depends on the ability of denatured DNA to anneal complementary nucleic acid sequences (e.g., primer/probes) present in an environment (e.g., a reaction mixture) below their melting temperature. The higher the degree of homology between a primer/probe and denatured DNA, the higher the annealing temperature can be while minimizing non-specific hybridization. Accordingly, higher relative annealing temperatures tend to make the reaction conditions more "stringent", while lower annealing temperatures make the reaction conditions less so. Additional details and explanations of hybridization stringency can be found for example in Ausubel et al., (Current Protocols in Molecular Biology, Wiley Interscience Publishers, (1995)).

In one aspect, the present invention provides first or second primers (e.g., SEQ ID NOs:1-121, 122-204, 205-213, etc.) that selectively hybridize to certain target polynucleotides. The phrase "selectively (or specifically) hybridizes to" refers to the binding, duplexing, or hybridizing of a molecule (e.g., a target polynucleotide) to a particular nucleotide sequence (e.g., a primer or probe comprising SEQ ID NOS:1-213) under stringent hybridization conditions when the target polynucleotide is present in a reaction mixture (e.g., total RNA, mRNA, cDNA or gDNA).

In one embodiment, the first or second primers described herein are complementary or substantially complementary (i.e., at least 70%, 75%, 80%, 85%, 90%, 95% or 99% complementary) to the target polynucleotides. In another embodiment, the first or second primers are complementary or substantially complementary (i.e., at least 70%, 75%, 80%, 85%, 90%, 95% or 99% complementary across at least 5, at least 10, at least 15, at least 20 or more nucleotides) to the target polynucleotides. In another embodiment, the first or second primers are complementary across their full-length to the target polynucleotides.

In another embodiment, the first or second primers are complementary or substantially complementary (i.e., at least 70%, 75%, 80%, 85%, 90%, 95% or 99% complementary) to a framework 1, framework 2, or framework 3 region of an immune cell receptor V gene. In another embodiment, the first or second primers are complementary or substantially complementary (i.e., at least 70%, 75%, 80%, 85%, 90%, 95% or 99% complementary across at least 5, at least 10, at least 15, at least 20 or more nucleotides) to a framework 1, framework 2, or framework 3 region of an immune cell receptor V gene. In another embodiment, the first or second primers are complementary across their full-length to a framework 1, framework 2, or framework 3 region of an immune cell receptor V gene.

In yet another embodiment, the first or second primers are complementary or substantially complementary (i.e., at least 70%, 75%, 80%, 85%, 90%, 95% or 99% complementary) to an immune cell receptor J gene region. In another embodiment, the first or second primers are complementary or substantially complementary (i.e., at least 70%, 75%, 80%, 85%, 90%, 95% or 99% complementary across at least 5, at least 10, at least 15, at least 20 or more nucleotides) to an immune cell receptor J gene region. In another embodiment, the first or second primers are complementary across their full-length to an immune cell receptor J gene region.

In another embodiment, the first or second primers are complementary or substantially complementary (i.e., at least 70%, 75%, 80%, 85%, 90%, 95% or 99% complementary) to an immune cell receptor C gene region. In another embodiment, the first or second primers are complementary or substantially complementary (i.e., at least 70%, 75%, 80%, 85%, 90%, 95% or 99% complementary across at least 5, at least 10, at least 15, at least 20 or more nucleotides) to an immune cell receptor C gene region. In another embodiment, the first or second primers are complementary across their full-length to an immune cell receptor C gene region.

In some embodiments, genomic DNA or cDNA comprising target polynucleotides of the invention can be identified under stringent hybridization conditions using the primer/probes sequences disclosed here (e.g., comprising any one or more of SEQ ID NOS:1-213). The following is an exemplary set of hybridization conditions performed on a thermocycler and is not limiting: a) denaturation of sample containing target polynucleotides at 98° C. for 2 minutes; b) hybridization or primers/probes at 60° C. for 20 minutes; c) extension of primers/probes using polymerase at 65° C. for 2 minutes; d) addition of Exonuclease I to reaction mixture at 37° C. for 10 minutes, increase temperature to 80° C. for a further 10 minutes, hold at 4° C.

In one embodiment, target polynucleotides that selectively hybridize to any one of the primer/probe sequences disclosed herein (e.g., SEQ ID NOS: 1-213) can be of any length, e.g., at least 10, 15, 20, 25, 30, 50, 100, 200, 500 or more nucleotides or having fewer than 500, 200, 100, or 50 nucleotides, etc.).

In one embodiment, a first primer is hybridized to a region of a target immune cell receptor polynucleotide that is 3' to a region of interest or at a 3' end of a region of interest. For example, the region of interest can include at least a portion of the immune cell receptor V region, at least a portion of the C region, the diversity (D) region if present, and at least a portion of the J region. In some cases, the first primer hybridizes to a framework region (e.g., a framework 1, framework 2, or framework 3 region) of the immune cell receptor V region. In some cases, the first primer hybridizes to the immune cell receptor C region (e.g., comprising a C-segment primer). The first primer can then be extended by a polymerase in a first extension reaction. Un-extended first primers and other single-stranded nucleic acid (e.g., denatured genomic DNA) can then be removed, e.g., by single-stranded DNA exonuclease digestion. In a second reaction, a second primer hybridizes to a region of the extended first primer that is 3' to the region of interest or at a 3' end of a region of interest. Thus, the first and second primers flank the region of interest when hybridized to their respective targets. In some cases, the second primer hybridizes to a J-gene region of the extended first primer. In some cases, the second primer hybridizes to a V-gene region of the extended first primer. In some cases, the second primer hybridizes to a C gene region of the extended first primer. The second primer can then be extended by a polymerase in a second extension reaction.

Alternatively, a first primer can be hybridized to a J-gene region of a target immune cell receptor polynucleotide that is 3' to a region of interest or at a 3' end of a region of interest. The hybridized first primer can then be extended by a polymerase. Un-extended first primers and other single-stranded nucleic acid (e.g., denatured genomic DNA) can then be removed, e.g., by single-stranded DNA exonuclease digestion. In a second reaction, a second primer can be hybridized to a framework region of the extended first primer and extended with a polymerase.

In one embodiment, complementary DNA (cDNA) can be prepared from RNA or mRNA for use in the PETE methods described herein. In one aspect, cDNA is prepared from total RNA or mRNA isolated and/or purified from a cell, cell lysate, sample or tissue. In one embodiment, RNA can include total RNA obtained using RNA isolation and/or extraction methods known in the art (e.g., Molecular Cloning: A Laboratory Manual, 4$^{th}$ Edition, Vol. 1, Chapter 6 (2012) incorporated herein by reference for all purposes; RNeasy Mini Kit (Catalog Number: 74104), Qiagen, Germantown, Md.). In another embodiment, cDNA can be synthesized from total RNA or mRNA transcripts using commercially available kits (for example, SuperScript III™ Reverse Transcriptase (Catalog Number: 18080093) or SuperScript® VILO™ cDNA Synthesis Kit (Catalog Number: 11754050), ThermoFisher Scientific, Waltham, Mass.). In another embodiment, cDNA can be prepared from total RNA or mRNA transcripts obtained from whole blood, peripheral blood mononuclear cell (PBMC), sorted lymphocytes, lymphocyte culture, fresh or fresh-frozen tumor tissue or formalin-fixed paraffin embedded (FFPE) tissue (for example, RNeasy FFPE kit, Qiagen, Germantown, Md.). In one aspect, cDNA synthesis can be initiated at or near the 3' termini of the mRNA transcript and terminates at or near the 5' end of the mRNA so as to generate "full-length" cDNA molecules.

Figure 4:
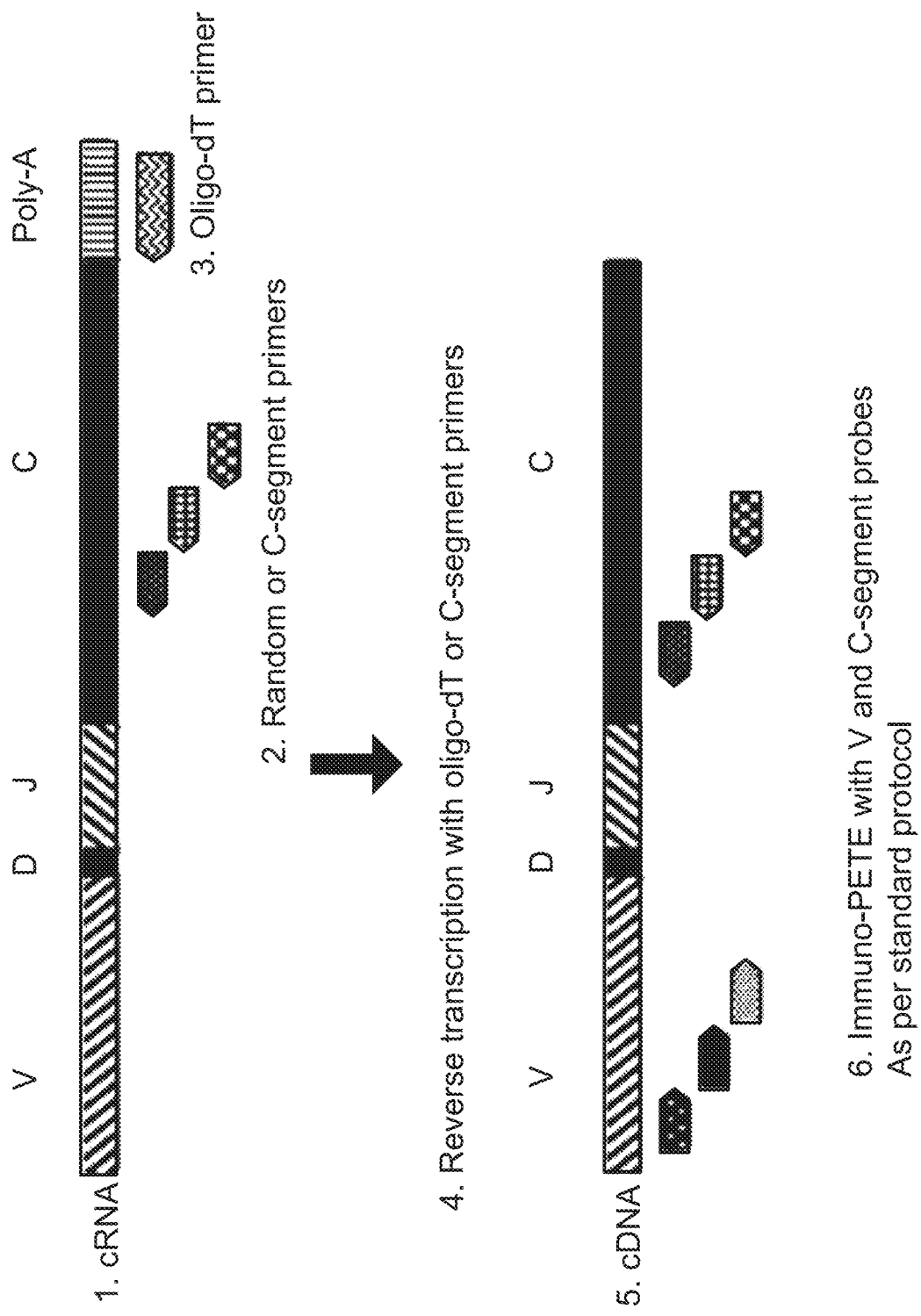
FIG. 4 illustrates an embodiment of an immuno-PETE reaction. The embodiment illustrated is a RNA or mRNA based immuno-PETE reaction.

In one embodiment, mRNA purified from a sample (e.g., cell, cell lysate or tissue) can be primed with an oligo-dT primer (e.g., a poly-T primer), random primer mixture (for example, a mixture or random hexamers, heptamers, octamers, nanomers, etc.,) or one or more isotype-specific immune receptor Constant-region (C-segment) primers (e.g., comprising SEQ ID NOS:205-213 of Table 6) under hybridization conditions sufficient to initiate cDNA synthesis (see FIG. 4). In one aspect, the oligo-dT primer facilitates the 3' end of the mRNA's in the sample being represented in the resulting cDNA molecules. In another aspect, the one or more isotype-specific immune receptor C-segment primers allows for hybridization of the C-segment primer to a complementary sequence among the one or more mRNA transcripts present in the sample. In one embodiment, the resulting cDNA molecules can be used in one or more of the PETE assays as described herein to produce one or more primer extension products that can be used to identify immune receptor isotypes in the sample. Accordingly, RNA or mRNA molecules of the sample can undergo first, and preferably, second strand synthesis to produce double-stranded cDNA molecules. In one embodiment, cDNA is prepared using an oligo-dT primer as set forth in this paragraph. In another embodiment, cDNA is prepared using a random primer mixture of hexamers, heptamers, octamers, nanomers, etc., as set forth in this paragraph. In another embodiment, cDNA is prepared using at least one isotype-specific immune receptor C-segment primer. In another embodiment, cDNA can be prepared using one or more C-gene region primers. For example Glanville et al., (*PNAS*, (2009) 106.48, 20216-21) discloses using a human heavy chain constant region primer, human kappa constant region primer and human lambda constant region primer to prepare cDNA from total RNA and/or mRNA from human samples. In yet another embodiment, cDNA is prepared using at least one of the isotype-specific immune receptor C-segment primers set forth in SEQ ID NOS:205-213.

Once prepared, the synthesized cDNA can be purified by any method known in the art (e.g., Solid Phase Reversible Immobilization (SPRI) paramagnetic beads or AMPure paramagnetic beads (Beckman Coulter, Brea, Calif.), filtration or centrifugation columns (e.g., RNeasy Mini Kit (Catalog Number: 74104), Qiagen, Germantown, Md.). The purified cDNA can then serve as a template for any of the methods described herein. In one embodiment, a plurality of V gene specific primers (e.g., comprising SEQ ID NOS:1-121) can be used in the first round of primer extension (gPE extension), followed by a second round of extension using one or more C-segment primers (e.g., comprising SEQ ID NOS:205-213, see Table 6). Alternatively, cDNA prepared as described herein can be used as the starting template for the PETE assays described herein (e.g., Example 1), where a plurality of V gene specific primers (e.g., comprising SEQ ID NOS:1-121) can be used in the first round of primer extension (gPE extension), followed by a second round of extension (PE2 extension) using a plurality of J-gene specific primers (e.g., comprising SEQ ID NOS:122-204).

II. Compositions

Described herein are compositions for performing immuno-PETE. Such compositions can include one or more, or all, of the following: primers, primer sets, polymerase extension products of such primers or primer sets (e.g., hybridized to a target polynucleotide), target polynucleotides (e.g., single-stranded target polynucleotides), reaction mixtures, DNA-dependent DNA polymerases, RNA-dependent DNA polymerases, single-stranded DNA exonucleases, nucleotides, buffers, salts, and the like.

In one embodiment, a composition containing a plurality of first primers is provided. In some cases, the plurality of first primers are immune cell receptor gene specific primers. The plurality of immune cell receptor gene specific primers can be configured to hybridize to, and thus enrich in a polymerase-mediated extension step, a plurality of target polynucleotides in a sample that encode immune cell receptor genes. The first primers can include a 5'-terminal phosphate ("[5'-Phos]"). The 5'-terminal phosphate can allow for ligation of the 5' end of the first primer, or a polymerase extension product thereof, to a 3'-OH of an adjacent polynucleotide.

The first primers can include a [SPLINT] region. The [SPLINT] region can include an adapter hybridization site of at least 2 nucleotides in length. In some cases, the adapter hybridization site is at least 4 nucleotides in length, at least 6 nucleotides in length, at least 8 nucleotides in length, from 2 to 10 nucleotides in length, or from 2 to 8 nucleotides in length. The [SPLINT] region can be complementary to a single-stranded 5' overhang region of a double-stranded adapter, such that when the single-stranded 5' overhang region of the double-stranded adapter hybridizes to the [SPLINT] region, a 3'-OH of the adapter can be ligated to the [5'-Phos] of the first primer or a polymerase extension product thereof. In some embodiments, [SPLINT] comprises or consists of 6 consecutive nucleotides that are complementary to a single-stranded 5' overhang region of a double-stranded adapter. In some embodiments, [SPLINT] comprises or consists of the sequence CGA TCT.

The first primers can include a [BARCODE] region that is or contains a barcode. The [BARCODE] region can be or contain a UID, an MID, or a combination thereof. In some cases, the [BARCODE] region comprises a UID. The [BARCODE] region can be any length from 2 to about 50 or more nucleotides. For UID barcodes, generally, the barcode length and composition is selected to encode more sequences than there are unique target polynucleotides to barcode. As such, for immune repertoire profiling, where estimates of diversity are generally significantly greater than $10^3$ and each unique sequence can be represented in a sample multiple times, the UID barcode can be at least 5, 6, 7, 8, 9, 10, 11, 12, 13, 14, 15, or 16 nucleotides in length. For example, in some cases the barcode can be from 6 to 16 nucleotides in length, from 8 to 14 nucleotides in length, or from 10 to 13 nucleotides in length. In some embodiments, the barcode is 13 nucleotides in length. In some cases, the barcode comprises nucleotides selected from the group consisting of N and W. In an exemplary embodiment, the barcode has a sequence of WNN NNN WNN NNN W.

The first primers can include a [FW] region. The [FW] region can be or contain a structurally distinct sequence that specifically hybridizes to a framework 1, framework 2, or framework 3 region of an immune cell receptor V gene region of an immune cell receptor (TCR or BCR) encoding target polynucleotide, wherein upon hybridization to the V gene region of an immune cell receptor encoding target polynucleotide, the first primer can be extended in the direction of the J gene region of the immune cell receptor encoding target polynucleotide. In some embodiments, the [FW] region hybridizes to a framework 1, framework 2, or framework 3 region of an TCR encoding target polynucleotide. In some embodiments, the [FW] region hybridizes to a framework 1, framework 2, or framework 3 region of a BCR encoding target polynucleotide. First primers containing a [FW] region can be used in an immuno-PETE method with second primers that hybridize to the J gene region of an immune cell receptor encoding target polynucleotide. In some embodiments, the first primers include the following regions: [5'-Phos], [SPLINT], [BARCODE], and [FW]. In some embodiments, the first primers include the following regions from 5' to 3': [5'-Phos], [SPLINT], [BARCODE], and [FW].

Alternatively, the first primers can include a J-specific region ([J]) that specifically hybridizes to a J gene region of an immune cell receptor encoding target polynucleotide, wherein upon hybridization to the J gene region of an immune cell receptor (TCR or BCR) encoding target polynucleotide, the first primer can be extended in the direction of the V gene region of the immune cell receptor encoding target polynucleotide. In some embodiments, the [J] region hybridizes to a J gene region of a TCR encoding target polynucleotide. In some embodiments, the [J] region hybridizes to a J gene region of a BCR encoding target polynucleotide. First primers containing a region [J] can be used in an immuno-PETE method with second primers that hybridize to the framework 1, framework 2, or framework 3 region of an immune cell receptor encoding target polynucleotide. In some embodiments, the first primers include the following regions: [5'-Phos], [SPLINT], [BARCODE], and [J]. In some embodiments, the first primers include the following regions from 5' to 3': [5'-Phos], [SPLINT], [BARCODE], and [J]. In another embodiment, the first primers can include a Constant-specific region ([C]) that specifically hybridizes to a C gene region of an immune cell receptor encoding target polynucleotide, wherein upon hybridization to the C gene region of an immune cell receptor (TCR or BCR) encoding target polynucleotide, the first primer can be extended in a 3' direction, through the C gene region of the immune cell receptor encoding target polynucleotide. In some embodiments, the [C] region hybridizes to a C gene region of a TCR encoding target polynucleotide. In some embodiments, the [C] region hybridizes to a C gene region of a BCR encoding target polynucleotide. In some embodiments, first primers containing a C-region [C] can be used in an immuno-PETE method with second primers that hybridize to the V-specific region ([V]) that specifically hybridizes to a V gene region of an immune cell receptor encoding target polynucleotide. In some embodiments, the first primers include the following regions: [5'-Phos], [SPLINT], [BARCODE], and [C]. In some embodiments, where the sample includes purified mRNA or total RNA, the first primers can include a C-segment primer that is complementary to, and hybridizes under hybridization conditions with a C gene region of an immune cell receptor encoding polynucleotide, or a complement thereof.

In one aspect, the present invention provides first primers (e.g., SEQ ID NOs:205-213) that can selectively hybridize to certain target polynucleotides. The phrase "selectively (or specifically) hybridizes to" refers to the binding, duplexing, or hybridizing of a molecule (e.g., a target polynucleotide) to a particular nucleotide sequence (e.g., a primer or probe comprising SEQ ID NOS:205-213) under stringent hybridization conditions when the target polynucleotide is present in a reaction mixture (e.g., total RNA, mRNA, cDNA or gDNA).

As described herein, target polynucleotides encoding a TCR β-chain or δ-chain can contain a D region that is positioned between a V region and a J region, whereas target polynucleotides encoding a TCR α-chain or γ-chain can lack a D region, such that the V region and J region are adjacent. Similarly, target polynucleotides encoding a BCR heavy chain can contain a D region that is positioned between a V region and a J region, whereas target polynucleotides encoding a BCR light chain can lack a D region, such that the V region and J region are adjacent.

As such, first primer extension products of first primers containing an [FW] region that are templated by a TCR β-chain or δ-chain or BCR heavy chain can, e.g., contain a VDJ region, or a portion of the V region, a D region, and a J region. Similarly, first primer extension products of first primers containing an [FW] region that are templated by a TCR α-chain or γ-chain or a BCR light chain can lack a D region, and thus contain a V region or portion thereof adjacent to a J region. Alternatively, first primer extension products of first primers containing a [J] region that are templated by a TCR β-chain or δ-chain or BCR heavy chain can, e.g., contain a VDJ region, or a portion of the J region, a D region, and a V region. Similarly, first primer extension products of first primers containing a [J] region that are templated by a TCR α-chain or γ-chain or a BCR light chain can lack a D region, and thus contain a J region or portion thereof adjacent to a V region.

In some embodiments, the plurality of first primers contains at least 2, at least 5, at least 10, at least 25, at least 50, at least 100, or all of the primers set forth in Table 1 (SEQ ID Nos:1-121). In one embodiment, the plurality of first primers contains at least 1 of the primers set forth in SEQ ID Nos:1-121. In some embodiments, the plurality of first primers contains at least 2, at least 5, at least 10, or all of the primers set forth in SEQ ID NOS:205-213. In one embodiment, the plurality of first primers contains at least 1 of the primers set forth in SEQ ID NOS:205-213. In one embodiment, the plurality of first primers are complementary or substantially complementary (i.e., at least 70%, 75%, 80%, 85%, 90%, 95% or 99% complementary) to an immune cell receptor C gene region. In another embodiment, the first primers are complementary or substantially complementary (i.e., at least 70%, 75%, 80%, 85%, 90%, 95% or 99% complementary across at least 5, at least 10, at least 15, at least 20 or more nucleotides) to an immune cell receptor C gene region. In another embodiment, the first primers are complementary across their full-length to an immune cell receptor C gene region.

TABLE 1

| SEQ ID NO: 1. | [5'-Phos]-[SPLINT]-[BARCODE]-GA ATG CCC TGA CAG CTC TCG CTT ATA |
|---|---|
| SEQ ID NO: 2. | [5'-Phos]-[SPLINT]-[BARCODE]-CT CAG AGA AGT CTG AAA TAT TCG ATG ATC AAT TCT CAG TTG |
| SEQ ID NO: 3. | [5'-Phos]-[SPLINT]-[BARCODE]-CC AAA TCG MTT CTC ACC TAA ATC TCC AGA CAA AG |
| SEQ ID NO: 4. | [5'-Phos]-[SPLINT]-[BARCODE]-CA CCT GAC TCT CCA GAC AAA GCT CAT |

TABLE 1-continued

| | |
|---|---|
| SEQ ID NO: 5. | [5'-Phos]-[SPLINT]-[BARCODE]-CC TGA ATG CCC CAA CAG CTC TC |
| SEQ ID NO: 6. | [5'-Phos]-[SPLINT]-[BARCODE]-GA TTC TCA GGG CGC CAG TTC TCT A |
| SEQ ID NO: 7. | [5'-Phos]-[SPLINT]-[BARCODE]-CC TAA TTG ATT CTC AGC TCA CCA CGT CCA TA |
| SEQ ID NO: 8. | [5'-Phos]-[SPLINT]-[BARCODE]-TC AGG GCG CCA GTT CCA TG |
| SEQ ID NO: 9. | [5'-Phos]-[SPLINT]-[BARCODE]-TC CTA GAT TCT CAG GTC TCC AGT TCC CTA |
| SEQ ID NO: 10. | [5'-Phos]-[SPLINT]-[BARCODE]-GA GGA AAC TTC CCT GAT CGA TTC TCA GC |
| SEQ ID NO: 11. | [5'-Phos]-[SPLINT]-[BARCODE]-CA ACT TCC CTG ATC GAT TCT CAG GTC A |
| SEQ ID NO: 12. | [5'-Phos]-[SPLINT]-[BARCODE]-AG GAA ACT TCC CTG ATC AAT TCT CAG GTC A |
| SEQ ID NO: 13. | [5'-Phos]-[SPLINT]-[BARCODE]-GG AAA CTT CCC TCC TAG ATT TTC AGG TCG |
| SEQ ID NO: 14. | [5'-Phos]-[SPLINT]-[BARCODE]-CC CCA ATG GCT ACA ATG TCT CCA GAT T |
| SEQ ID NO: 15. | [5'-Phos]-[SPLINT]-[BARCODE]-GG AGA GGT CCC TGA TGG CTA CAA |
| SEQ ID NO: 16. | [5'-Phos]-[SPLINT]-[BARCODE]-TC CCT GAT GGT TAT AGT GTC TCC AGA GC |
| SEQ ID NO: 17. | [5'-Phos]-[SPLINT]-[BARCODE]-GG AGA AGT CCC CAA TGG CTA CAA TGT C |
| SEQ ID NO: 18. | [5'-Phos]-[SPLINT]-[BARCODE]-AA AGG AGA AGT CCC GAA TGG CTA CAA |
| SEQ ID NO: 19. | [5'-Phos]-[SPLINT]-[BARCODE]-GT TCC CAA TGG CTA CAA TGT CTC CAG ATC |
| SEQ ID NO: 20. | [5'-Phos]-[SPLINT]-[BARCODE]-GA AGT CCC CAA TGG CTA CAA TGT CTC TAG ATT |
| SEQ ID NO: 21. | [5'-Phos]-[SPLINT]-[BARCODE]-GA GAA GTC CCC GAT GGC TAC AAT GTA |
| SEQ ID NO: 22. | [5'-Phos]-[SPLINT]-[BARCODE]-GT GAT CGG TTC TCT GCA CAG AGG T |
| SEQ ID NO: 23. | [5'-Phos]-[SPLINT]-[BARCODE]-CG CTT CTC TGC AGA GAG GAC TGG |
| SEQ ID NO: 24. | [5'-Phos]-[SPLINT]-[BARCODE]-GG TTC TTT GCA GTC AGG CCT GA |
| SEQ ID NO: 25. | [5'-Phos]-[SPLINT]-[BARCODE]-CA GTG GTC GGT TCT CTG CAG AG |
| SEQ ID NO: 26. | [5'-Phos]-[SPLINT]-[BARCODE]-GC TCA GTG ATC AAT TCT CCA CAG AGA GGT |
| SEQ ID NO: 27. | [5'-Phos]-[SPLINT]-[BARCODE]-TT CTC TGC AGA GAG GCC TGA GG |
| SEQ ID NO: 28. | [5'-Phos]-[SPLINT]-[BARCODE]-CC CAG TGA TCG CTT CTT TGC AGA AA |
| SEQ ID NO: 29. | [5'-Phos]-[SPLINT]-[BARCODE]-CT GCA GAG AGG CCT AAG GGA TCT |
| SEQ ID NO: 30. | [5'-Phos]-[SPLINT]-[BARCODE]-GA AGG GTA CAA TGT CTC TGG AAA CAA ACT CAA G |
| SEQ ID NO: 31. | [5'-Phos]-[SPLINT]-[BARCODE]-GG GGT ACT GTG TTT CTT GAA ACA AGC TTG AG |
| SEQ ID NO: 32. | [5'-Phos]-[SPLINT]-[BARCODE]-CA GTT CCC TGA CTT GCA CTC TGA ACT AAA C |
| SEQ ID NO: 33. | [5'-Phos]-[SPLINT]-[BARCODE]-AC TAA CAA AGG AGA AGT CTC AGA TGG CTA CAG |
| SEQ ID NO: 34. | [5'-Phos]-[SPLINT]-[BARCODE]-AG ATA AAG GAG AAG TCC CCG ATG GCT A |
| SEQ ID NO: 35. | [5'-Phos]-[SPLINT]-[BARCODE]-GA TAC TGA CAA AGG AGA AGT CTC AGA TGG CTA TAG |
| SEQ ID NO: 36. | [5'-Phos]-[SPLINT]-[BARCODE]-CT AAG GAT CGA TTT TCT GCA GAG AGG CTC |
| SEQ ID NO: 37. | [5'-Phos]-[SPLINT]-[BARCODE]-TT GAT TCT CAG CAC AGA TGC CTG ATG T |
| SEQ ID NO: 38. | [5'-Phos]-[SPLINT]-[BARCODE]-AT TCT CAG CTG AGA GGC CTG ATG G |
| SEQ ID NO: 39. | [5'-Phos]-[SPLINT]-[BARCODE]-GG ATC GAT TCT CAG CTA AGA TGC CTA ATG C |
| SEQ ID NO: 40. | [5'-Phos]-[SPLINT]-[BARCODE]-CT CAG CAG AGA TGC CTG ATG CAA CTT TA |
| SEQ ID NO: 41. | [5'-Phos]-[SPLINT]-[BARCODE]-CT GAT CGA TTC TCA GCT CAA CAG TTC AGT |
| SEQ ID NO: 42. | [5'-Phos]-[SPLINT]-[BARCODE]-TA GCT GAA AGG ACT GGA GGG ACG TAT |
| SEQ ID NO: 43. | [5'-Phos]-[SPLINT]-[BARCODE]-CC AGG AGG CCG AAC ACT TCT TTC T |
| SEQ ID NO: 44. | [5'-Phos]-[SPLINT]-[BARCODE]-GC TAA GTG CCT CCC AAA TTC ACC CT |

TABLE 1-continued

| | |
|---|---|
| SEQ ID NO: 45. | [5'-Phos]-[SPLINT]-[BARCODE]-CA CAG CTG AAA GAC CTA ACG GAA CGT |
| SEQ ID NO: 46. | [5'-Phos]-[SPLINT]-[BARCODE]-CT GCT GAA TTT CCC AAA GAG GGC C |
| SEQ ID NO: 47. | [5'-Phos]-[SPLINT]-[BARCODE]-AG GGT ACA GCG TCT CTC GGG |
| SEQ ID NO: 48. | [5'-Phos]-[SPLINT]-[BARCODE]-GC CTG ACC TTG TCC ACT CTG ACA |
| SEQ ID NO: 49. | [5'-Phos]-[SPLINT]-[BARCODE]-AT GAG CGA TTT TTA GCC CAA TGC TCC A |
| SEQ ID NO: 50. | [5'-Phos]-[SPLINT]-[BARCODE]-TG AAG GCT ACG TGT CTG CCA AGA G |
| SEQ ID NO: 51. | [5'-Phos]-[SPLINT]-[BARCODE]-CT CAT CTC AAT GCC CCA AGA ACG C |
| SEQ ID NO: 52. | [5'-Phos]-[SPLINT]-[BARCODE]-AG ATC TCT GAT GGA TAC AGT GTC TCT CGA CA |
| SEQ ID NO: 53. | [5'-Phos]-[SPLINT]-[BARCODE]-AG ATC TTT CCT CTG AGT CAA CAG TCT CCA GAA TA |
| SEQ ID NO: 54. | [5'-Phos]-[SPLINT]-[BARCODE]-CA CTG AAA AAG GAG ATA TCT CTG AGG GGT ATC ATG |
| SEQ ID NO: 55. | [5'-Phos]-[SPLINT]-[BARCODE]-GT TCC TGA AGG GTA CAA AGT CTC TCG AAA AG |
| SEQ ID NO: 56. | [5'-Phos]-[SPLINT]-[BARCODE]-CT GAG GGG TAC AGT GTC TCT AGA GAG A |
| SEQ ID NO: 57. | [5'-Phos]-[SPLINT]-[BARCODE]-AG CCG CCC AAA CCT AAC ATT CTC AA |
| SEQ ID NO: 58. | [5'-Phos]-[SPLINT]-[BARCODE]-CC CAG GAC CGG CAG TTC A |
| SEQ ID NO: 59. | [5'-Phos]-[SPLINT]-[BARCODE]-TT GAT TAG AGA CAT ATC CCT ATT GAA AAT ATT TCC TGG CA |
| SEQ ID NO: 60. | [5'-Phos]-[SPLINT]-[BARCODE]-AG ATG CCC TGA GTC AGC ATA GTC ATT CTA AC |
| SEQ ID NO: 61. | [5'-Phos]-[SPLINT]-[BARCODE]-GG AGG GGA AGG CCC CAC AGC GTC TTC |
| SEQ ID NO: 62. | [5'-Phos]-[SPLINT]-[BARCODE]-TG AAG TCA TAC AGT TCC TGG TGT CCA T |
| SEQ ID NO: 63. | [5'-Phos]-[SPLINT]-[BARCODE]-CC AAA TCA GGC TTT GGA GCA CCT GAT CT |
| SEQ ID NO: 64. | [5'-Phos]-[SPLINT]-[BARCODE]-CC AAA CAA AGG CTT AGA ATA TTT ATT ACA TGT C |
| SEQ ID NO: 65. | [5'-Phos]-[SPLINT]-[BARCODE]-CC AGG TCC CTG AGG CAC TCC ACC AGC T |
| SEQ ID NO: 66. | [5'-Phos]-[SPLINT]-[BARCODE]-CT GAA TCT AAA TTA TGA GCC ATC TGA CA |
| SEQ ID NO: 67. | [5'-Phos]-[SPLINT]-[BARCODE]-TC ATT CCT TAG TCG CTC TGA TAG TTA TGG TTA |
| SEQ ID NO: 68. | [5'-Phos]-[SPLINT]-[BARCODE]-CA TTC CTT AGT CGG TCT AAA GGG TAC AGT TA |
| SEQ ID NO: 69. | [5'-Phos]-[SPLINT]-[BARCODE]-AC AAC ATG ACC TAT GAA CGG TTC TCT TCA TC |
| SEQ ID NO: 70. | [5'-Phos]-[SPLINT]-[BARCODE]-CT GAA TTT AAC AAG AGC CAA ACC TCC TTC CA |
| SEQ ID NO: 71. | [5'-Phos]-[SPLINT]-[BARCODE]-CC GAC AGA AAG TCC AGC ACT CTG AG |
| SEQ ID NO: 72. | [5'-Phos]-[SPLINT]-[BARCODE]-CA CTG TTC TAT TGA ATA AAA AGG ATA AAC ATC TGT C |
| SEQ ID NO: 73. | [5'-Phos]-[SPLINT]-[BARCODE]-GT CAC CTT TGA TAC CAC CCT TAA ACA GAG TTT |
| SEQ ID NO: 74. | [5'-Phos]-[SPLINT]-[BARCODE]-AG ACT AAA TGC TAC ATT ACT GAA GAA TGG AAG CAG |
| SEQ ID NO: 75. | [5'-Phos]-[SPLINT]-[BARCODE]-TG AGG CTG AAT TTA TAA AGA GTA AAT TCT CCT TTA A |
| SEQ ID NO: 76. | [5'-Phos]-[SPLINT]-[BARCODE]-GC TGA ATT TAA GAA GAG TGA AAC CTC CTT CCA |
| SEQ ID NO: 77. | [5'-Phos]-[SPLINT]-[BARCODE]-GG CTG AAT TTA AGA GGA GTC AAT CTT CCT TCA A |
| SEQ ID NO: 78. | [5'-Phos]-[SPLINT]-[BARCODE]-GA CAC TTA TCA CTT CCC CAA TCA ATA CCC C |
| SEQ ID NO: 79. | [5'-Phos]-[SPLINT]-[BARCODE]-GG CTG AAT TTA ACA AGA GTC AAA CTT CCT TCC A |
| SEQ ID NO: 80. | [5'-Phos]-[SPLINT]-[BARCODE]-GC TGA ATT TAA GAA GAG CGA AAC CTC CTT CTA |
| SEQ ID NO: 81. | [5'-Phos]-[SPLINT]-[BARCODE]-CC ATG TAC CGT AAA GAA ACC ACT TCT TTC CA |
| SEQ ID NO: 82. | [5'-Phos]-[SPLINT]-[BARCODE]-CC ACA TAC CGT AAA GAA ACC ACT TCT TTC CA |
| SEQ ID NO: 83. | [5'-Phos]-[SPLINT]-[BARCODE]-TG GAT GCA GAC ACA AAG CAA AGC TC |
| SEQ ID NO: 84. | [5'-Phos]-[SPLINT]-[BARCODE]-TA AAG AAC TGC TTG GAA AAG AAA AAT TTT ATA GTG T |

TABLE 1-continued

| | |
|---|---|
| SEQ ID NO: 85. | [5'-Phos]-[SPLINT]-[BARCODE]-AC AGC TCA ATA GAG CCA GCC AGT ATA TTT C |
| SEQ ID NO: 86. | [5'-Phos]-[SPLINT]-[BARCODE]-CA GCT CAA TAA AGC CAG CCA GTA TGT TTC |
| SEQ ID NO: 87. | [5'-Phos]-[SPLINT]-[BARCODE]-GC ACA GGT CGA TAA ATC CAG CAA GTA TAT CTC |
| SEQ ID NO: 88. | [5'-Phos]-[SPLINT]-[BARCODE]-CT GTT ACA TTG AAC AAG ACA GCC AAA CAT TTC TC |
| SEQ ID NO: 89. | [5'-Phos]-[SPLINT]-[BARCODE]-CA CCG TTT TAT TGA ATA AGA CAG TGA AAC ATC TCT C |
| SEQ ID NO: 90. | [5'-Phos]-[SPLINT]-[BARCODE]-CC AGA AGG CAA GAA AAT CCG CCA A |
| SEQ ID NO: 91. | [5'-Phos]-[SPLINT]-[BARCODE]-AG AAG CGC TTG GAA AAG AGA AGT TTT ATA GTG T |
| SEQ ID NO: 92. | [5'-Phos]-[SPLINT]-[BARCODE]-TG ACC TTA ACA AAG GCG AGA CAT CTT TCC A |
| SEQ ID NO: 93. | [5'-Phos]-[SPLINT]-[BARCODE]-CG CTT GAC ACT TCC AAG AAA AGC AGT TC |
| SEQ ID NO: 94. | [5'-Phos]-[SPLINT]-[BARCODE]-CA GTC CTA TCA AGA GTG ACA GTT CCT TCC A |
| SEQ ID NO: 95. | [5'-Phos]-[SPLINT]-[BARCODE]-GA ACT TCC AGA AAT CCA CCA GTT CCT TCA A |
| SEQ ID NO: 96. | [5'-Phos]-[SPLINT]-[BARCODE]-GC TAA AAG CCA CAT TAA CAA AGA AGG AAA GCT T |
| SEQ ID NO: 97. | [5'-Phos]-[SPLINT]-[BARCODE]-CT CGC TGG ATA AAT CAT CAG GAC GTA GTA C |
| SEQ ID NO: 98. | [5'-Phos]-[SPLINT]-[BARCODE]-TC GCT ACG GAA CGC TAC AGC TT |
| SEQ ID NO: 99. | [5'-Phos]-[SPLINT]-[BARCODE]-CT CCT TCA ATA AAA GTG CCA AGC AGT TCT C |
| SEQ ID NO: 100. | [5'-Phos]-[SPLINT]-[BARCODE]-CA CTC TTA ATA CCA AGG AGG GTT ACA GCT A |
| SEQ ID NO: 101. | [5'-Phos]-[SPLINT]-[BARCODE]-TC AGT TTG GAG AAG CAA AAA AGA ACA GCT C |
| SEQ ID NO: 102. | [5'-Phos]-[SPLINT]-[BARCODE]-GA TCA TCA CAG AAG ACA GAA AGT CCA GCA C |
| SEQ ID NO: 103. | [5'-Phos]-[SPLINT]-[BARCODE]-GC AAT CGC TGA AGA CAG AAA GTC CAG TAC |
| SEQ ID NO: 104. | [5'-Phos]-[SPLINT]-[BARCODE]-CA GTT TGG TGA TGC AAG AAA GGA CAG TTC |
| SEQ ID NO: 105. | [5'-Phos]-[SPLINT]-[BARCODE]-CA GTC AAA GCT GAG GAA CTT TAT GGC CA |
| SEQ ID NO: 106. | [5'-Phos]-[SPLINT]-[BARCODE]-CT TCT TAA ACA AAA GTG CCA AGC ACC TCT C |
| SEQ ID NO: 107. | [5'-Phos]-[SPLINT]-[BARCODE]-CT GCT TCA TTT AAT GAA AAA AAG CAG CAA AGC TC |
| SEQ ID NO: 108. | [5'-Phos]-[SPLINT]-[BARCODE]-TT CTG TGA GCT TCC AGA AAA CAA CTA AAA CTA TTC A |
| SEQ ID NO: 109. | [5'-Phos]-[SPLINT]-[BARCODE]-CA CTG TAC TGT TGA ATA AAA ATG CTA AAC ATG TCT C |
| SEQ ID NO: 110. | [5'-Phos]-[SPLINT]-[BARCODE]-GC CTG TGA ACT TTG AAA AAA AGA AAA AGT TCA TCA A |
| SEQ ID NO: 111. | [5'-Phos]-[SPLINT]-[BARCODE]-CC AAG TTG GAT GAG AAA AAG CAG CAA AGT TC |
| SEQ ID NO: 112. | [5'-Phos]-[SPLINT]-[BARCODE]-TC AGT TTG GTA TAA CCA GAA AGG ACA GCT T |
| SEQ ID NO: 113. | [5'-Phos]-[SPLINT]-[BARCODE]-AA GTA GCA TAT TAG ATA AGA AAG AAC TTT CCA GCA T |
| SEQ ID NO: 114. | [5'-Phos]-[SPLINT]-[BARCODE]-CA GGC TTA AAA AAG GAG ACC AGC ACA TTT C |
| SEQ ID NO: 115. | [5'-Phos]-[SPLINT]-[BARCODE]-CT TCC AGA AAG CAG CCA AAT CCT TCA G |
| SEQ ID NO: 116. | [5'-Phos]-[SPLINT]-[BARCODE]-TG ATA CCA AAG CCC GTC TCA GCA C |
| SEQ ID NO: 117. | [5'-Phos]-[SPLINT]-[BARCODE]-GA GGC GGA AAT ATT AAA GAC AAA AAC TCC CC |
| SEQ ID NO: 118. | [5'-Phos]-[SPLINT]-[BARCODE]-CC ACA ATA AAC ATA CAG GAA AAG CAC AGC TC |
| SEQ ID NO: 119. | [5'-Phos]-[SPLINT]-[BARCODE]-AG AAA GCA GCG AAA TCC GTC GC |
| SEQ ID NO: 120. | [5'-Phos]-[SPLINT]-[BARCODE]-TG ACA TTG ATA TTG CAA AGA ACC TGG CTG T |
| SEQ ID NO: 121. | [5'-Phos]-[SPLINT]-[BARCODE]-GA AAC ACA TTC TGA CCC AGA AAG CCT TTC A |

In one embodiment, a composition containing a plurality of second primers is provided. In some cases, the plurality of second primers are immune cell receptor gene-specific primers. The plurality of immune cell receptor gene-specific primers can be configured to hybridize to, and thus enrich in a polymerase-mediated extension step, a plurality of target polynucleotides in a sample that encode immune cell receptor genes. The second primers can include a universal primer binding site, or complement thereof, and an immune cell receptor hybridizing region. In some cases, the second primers include from 5' to 3' a universal primer binding site and an immune cell receptor hybridizing region. In some cases, the second primer immune cell receptor hybridizing region is complementary to, and hybridizes under hybridization conditions with, a J-gene region of an immune cell receptor encoding polynucleotide, or a complement thereof. In some cases, the second primer immune cell receptor hybridizing region is complementary to, and hybridizes under hybridization conditions with, a V region of an immune cell receptor encoding polynucleotide (e.g., a framework 1, framework 2, or framework 3 region), or a complement thereof. In some cases, the second primer immune cell receptor hybridizing region is complementary to, and hybridizes under hybridization conditions with, a C gene region of an immune cell receptor encoding polynucleotide, or a complement thereof.

As described herein, target polynucleotides encoding a TCR β-chain or δ-chain can contain a D region that is positioned between a V region and a J region, whereas target polynucleotides encoding a TCR α-chain or γ-chain can lack a D region, such that the V region and J region are adjacent. Similarly, target polynucleotides encoding a BCR heavy chain can contain a D region that is positioned between a V region and a J region, whereas target polynucleotides encoding a BCR light chain can lack a D region, such that the V region and J region are adjacent.

Second primer extension products of second primers containing a [J] or an [FW] region that are templated by a first primer extension product templated by a TCR β-chain or δ-chain or BCR heavy chain can, e.g., contain a VDJ region, or a portion of the V region, a D region, and a portion of a J region. Similarly, second primer extension products of second primers containing a [J] or an [FW] region that are templated by first primer extension product templated by a TCR α-chain or γ-chain or a BCR light chain can lack a D region, and thus contain a V region or portion thereof adjacent to a J region or portion thereof.

In some embodiments, the plurality of second primers contains at least 2, at least 5, at least 10, at least 25, at least 50, at least 75, or all of the primers set forth in Table 2 (SEQ ID Nos:122-204. In one embodiment, the plurality of second primers contains at least 1 of the primers set forth in SEQ ID Nos:122-204. In some embodiments, the plurality of second primers contains at least 2, at least 5, at least 10, or all of the primers set forth in SEQ ID NOS:205-213. In one embodiment, the plurality of second primers contains at least 1 of the primers set forth in SEQ ID NOS:205-213.

In one embodiment, the second primers are complementary or substantially complementary (i.e., at least 70%, 75%, 80%, 85%, 90%, 95% or 99% complementary) to a framework 1, framework 2, or framework 3 region of an immune cell receptor V gene. In another embodiment, the second primers are complementary or substantially complementary (i.e., at least 70%, 75%, 80%, 85%, 90%, 95% or 99% complementary across at least 5, at least 10, at least 15, at least 20 or more nucleotides) to a framework 1, framework 2, or framework 3 region of an immune cell receptor V gene. In another embodiment, the second primers are complementary across their full-length to a framework 1, framework 2, or framework 3 region of an immune cell receptor V gene.

In yet another embodiment, the second primers are complementary or substantially complementary (i.e., at least 70%, 75%, 80%, 85%, 90%, 95% or 99% complementary) to an immune cell receptor J gene region. In another embodiment, the second primers are complementary or substantially complementary (i.e., at least 70%, 75%, 80%, 85%, 90%, 95% or 99% complementary across at least 5, at least 10, at least 15, at least 20 or more nucleotides) to an immune cell receptor J gene region. In another embodiment, the second primers are complementary across their full-length to an immune cell receptor J gene region.

TABLE 2

| SEQ ID NO: | Sequence |
|---|---|
| SEQ ID NO: 122. | AAT GAT ACG GCG ACC GAG ATC TAC ACT CTT TCC CTA CAC GAC GCT CTT CCG ATC TGG GGA GAA GTG GAA ACT CTG GTT CC |
| SEQ ID NO: 123. | AAT GAT ACG GCG ACC GAG ATC TAC ACT CTT TCC CTA CAC GAC GCT CTT CCG ATC TGG CTC TGA ACC AGA TAT AAT GAA TAC ATG GGT CCC |
| SEQ ID NO: 124. | AAT GAT ACG GCG ACC GAG ATC TAC ACT CTT TCC CTA CAC GAC GCT CTT CCG ATC TCC GGA TGC GTC TGG TCC C |
| SEQ ID NO: 125. | AAT GAT ACG GCG ACC GAG ATC TAC ACT CTT TCC CTA CAC GAC GCT CTT CCG ATC TTG TAC AGC CAG CCT GGT CCC |
| SEQ ID NO: 126. | AAT GAT ACG GCG ACC GAG ATC TAC ACT CTT TCC CTA CAC GAC GCT CTT CCG ATC TCT TGG CAC TTG GAG TCT TGT TCC |
| SEQ ID NO: 127. | AAT GAT ACG GCG ACC GAG ATC TAC ACT CTT TCC CTA CAC GAC GCT CTT CCG ATC TCA CGG ATG AAC AAT AAG GCT GGT TCC |
| SEQ ID NO: 128. | AAT GAT ACG GCG ACC GAG ATC TAC ACT CTT TCC CTA CAC GAC GCT CTT CCG ATC TTT GGT ATG ACC ACT TGG TTC CC |
| SEQ ID NO: 129. | AAT GAT ACG GCG ACC GAG ATC TAC ACT CTT TCC CTA CAC GAC GCT CTT CCG ATC TGA CCA GAA GTC GGG TGC C |
| SEQ ID NO: 130. | AAT GAT ACG GCG ACC GAG ATC TAC ACT CTT TCC CTA CAC GAC GCT CTT CCG ATC TAT TGA ACT TAC CTT TAA CAA ATA GTC TTG TTC C |
| SEQ ID NO: 131. | AAT GAT ACG GCG ACC GAG ATC TAC ACT CTT TCC CTA CAC GAC GCT CTT CCG ATC TAC TGA GTT CCA CTT TTA GCT GAG TGC C |
| SEQ ID NO: 132. | AAT GAT ACG GCG ACC GAG ATC TAC ACT CTT TCC CTA CAC GAC GCT CTT CCG ATC TAC CTG GAG AGA CTC GAA GCA TAG TCC C |
| SEQ ID NO: 133. | AAT GAT ACG GCG ACC GAG ATC TAC ACT CTT TCC CTA CAC GAC GCT CTT CCG ATC TCC TGA CCA GCA GTC TGG TCC C |
| SEQ ID NO: 134. | AAT GAT ACG GCG ACC GAG ATC TAC ACT CTT TCC CTA CAC GAC GCT CTT CCG ATC TCT TGG GAC TTG GAG CTT TGT TCC |
| SEQ ID NO: 135. | AAT GAT ACG GCG ACC GAG ATC TAC ACT CTT TCC CTA CAC GAC GCT CTT CCG ATC TTA CCA GGT TTT ACT GAT AAT CTT GTC CC |
| SEQ ID NO: 136. | AAT GAT ACG GCG ACC GAG ATC TAC ACT CTT TCC CTA CAC GAC GCT CTT CCG ATC TTT ACT CTG GAA CTC ACT GAT AAG GTG TTC C |
| SEQ ID NO: 137. | AAT GAT ACG GCG ACC GAG ATC TAC ACT CTT TCC CTA CAC GAC GCT CTT CCG ATC TCT GGA ACT CAC CTT TAA GGT GGG TTC C |
| SEQ ID NO: 138. | AAT GAT ACG GCG ACC GAG ATC TAC ACT CTT TCC CTA CAC GAC GCT CTT CCG ATC TTA CTT ACT AAG ATC TAA CAT GGT TCC |
| SEQ ID NO: 139. | AAT GAT ACG GCG ACC GAG ATC TAC ACT CTT TCC CTA CAC GAC GCT CTT CCG ATC TAG TCT TTA CTA GCA CCC TGG TTC C |
| SEQ ID NO: 140. | AAT GAT ACG GCG ACC GAG ATC TAC ACT CTT TCC CTA CAC GAC GCT CTT CCG ATC TCT GGA GCC AGA CAG TCA ACT GAG TTC C |
| SEQ ID NO: 141. | AAT GAT ACG GCG ACC GAG ATC TAC ACT CTT TCC CTA CAC GAC GCT CTT CCG ATC TCT TCA CTT GGA GTG ACA TTA TGT TTG GAT CC |
| SEQ ID NO: 142. | AAT GAT ACG GCG ACC GAG ATC TAC ACT CTT TCC CTA CAC GAC GCT CTT CCG ATC TTT ACT TGC TCT TTA AGT TAC TGT GGT TCC |
| SEQ ID NO: 143. | AAT GAT ACG GCG ACC GAG ATC TAC ACT CTT TCC CTA CAC GAC GCT CTT CCG ATC TTA ACT TAC TTG GTT TTA CAT TGA GTT TGG TCC C |
| SEQ ID NO: 144. | AAT GAT ACG GCG ACC GAG ATC TAC ACT CTT TCC CTA CAC GAC GCT CTT CCG ATC TCC TTT AAA ACA GTC AAT TGT GTC CC |
| SEQ ID NO: 145. | AAT GAT ACG GCG ACC GAG ATC TAC ACT CTT TCC CTA CAC GAC GCT CTT CCG ATC TGT TCA CAG ATA ACT CCG TTC C |
| SEQ ID NO: 146. | AAT GAT ACG GCG ACC GAG ATC TAC ACT CTT TCC CTA CAC GAC GCT CTT CCG ATC TGG TGA CCA CAA CCT GGG TCC C |

TABLE 2-continued

| SEQ ID NO: | Sequence |
|---|---|
| SEQ ID NO: 147. | AAT GAT ACG GCG ACC ACC GAG ATC TAC ACT CTT TCC CTA CAC GAC GCT CTT CCG ATC TTG ACA AGC CTT GTC CC |
| SEQ ID NO: 148. | AAT GAT ACG GCG ACC ACC GAG ATC TAC ACT CTT TCC CTA CAC GAC GCT CTT CCG ATC TGC AGC AAT CTG GTT CC |
| SEQ ID NO: 149. | AAT GAT ACG GCG ACC ACC GAG ATC TAC ACT CTT TCC CTA CAC GAC GCT CTT CCG ATC TGC ACG CGT AGT CCC |
| SEQ ID NO: 150. | AAT GAT ACG GCG ACC ACC GAG ATC TAC ACT CTT TCC CTA CAC GAC GCT CTT CCG ATC CAC AGT GAG TTT GGT CCC |
| SEQ ID NO: 151. | AAT GAT ACG GCG ACC ACC GAG ATC TAC ACT CTT TCC CTA CAC GAC GCT CTT CCG ATC TCT TGG TAT CGA GAG TTT GGT CCC |
| SEQ ID NO: 152. | AAT GAT ACG GCG ACC ACC GAG ATC TAC ACT CTT TCC CTA CAC GAC GCT CTT CCG ATC TTG CAA TCA CAG AAA GTC TTG TGC C |
| SEQ ID NO: 153. | AAT GAT ACG GCG ACC ACC GAG ATC TAC ACT CTT TCC CTA CAC GAC GCT CTT CCG ATC TCT GGG GAG AAT ATG AAG TCG TGT CCC |
| SEQ ID NO: 154. | AAT GAT ACG GCG ACC ACC GAG ATC TAC ACT CTT TCC CTA CAC GAC GCT CTT CCG ATC TGC TTC ACC AGC TGA GTT CC |
| SEQ ID NO: 155. | AAT GAT ACG GCG ACC ACC GAG ATC TAC ACT CTT TCC CTA CAC GAC GCT CTT CCG ATC TCT GGA CAG CAA GCA GAG TGC C |
| SEQ ID NO: 156. | AAT GAT ACG GCG ACC ACC GAG ATC TAC ACT CTT TCC CTA CAC GAC GCT CTT CCG ATC TGA CTT ACC TGG CTT TAT AAT TAG CTT GGT CCC |
| SEQ ID NO: 157. | AAT GAT ACG GCG ACC ACC GAG ATC TAC ACT CTT TCC CTA CAC GAC GCT CTT CCG ATC TTA CTT ACT TGG AAA GAC TTG TAA TCT GGT CCC |
| SEQ ID NO: 158. | AAT GAT ACG GCG ACC ACC GAG ATC TAC ACT CTT TCC CTA CAC GAC GCT CTT CCG ATC TCT GTG GTA CAA CAA TCA CTT GAG TGC C |
| SEQ ID NO: 159. | AAT GAT ACG GCG ACC ACC GAG ATC TAC ACT CTT TCC CTA CAC GAC GCT CTT CCG ATC TGG GGA ATA ACG AGT CTC GTT C |
| SEQ ID NO: 160. | AAT GAT ACG GCG ACC ACC GAG ATC TAC ACT CTT TCC CTA CAC GAC GCT CTT CCG ATC TCC TAC CTG GTT CTT GGT AAA GTT GTC CC |
| SEQ ID NO: 161. | AAT GAT ACG GCG ACC ACC GAG ATC TAC ACT CTT TCC CTA CAC GAC GCT CTT CCG ATC TCG GAT TTA CTG CCA GGC TTG TTC C |
| SEQ ID NO: 162. | AAT GAT ACG GCG ACC ACC GAG ATC TAC ACT CTT TCC CTA CAC GAC GCT CTT CCG ATC TGC GGG TTT GAC CAT TAA CCT TGT TCC |
| SEQ ID NO: 163. | AAT GAT ACG GCG ACC ACC GAG ATC TAC ACT CTT TCC CTA CAC GAC GCT CTT CCG ATC TGC TAA AAC CTT CAG CGA GGT GCC |
| SEQ ID NO: 164. | AAT GAT ACG GCG ACC ACC GAG ATC TAC ACT CTT TCC CTA CAC GAC GCT CTT CCG ATC TGT GAC CAA CAG CGA GGT GCC |
| SEQ ID NO: 165. | AAT GAT ACG GCG ACC ACC GAG ATC TAC ACT CTT TCC CTA CAC GAC GCT CTT CCG ATC TAC TTG GTT TAA CAG AGA GTT TAG TGC C |
| SEQ ID NO: 166. | AAT GAT ACG GCG ACC ACC GAG ATC TAC ACT CTT TCC CTA CAC GAC GCT CTT CCG ATC TAC TTG TTT CTG GTC TGG TCC C |
| SEQ ID NO: 167. | AAT GAT ACG GCG ACC ACC GAG ATC TAC ACT CTT TCC CTA CAC GAC GCT CTT CCG ATC TCG AGC GTG ACC TGA AGT CTT GTT CC |
| SEQ ID NO: 168. | AAT GAT ACG GCG ACC ACC GAG ATC TAC ACT CTT TCC CTA CAC GAC GCT CTT CCG ATC TCA GGG CTG GAT GAT TAG AGT CCC |
| SEQ ID NO: 169. | AAT GAT ACG GCG ACC ACC GAG ATC TAC ACT CTT TCC CTA CAC GAC GCT CTT CCG ATC TGG GCC TAA CTG CTA AAC GAG TCC C |
| SEQ ID NO: 170. | AAT GAT ACG GCG ACC ACC GAG ATC TAC ACT CTT TCC CTA CAC GAC GCT CTT CCG ATC TCA CAG GAC TTG ACT CTC AGA ATG CC |
| SEQ ID NO: 171. | AAT GAT ACG GCG ACC ACC GAG ATC TAC ACT CTT TCC CTA CAC GAC GCT CTT CCG ATC TAC TGG GTA TGA GTC TTG TTC C |
| SEQ ID NO: 172. | AAT GAT ACG GCG ACC ACC GAG ATC TAC ACT CTT TCC CTA CAC GAC GCT CTT CCG ATC TTG GAA TGA CGT CAA ACT TGT CCC |

TABLE 2-continued

| SEQ ID NO: | Sequence |
|---|---|
| SEQ ID NO: 172. | AAT GAT ACG GCG ACC ACC GAG ATC TAC ACT CTT TCC CTA CAC GAC GCT CTT CCG ATC TAC TTA CTT GGA ATG ACT GAT AAG CTT GTC CC |
| SEQ ID NO: 173. | AAT GAT ACG GCG ACC ACC GAG ATC TAC ACT CTT TCC CTA CAC GAC GCT CTT CCG ATC ATC TTG CTT GGC TTC ACA GTT AGT GTC TC |
| SEQ ID NO: 174. | AAT GAT ACG GCG ACC ACC GAG ATC TAC ACT CTT TCC CTA CAC GAC GCT CTT CCG ATC ATC TCT TGG ATG GAC AGT CAA GAT GGT CCC |
| SEQ ID NO: 175. | AAT GAT ACG GCG ACC ACC GAG ATC TAC ACT CTT TCC CTA CAC GAC GCT CTT CCG ATC ATC TAA CTT ACT TGG ATA GTC AGC CTG GTT C |
| SEQ ID NO: 176. | AAT GAT ACG GCG ACC ACC GAG ATC TAC ACT CTT TCC CTA CAC GAC GCT CTT CCG ATC ATC TTT GGG TTG ATT TAT TTT TGT ACT CAT CCC C |
| SEQ ID NO: 177. | AAT GAT ACG GCG ACC ACC GAG ATC TAC ACT CTT TCC CTA CAC GAC GCT CTT CCG ATC ATC TCC ACA CTT ACT TGT TCT AAC ACT CAG AGT TAT TCC |
| SEQ ID NO: 178. | AAT GAT ACG GCG ACC ACC GAG ATC TAC ACT CTT TCC CTA CAC GAC GCT CTT CCG ATC ATC TTA AAA CAT GGG TTT ACT GTC AGT TTC GTT CC |
| SEQ ID NO: 179. | AAT GAT ACG GCG ACC ACC GAG ATC TAC ACT CTT TCC CTA CAC GAC GCT CTT CCG ATC ATC TCC AGG ATT CAC TGT GAG CTG TGT CC |
| SEQ ID NO: 180. | AAT GAT ACG GCG ACC ACC GAG ATC TAC ACT CTT TCC CTA CAC GAC GCT CTT CCG ATC ATC TAG CTT CAC TCT CAC TTG CGT CCC |
| SEQ ID NO: 181. | AAT GAT ACG GCG ACC ACC GAG ATC TAC ACT CTT TCC CTA CAC GAC GCT CTT CCG ATC ATC TCC CAG GCT CAC AAT TAA CTC AGT CCC |
| SEQ ID NO: 182. | AAT GAT ACG GCG ACC ACC GAG ATC TAC ACT CTT TCC CTA CAC GAC GCT CTT CCG ATC ATC TTA CTT GCT GAG TTT CAT GAT TCC TCT AGT GTT |
| SEQ ID NO: 183. | AAT GAT ACG GCG ACC ACC GAG ATC TAC ACT CTT TCC CTA CAC GAC GCT CTT CCG ATC ATC TGT TCC ACA GTC ACA CGG GTT CC |
| SEQ ID NO: 184. | AAT GAT ACG GCG ACC ACC GAG ATC TAC ACT CTT TCC CTA CAC GAC GCT CTT CCG ATC ATC TCT GGT TCC ACG ATG AGT TGT GTT CC |
| SEQ ID NO: 185. | AAT GAT ACG GCG ACC ACC GAG ATC TAC ACT CTT TCC CTA CAC GAC GCT CTT CCG ATC ATC TGG CTC CAC GAA GAG TTT GAT GCC |
| SEQ ID NO: 186. | AAT GAT ACG GCG ACC ACC GAG ATC TAC ACT CTT TCC CTA CAC GAC GCT CTT CCG ATC ATC TCT GTT GTT CCA GAT AGG TTC C |
| SEQ ID NO: 187. | AAT GAT ACG GCG ACC ACC GAG ATC TAC ACT CTT TCC CTA CAC GAC GCT CTT CCG ATC ATC TGT CTT ACC TGT GAG TCT GGT GCC |
| SEQ ID NO: 188. | AAT GAT ACG GCG ACC ACC GAG ATC TAC ACT CTT TCC CTA CAC GAC GCT CTT CCG ATC ATC TCC TTA CCT ACA ACG GTT AAC CTG GTC CC |
| SEQ ID NO: 189. | AAT GAT ACG GCG ACC ACC GAG ATC TAC ACT CTT TCC CTA CAC GAC GCT CTT CCG ATC ATC TCT TAC TCA CCT ACA ACA GTG AGC CAA CTT CC |
| SEQ ID NO: 190. | AAT GAT ACG GCG ACC ACC GAG ATC TAC ACT CTT TCC CTA CAC GAC GCT CTT CCG ATC ATC TAT ACC CAA GAC AGA GAG CTG GGT TCC |
| SEQ ID NO: 191. | AAT GAT ACG GCG ACC ACC GAG ATC TAC ACT CTT TCC CTA CAC GAC GCT CTT CCG ATC ATC TAA CTT ACC TAG GAT GGA GAG TCG AGT CCC |
| SEQ ID NO: 192. | AAT GAT ACG GCG ACC ACC GAG ATC TAC ACT CTT TCC CTA CAC GAC GCT CTT CCG ATC ATC TCT GTC ACA GTG AGC CTG GTC CC |
| SEQ ID NO: 193. | AAT GAT ACG GCG ACC ACC GAG ATC TAC ACT CTT TCC CTA CAC GAC GCT CTT CCG ATC ATC TCA CGG TGA GCC GTG TCC C |
| SEQ ID NO: 194. | AAT GAT ACG GCG ACC ACC GAG ATC TAC ACT CTT TCC CTA CAC GAC GCT CTT CCG ATC ATC TCC AGT ACG GTC AGC CTA GAG CC |
| SEQ ID NO: 195. | AAT GAT ACG GCG ACC ACC GAG ATC TAC ACT CTT TCC CTA CAC GAC GCT CTT CCG ATC ATC TCA CTG TCA GCC TGC C |
| SEQ ID NO: 196. | AAT GAT ACG GCG ACC ACC GAG ATC TAC ACT CTT TCC CTA CAC GAC GCT CTT CCG ATC ATC TCA CTG AGA GCC TCC C |
| SEQ ID NO: 197. | AAT GAT ACG GCG ACC ACC GAG ATC TAC ACT CTT TCC CTA CAC GAC GCT CTT CCG ATC | |

TABLE 2-continued

| SEQ ID NO: | Sequence |
|---|---|
| SEQ ID NO: 198. | AAT GAT ACG GCG ACC ACC GAG ATC TAC ACT CTT TCC CTA CAC GAC GCT CTT CCG ATC TAC CAG GAG CCG CGT GCC |
| SEQ ID NO: 199. | AAT GAT ACG GCG ACC ACC GAG ATC TAC ACT CTT TCC CTA CAC GAC GCT CTT CCG ATC TCA CGG TCA GCC TGC C |
| SEQ ID NO: 200. | AAT GAT ACG GCG ACC ACC GAG ATC TAC ACT CTT TCC CTA CAC GAC GCT CTT CCG ATC TGA CCG TGA GCC TGC C |
| SEQ ID NO: 201. | AAT GAT ACG GCG ACC ACC GAG ATC TAC ACT CTT TCC CTA CAC GAC GCT CTT CCG ATC TGT GAA GTT ACT ATG AGC TTA GTC CCT TCA GCA AA |
| SEQ ID NO: 202. | AAT GAT ACG GCG ACC ACC GAG ATC TAC ACT CTT TCC CTA CAC GAC GCT CTT CCG ATC TCG AAG TTA CTA TGA GCC TAG TCC CTT TTG CAA A |
| SEQ ID NO: 203. | AAT GAT ACG GCG ACC ACC GAG ATC TAC ACT CTT TCC CTA CAC GAC GCT CTT CCG ATC TTG ACA ACA AGT GTT GTT CCA CTG CCA AA |
| SEQ ID NO: 204. | AAT GAT ACG GCG ACC ACC GAG ATC TAC ACT CTT TCC CTA CAC GAC GCT CTT CCG ATC TCT GTA ATG AGC TTT GTT CCG GGA CCA AA |

Described herein are target polynucleotides and compositions containing such target polynucleotides. In some cases, a composition containing such target polynucleotides further contains a DNA-dependent polymerase and/or a RNA-dependent DNA polymerase, a ligase, a first primer or a plurality of first primers, a second primer or plurality of second primers, first or second primer polymerase extension products, or a combination thereof. Generally, the target polynucleotides encode immune cell receptors, such as B cell receptors (i.e., antibodies), or T cell receptors, a complement thereof, or portions thereof. The target polynucleotides can be single stranded or double-stranded. The target polynucleotides can be DNA (e.g., genomic DNA). The target polynucleotides can be RNA (e.g., mRNA). The target polynucleotides can be cDNA generated by reverse transcription of mRNA. In an exemplary embodiment, the target polynucleotides are genomic DNA or cDNA that is heat denatured to form single-stranded targets.

In some embodiments, the target polynucleotides are obtained from a sample enriched for immune cells. For example, the target polynucleotides can be obtained from a sample enriched for T cells, enriched for B cells, enriched for T cells and B cells, enriched for lymphocytes, or enriched for peripheral blood mononuclear cells (PBMCs). In some cases, the target polynucleotides are obtained from a sample enriched for a fraction of T cells or B cells. For example, the sample can be enriched for T cells that express α/β TCRs. As another example, the sample can be enriched for T cells that express γ/δ TCRs. As yet another example, the sample can be enriched for B cells that express a certain isotype of BCR, or a set of such isotypes, such as IgA, IgG, IgM, IgE, or a combination thereof. As yet another example, the sample can be enriched for B cells expressing kappa light chain BCRs. As yet another example, the sample can be enriched for B cells expressing lambda light chain BCRs. As yet another example, the sample can be enriched for T cells that express α/β TCRs or γ/δ TCRs, wherein the sample is obtained by flow cytometry. As yet another example, the sample can be a FFPE tissue sample containing infiltrating lymphocytes. As yet another example, the sample can be a FFPE tissue sample, wherein the sample contains, or is suspected of containing, one or more tumor cells. Methods for enriching sample for a specific immune cell type include, but are not limited to, methods employing one or more of the following: ultracentrifugation, FICOLL™ gradient centrifugation, or flow cytometry (e.g., fluorescence-activated cell sorting (FACS)).

Described herein are reaction mixtures that contain target polynucleotides (e.g., target polynucleotides encoding B or T cell receptors, a complement thereof, or portions thereof), first primers, first primer extension products (e.g., single-stranded or hybridized to a target polynucleotide), second primers, second primer extension products (e.g., single-stranded or hybridized to a target polynucleotide), adapters (e.g., double stranded adapters, such as splint adapters), or a combination thereof. In some cases, the reaction mixture further contains a DNA-dependent DNA polymerase and/or a RNA-dependent DNA polymerase and reagents for polymerase-mediated and template-directed primer extension (e.g., divalent cations such as magnesium cations, nucleotide triphosphates, buffers, salts, etc.). In some cases, the DNA polymerase exhibits strand-displacing activity. In some cases, the DNA polymerase exhibits exonuclease activity. In some cases, the DNA polymerase does not exhibit or does not exhibit substantial strand-displacing activity. In some cases, the DNA polymerase does not exhibit or does not exhibit substantial exonuclease activity. In some cases, the DNA polymerase is thermostable. In some cases, the reaction mixture contains DNA ligase. In some embodiments, the RNA-dependent DNA polymerase is a telomerase. In some embodiments the RNA-dependent DNA polymerase lacks 3'-5' exonuclease activity. In some embodiments, the RNA-dependent DNA polymerase is thermostable.

In some embodiments, the reaction mixture contains a plurality of structurally different target polynucleotides, wherein individual target polynucleotides of the plurality each comprise immune cell receptor V gene regions, optionally D gene regions, optionally C gene regions, and J gene regions (e.g., target polynucleotides encoding immune cell receptor VJ, VDJ, or VJ and VDJ regions); and a plurality of first primers having [FW] regions. In some embodiments, the reaction mixture contains a plurality of structurally different target polynucleotides, wherein individual target polynucleotides of the plurality each comprise immune cell receptor V gene regions, optionally D gene regions, optionally C gene regions, and J gene regions (e.g., immune cell receptor VJ, VDJ, or VJ and VDJ regions); and a plurality of first primers having [J] regions or [C] regions.

In some embodiments, the first primers of the reaction mixture are hybridized to the target polynucleotides of the reaction mixture. In some embodiments, the reaction mixture contains a plurality of structurally different target polynucleotides hybridized to a plurality of first primer extension products (i.e., products of a DNA-polymerase-mediated and template-directed extension reaction). In some embodiments, the reaction mixture contains a plurality of structurally different immune cell receptor encoding target polynucleotides hybridized to a plurality of first primer DNA polymerase extension products.

In some embodiments, the reaction mixture contains a plurality of single-stranded target polynucleotides, the individual target polynucleotides each comprising the following from regions from 5' to 3': a sequencer-specific adapter sequence, optionally a multiplex identifier (MID) barcode, a unique molecular identifier (UID) barcode, at least a portion of an immune cell receptor framework 3 region, an immune cell receptor CDR3 region, an optional immune cell receptor diversity (D) region, an optional immune cell receptor constant (C) region, and at least a portion of an immune cell receptor J region, or the complements thereof. In some cases, such a plurality of single-stranded target polynucleotides are first primer extension products. In some cases, such a plurality of single-stranded target polynucleotides are first primer extension products ligated to an adapter comprising a universal primer binding site and optionally an MID barcode.

In some embodiments, the reaction mixture contains a plurality of single-stranded target polynucleotides, the individual target polynucleotides each comprising the following from regions from 5' to 3': a sequencer-specific adapter sequence, optionally a multiplex identifier (MID) barcode, a unique molecular identifier (UID) barcode, at least a portion of an immune cell receptor J-gene region, an optional D region, an optional immune cell receptor constant (C) region, an immune cell receptor CDR3 region, and at least a portion of an immune cell receptor framework 3 region, or the complements thereof. In some cases, such a plurality of single-stranded target polynucleotides are first primer extension products. In some cases, such a plurality of single-stranded target polynucleotides are first primer extension products ligated to an adapter comprising a universal primer binding site and optionally an MID barcode.

In some embodiments, a reaction mixture can contain one or more of the foregoing first primer extension products (e.g., adapter ligated first primer extension products) hybridized to a plurality of second primer extension products. In cases where the first primers hybridize to a framework region of an immune cell receptor encoding target polynucleotide, the second primers can be configured to hybridize to a J gene region or C gene region of the first primer extension products. In cases, where first primers hybridize to a complement of a J region or C region of an immune cell receptor encoding target polynucleotide, the second primers can be configured to hybridize to a framework region of the first primer extension products.

Described herein are adapters for downstream amplification or sequencing applications. Attachment of an adapter to one or both ends of a target polynucleotide, first primer extension product, or second primer extension product, can attach a UID barcode, an MID barcode, a universal primer binding site or complement thereof, or a combination thereof. Adapters containing a universal primer binding site or complement thereof can be referred to as universal adapters. In some embodiments, adapters are attached by ligation. In some embodiments, adapters are attached by hybridizing a primer containing an adapter sequence (e.g., an adapter sequence comprising or consisting of a universal primer binding site or complement thereof) to a target polynucleotide, first primer extension product, or second primer extension product. In some embodiments, the primer containing an adapter sequence is a second primer that can be hybridized to a first primer extension product and extended with a polymerase as described herein. In some embodiments, first adapters are ligated to a first primer extension product and second adapters are attached by hybridization of a second primer containing such an adapter to the first primer extension product and extending the second primer.

In some embodiments, one or more adapters are splint adapters. Splint adapters can be hybridized to a [SPLINT] region of a primer extension product (e.g., a first primer extension product) and ligated to a [5'-Phos] of the first primer extension product. Splint adapters can contain a double stranded region and a 5' single-stranded overhang region, wherein the 5' single-stranded overhang region is complementary to and hybridizes under hybridization conditions with the [SPLINT] region of the primer extension product (e.g., a first primer extension product). The 5' single-stranded overhang region can be at least 2 nucleotides in length, at least 4 nucleotides in length, at least 6 nucleotides in length, at least 8 nucleotides in length, from 2 to 10 nucleotides in length, or from 2 to 8 nucleotides in length. In some embodiments, the 5' single-stranded overhang region comprises or consists of 6 consecutive nucleotides that are complementary to the [SPLINT] region of the first primer extension product. In some embodiments, the 5' single-stranded overhang region comprises or consists of the sequence AGA TCG.

Splint adapters can contain a barcode and a universal primer binding site as described herein. In some cases, the splint adapter contains a MID barcode. In some cases, the splint adapter contains an MID barcode and a universal primer binding site. In some cases, the barcode is encoded in the double-stranded region of the splint adapter. In some cases, the universal primer binding site is encoded in the double-stranded region of the splint adapter. In some cases, the barcode (e.g., MID barcode) and the universal primer binding site is encoded in the double-stranded region of the splint adapter. In some embodiments, with respect to the strand of the splint adapter that contains the 5' single-stranded overhang region, in some cases, the universal primer binding site can be 3' of the barcode (e.g., MID barcode).

II. Methods

Described herein are methods for performing flanking primer (FP-) primer extension target enrichment (PETE) of target polynucleotides from a sample. In some embodiments, the target polynucleotides encode immune cell receptors, or portions thereof. In such embodiments, the methods can be referred to as immuno-PETE. The methods described herein can utilize a plurality of immune cell receptor V gene specific first primers each comprising an [FW] region at a 3' end for hybridizing to a framework (e.g., framework 1, framework 2, or framework 3) region of a target polynucleotide encoding an immune cell receptor. In such embodiments, the plurality of second primers each comprise a [J] region to flank the region of interest. Alternatively, the methods can utilize a plurality of immune cell receptor J gene specific first primers each comprising a [J] region at a 3' end for hybridizing to a J region of a target polynucleotide encoding an immune cell receptor. In such embodiments, the plurality of second primers each comprise a [FW] region to such that the first and second primers flank the region of interest in the target polynucleotides. In another embodiment, the methods can utilize a plurality of immune cell receptor C gene specific first primers each comprising a C-segment region at a 3' end for hybridizing to a C gene region of a target polynucleotide encoding an immune cell receptor. In such embodiments, the plurality of second primers can each comprise a [V] gene region such that the first and second primers flank the region of interest in the target polynucleotides.

In some embodiments, the method includes: a) providing a reaction mixture containing: i) a plurality of structurally different target polynucleotides as described herein, wherein the individual target polynucleotides encode immune cell receptor V gene regions, optionally D gene regions, optionally C gene regions, and J gene regions; and, ii) a plurality of immune cell receptor V gene specific primers or C gene specific primers (i.e., first primers) as described herein, wherein the immune cell receptor V gene specific primers are hybridized to the V gene regions of the target polynucleotides or wherein the immune cell receptor C gene specific primers are hybridized to the C gene regions of the target polynucleotides; b), extending the hybridized immune cell receptor V gene specific primers or C gene specific primers with a polymerase to generate extended immune cell receptor V gene specific primers or extended immune cell receptor C gene specific primers (i.e., first primer extension products) and then removing un-extended immune cell receptor V or C gene specific primers, if present, thereby generating extended immune cell receptor V gene specific primers containing at least a portion of the immune cell receptor V region, optionally the immune cell receptor D region, and at least a portion of the immune cell receptor J region or at least a portion of the immune cell receptor C region, optionally the immune cell receptor D region, and at least a portion of the immune cell receptor V region. In some cases, the removing un-extended immune cell receptor V or C gene specific primers includes contacting the un-extended immune cell receptor V or C gene specific primers with a single-stranded DNA exonuclease enzyme and thereby digesting the un-extended immune cell receptor V or C gene specific primers.

In some cases, the removing un-extended immune cell receptor V or C gene specific primers includes solid phase reversible immobilization of single-stranded first primer extension products or double stranded polynucleotides containing single-stranded target polynucleotide hybridized to single-stranded first primer extension product. In some cases, the removing un-extended immune cell receptor V or C gene specific primers includes resin (e.g., silica (e.g., silica bead)) or membrane-based column or batch purification of double-stranded DNA from single-stranded DNA or purification of a selected size of single or double stranded DNA from the reaction mixture. In some cases, the removing includes removing single or double-stranded DNA, or a combination thereof, having a size of less than about 100 bases or base pairs. In some cases, the removing includes removing single or double-stranded DNA, or a combination thereof, having a size of more than about 1,000 bases or base pairs. In some cases, the removing includes purifying from the sample primer extension products or double-stranded DNA containing primer extension products, or a combination thereof, having a size of more than about 100 bases or base pairs and less than about 1,000 bases or base pairs. In some cases, the removing further removes genomic DNA or denatured (e.g., single-stranded) genomic DNA from the sample. In some embodiments, the removing further removes denatured cDNA from the sample.

In some embodiments, the method includes: c) hybridizing a first universal adapter (e.g., a splint adapter containing a universal primer binding site) to a [SPLINT] adapter hybridization site of the extended immune cell receptor V or C gene specific primers; d) ligating the hybridized first universal adapter to the extended immune cell receptor V or C gene specific primers, and then removing un-ligated adapters, if present. In some cases, the removing un-ligated adapters includes solid phase reversible immobilization of adapter-ligated single-stranded first primer extension products or double stranded polynucleotides containing single-stranded target polynucleotide hybridized to such adapter-ligated single-stranded first primer extension product. In some cases, the removing un-ligated adapters includes resin (e.g., silica (e.g., silica bead)) or membrane-based column or batch purification of double-stranded DNA from single-stranded DNA or purification of a selected size of single or double stranded DNA from the reaction mixture. In some cases, the removing includes removing from a reaction mixture single or double-stranded DNA, or a combination thereof, having a size of less than about 100 bases or base pairs. In some cases, the removing includes removing from a reaction mixture single or double-stranded DNA, or a combination thereof, having a size of more than about 1,000 bases or base pairs. In some cases, the removing includes purifying from the sample adapter-ligated primer extension products or double-stranded DNA containing such adapter-ligated primer extension products, or a combination thereof, having a size of more than about 100 bases or base pairs and less than about 1,000 bases or base pairs.

In some embodiments, the method includes: e), hybridizing a plurality of immune cell receptor J gene specific primers (i.e., second primers) to the J region portions of the extended immune cell receptor V gene specific primers (i.e., first primer extension products), wherein the immune cell receptor J gene specific primers comprise a 3' J gene hybridizing region and a 5' second universal adapter region or hybridizing a plurality of immune cell receptor V gene specific primers (i.e., second primers) to the V region portions of the extended immune cell receptor C gene specific primers (i.e., first primer extension products), wherein the immune cell receptor V gene specific primers comprise a 3' V gene hybridizing region and a 5' second universal adapter region; and, f) extending the hybridized immune cell receptor J gene specific primers or extending the immune cell receptor V gene specific primers with a polymerase, thereby forming a plurality of structurally different double-stranded products comprising an extended immune cell receptor J gene specific primer or extended immune cell receptor V gene specific primer (i.e., second primer extension product) hybridized to an (e.g., adapter-ligated) extended immune cell receptor V gene specific primer or extended immune cell receptor C gene specific primer, each double-stranded product comprising at least a portion of the immune cell receptor V region, optionally the immune cell receptor D region, and at least a portion of the immune cell receptor J region flanked by a first and second universal adapter sequence or at least a portion of the immune cell receptor C region, optionally the immune cell receptor D region, and at least a portion of the immune cell receptor V region flanked by a first and second universal adapter sequence.

In some embodiments, the e) hybridizing and f) extending can be repeated multiple times by heating to denature double-stranded products produce in the extending of f) (e.g., double-stranded DNA products comprising first primer extension products (e.g., adapter-ligated extended immune cell receptor V or C gene specific primer) hybridized to second primer extension products (e.g., extended immune cell receptor J or V gene specific primer)), cooling to hybridize un-extended second primers to first primer extension products (e.g., adapter-ligated first primer extension products), and extending hybridized primers. In some cases, e) and f) are repeated 1, 2, 3, 4, 5, 6, 7, 8, 9, 10, 11, 12, 13, 14, 15 or more times. In some cases, e) and f) are repeated from 2 to 15 times, from 3 to 12 times, from 5 to 10 times, or from 5 to 15 times.

As described herein after extension of hybridized second primers, a polynucleotide containing at least a portion of a J-region, an optional D region, an optional C region, and at least a portion of a V region, flanked by universal primer binding sites, or a complement thereof is provided. This polynucleotide can be amplified by universal PCR with an amplification reaction mixture containing the polynucleotide, a forward universal primer and a reverse universal primer.

Although the foregoing invention has been described in some detail by way of illustration and example for purposes of clarity of understanding, one of skill in the art will appreciate that many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

All publications, patents, patent applications or other documents cited herein are hereby incorporated by reference in their entirety for all purposes to the same extent as if each individual publication, patent, patent application, or other document was individually indicated to be incorporated by reference for all purposes. Where a conflict exists between the instant application and a reference provided herein, the instant application shall dominate.

EXAMPLES

Example 1: Experimental Protocol—Immuno-PETE Using gDNA from Human PMBC

An schematic of an exemplary embodiment of immuno-PETE is illustrated in FIG. 1.

A pool of primers selected from SEQ ID NOS:1-121 (i.e., first primer pool (gPE primer mix)) and a pool of the primers selected from SEQ ID NOS: 122-204 (i.e., second primer pool (PE2 primer mix)) were generated. The concentration of primers in each primer pool was adjusted to 100 µM, and the pools were diluted to a working concentration of 12 µM. As a control, a target enrichment method using a previously tested panel of oncology related nucleic acid probes was analyzed in a separate reaction. Input human PMBC genomic DNA was used at 100 ng per reaction. Reaction mixtures were prepared and incubated as depicted below, in Table 3.

TABLE 3

Primer Hybridization Mix

| Reagent | Vol (μl) |
|---|---|
| Isothermal Amp Buffer (10×) | 4 |
| dNTPs (10 mM) | 1 |
| gPE primer mix (100 uM) | 2 |
| MgCl2 (25 mM) | 6 |
| total | 13 |

Aliquot 13 μl of Primer Hybridization Mix into each reaction tubes
Add water and samples to reaction tubes and mix as indicated above in the table
Place in thermocycler and run program Hyb and Extend 7-28

Polymerase Master Mix

| Reagent | Vol (μl) |
|---|---|
| Water | 8 |
| Isothermal Amp Buffer (10×) | 1 |
| NEB Bst 2.0 (8 U/ul) | 1 |
| total | 10 |

At 60° C. hold step, add 10 μl Polymerase Master Mix in each tubes and mix
Go to run, edit, skip step and contunue with run program Hyb and Extend 7-28

| Add Exonuclease 1 to samples | 1 μl |
|---|---|

Run program Exo 1 7-28
Perform AMPure clean up at 1.4 ratio

| KAPAPure to add | 70 |
|---|---|
| Elution Volume | 20 |

Ligation Master Mix

| Reagent | Vol (μl) |
|---|---|
| Water | 3.9 |
| T7 Ligase Buffer (2×) | 25 |
| T7 DNA ligase (3000 U/μl) | 0.1 |
| total | 29 |

Aliquot 29 μl Ligation Master Mix in each reaction tube
Add 20 μl gPE Extension Product and Mix
Add 1 μl of C7/P7 BC (Barcode) adapter (25 uM)
Incubate at 25° C. for 5 minutes
Add 50 μl of water to reach a volume of 100 μl
Perform AMPure clean up at 7.0× ratio

| KAPAPure to add | 70 |
|---|---|
| Elution Volume | 18 |

Primer Extension 2 (PE2) Master Mix

| Reagent | Vol (μl) |
|---|---|
| Phusion Mix (2×) | 25 |
| PE2 primer mix (20 uM) | 2 |
| Ammonium sulfate (200 mM) | 5 |
| total | 32 |

Aliquot 32 μl PE2 Master Mix in each reaction tube
Add 18 μl Ligation Product and Mix
Place in thermocycler and run program PE2 for 15 Cycles
Perform AMPure clean up at 1× ratio

| KAPAPure to add | 50 |
|---|---|
| Elution Volume | 20 |

TABLE 3-continued

PETE CR Master Mix - 50 uL

| Reagent | Vol (μl) |
|---|---|
| Water | 4 |
| Phusion Mix (2×) | 25 |
| C5/C7 primer Mix (10 uM) | 1 |
| total | 30 |

Add 20 μl of the Primer extension 2 product
Place in thermocycler and run program PETE CR
Perform AMPure clean up at 0.9× ratio

| KAPAPure to add | 45 |
|---|---|
| Elution Volume | 20 |

Thermal Cycling Protocols are depicted in Table 4.

TABLE 4

Hyb and Extend 7-28 Program

98° C. - 2 minutes
80° C. - 0 seconds
60° C. - 20 minutes
60° C. - hold
65° C. - 2 minutes
80° C. - 10 minutes
4° C. - hold

Exo I 7-28 Program

37° C. - 10 minutes
80° C. - 10 minutes
4° C. - hold

PE2 Program

98° C. - 1 minute
15 cycles
98° C. - 10 seconds
80° C. - 20 seconds
64° C. - 20 seconds
72° C. - 30 seconds
4° C. - hold

PETE CR Program

Figure 2:
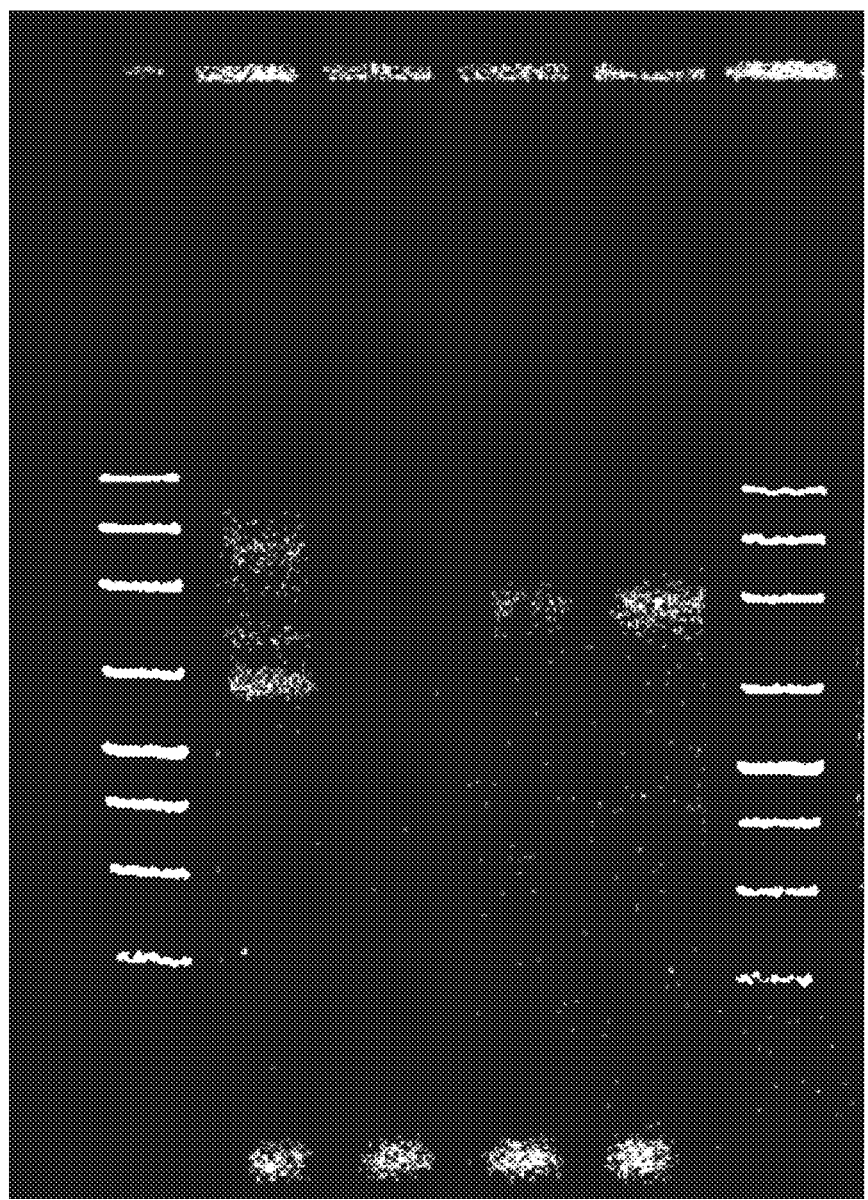
FIG. 2 is an image of exemplary primer extension products obtained by the immuno-PETE assay of Example 1 analyzed by agarose gel electrophoresis.

98° C. - 1 minute
24 cycles
98° C. - 10 seconds
60° C. - 20 seconds
72° C. - 30 seconds
4° C. - hold Immuno-PETE reactions were analyzed by agarose gel electrophoresis (FIG. 2). The TCR library (generated with first primers (selected from SEQ ID NOS: 1-121) and second primers (selected from SEQ ID NOS:122-204) and RH-4 library (generated with the oncology panel of probes (Control)) were diluted to a final concentration of 4 nM, and pooled in a 4:1 ratio of TCR to RH-4 for Illumina sequencing. Sequencing was performed on the Illumina MiSeq instrument using paired-end 2×250 cycle sequencing. Over 15 million filtered pass reads were generated and analyzed.

Results:

The results of the TCR library and RH-4 library are summarized in Table 5.

TABLE 5

| | Sequencing Summary | | |
|---|---|---|---|
| Analysis | Imaging Summary | Indexing | |

| Reads mapped to Index ID | | | | | |
|---|---|---|---|---|---|
| Total Reads | PF Reads | % Reads Identified (PF) | CV | Min | Max |
| 15805692 | 15271036 | 85.4589 | 0.8277 | 17.7223 | 67.7366 |

| Index Number | Sample Id | Project | Index 1 (17) | Index 2 (15) | % Reads Identified (PF) |
|---|---|---|---|---|---|
| 1 | TCR-PETE | NA | ATCACG | | 67.7366 |
| 2 | RH4-PETE | NA | TGACCA | | 17.7223 |

A random subsample of 150,000 sequences, corresponding to 50× the expected number of different V(D)J sequences in the input genomic sample, was further analyzed. This subsample of sequencing data was de-duplicated. The de-duplicated (12K) and de-deduplicated (150K) data were processed to identify polynucleotides containing rearranged V(D)J regions. The results are summarized in Table 6.

TABLE 6

| | TCR Alignment Result | | | | | | | | | | |
|---|---|---|---|---|---|---|---|---|---|---|---|
| Sample | Total_input_read_pairs | Total_reads_pairs_after_filtering | %_input_reads_after_filtering | Unique_read_pairs | Duplicate_read_pairs | Unassigned_read_pairs | %_Duplicate_Rate | Consensus_reads | TCRB_productive_unique_consensus_reads | Clones | d50 | Shannon_entropy |
| TCR-PETE_1_sampled 50× | 150000 | 139654 | 93.1 | 2376 | 127231 | 10018 | 98.2 | 1699 | 174 | 108 | 0.96296296 | 100.8085935 |
| TCR-PETE_S1_sampled_4× | 12000 | 11178 | 93.2 | 1418 | 8955 | 803 | 86.3 | 1081 | 105 | 99 | 0.97979798 | 98.0031575 |

Figure 3:
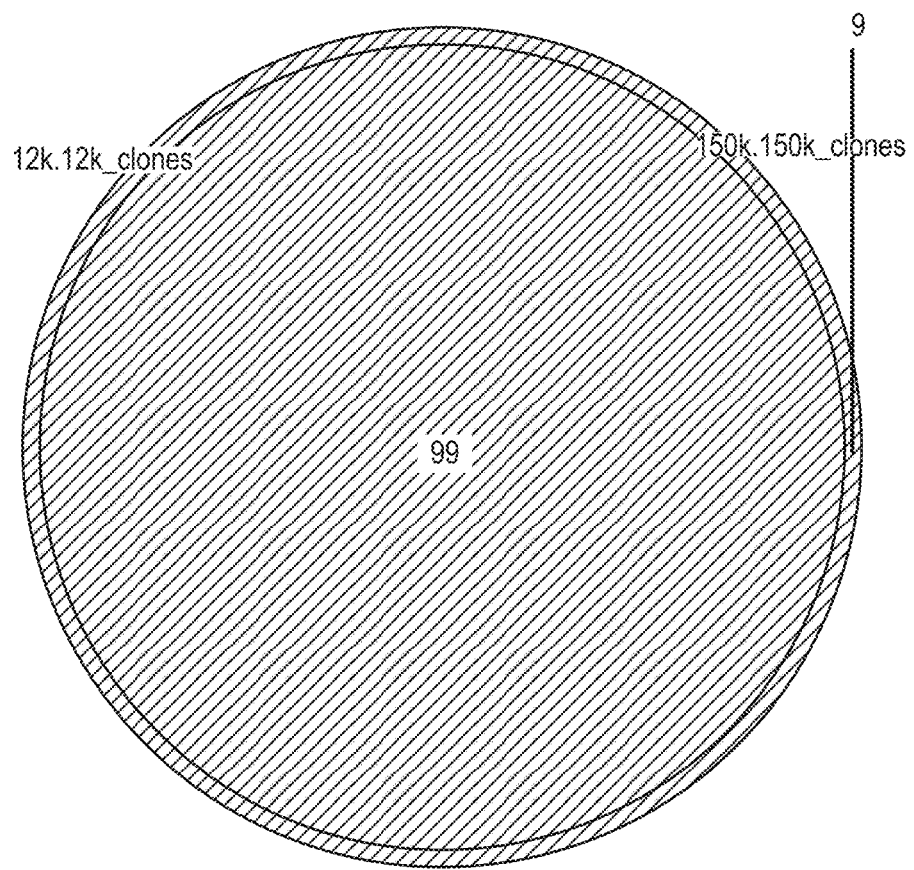
FIG. 3 is a Venn diagram demonstrating the number of clones and overlap between deduped and de-deduped sequencing data from exemplary primer extension products obtained by the immuno-PETE assay of Example 1.

Out of the 1081 sequences assigned in the 12 k sample to 99 clones, 100% have the same clone assigned when they were present in the 150 k set. There were in total 108 clones assigned to both sets, with 99 clones overlapping between the two sets. A Venn diagram of the overlap between the 12 k set and the 150 k set is depicted in FIG. 3.

An analysis of top ranked TCR clones from the sample before and after de-duplication showed that the ranking can change as a result of de-duplication, as shown in Table 7.

TABLE 7

Top 10 ranking clones for TCRαβ and TCRγδ isotypes
(TRA-Top10-Non-Dedup SEQ ID NO: 214-253; TRA-Top10-Dedup: SEQ ID NO 244-253;
TRB-Top10-Non-Dedup: SEQ ID NO 224-233; TRB Top10-Dedup: SEQ ID NO:254-263;
TRG-Top10-Non-Dedup: SEQ ID NO: 234-243;TRG-Top10-Dedup: 264-273)

| TRA-Top10-Non-Dedup | | TRA-Top10-Non-Dedup | |
|---|---|---|---|
| Clone Rank | Clone | Clone Rank | Clone |
| 1. | TRAV27*_TRAJ42*_CAGGGSQGNLIF | 1. | TRAV27*_TRAJ42*_CAGGGSQGNLIF |
| 2. | TRAV12-2*_TRAJ43*_WPTGMRF | 2. | TRAV12-2*_TRAJ43*_WPTGMRF |
| 3. | TRAV38-1*_TRAJ33*_CAFMTPDSNYQLIW | 3. | TRAV38-1*_TRAJ33*_CAFMTPDSNYQLIW |
| 4. | TRAV21*_TRAJ45*_CAVGGYSGGGADGLTF | 4. | TRAV21*_TRAJ45*_CAVGGYSGGGADGLTF |
| 5. | TRAV25*_TRAJ28*_CAGSGAGSYQLTF | 5. | TRAV25*_TRAJ28*_CAGSGAGSYQLTF |
| 6. | TRAV1-2*_TRASJ27*_CAVSTNAGKSTF | 6. | **TRAV13-1*_TRAJ18*_CAAKGRGSTLGRLYF** |
| 7. | TRAV13-1*_TRAJ18*_CAAKGRGSTLGRLYF | 7. | **TRAV27*_TRAJ42*_CAGGGSQGNLIF** |
| 8. | TRAV27*_TRAJ42*_CAGGGSQGNLIF | 8. | **TRAV1-2*_TRASJ27*_CAVSTNAGKSTF** |

TABLE 7-continued

Top 10 ranking clones for TCRαβ and TCRγδ isotypes
(TRA-Top10-Non-Dedup SEQ ID NO: 214-223; TRA-Top10-Dedup: SEQ ID NO 244-253;
TRB-Top10-Non-Dedup: SEQ ID NO 224-233; TRB Top10-Dedup: SEQ ID NO:254-263;
TRG-Top10-Non-Dedup: SEQ ID NO: 234-243;TRG-Top10-Dedup: 264-273)

| | | | |
|---|---|---|---|
| 9. | TRAV26-1*_TRAJ47*_CIVRVVEYGNKLVF | 9. | **TRAV26-1*_TRAJ47*_CIVRVVEYGNKLVF** |
| 10 | TRAV5*_TRAJ4*_CAESEDSGGYNKLIF | 10 | **TRAV13-2*_TRAJ13*_CAEMAPGGYQKVTF** |

| TRB-Top10-Non-Dedup | TRB-Top10-Non-Dedup |
|---|---|

| Clone Rank | Clone | Clone Rank | Clone |
|---|---|---|---|
| 1. | TRB19*_TRBJ2-7*_CASSIRSSYEQYF | 1. | TRB19*_TRBJ2-7*-CASSIRSSYEQYF |
| 2. | TRBV4-3*,TRBV4-2*_TRBJ2-1*_CASSLLSYNEQFF | 2. | TRBV4-3*,TRBV4-2*_TRBJ2-1*_CASSLLSYNEQFF |
| 3. | TRBV20-1*_TRBJ2-7_CSAPRTSGGLLNPYEQYF | 3. | TRBV20-1*_TRBJ2-7*_CSAPRTSGGLLNPYEQYF |
| 4. | TRBV7-9*_TRBJ2-7*_CASSSQEAGGRYNSYEQYF | 4. | TRBV5-1*_TRBJ2-7*_CASSLEGQASSYEQYF |
| 5. | TRBV7-8*_TRBJ2-5*_CASSLKRDGQETQYF | 5. | TRBV7-8*_TRBJ2-5*_CASSLKRDGQETQYF |
| 6. | TRBV5-1*_TRBJ2-7*_CASSLEGQASSYEQYF | 6. | TRBV7-9*_TRBJ2-7*_CASSSEIGTAGTSHNRQYF |
| 7. | TRBV3-1*, TRBV3-2*_TRBJ2-3*_CASSLGTDTQYF | 7. | TRBV7-2*_TRBJ2-2*_CASSLGVGTGELFF |
| 8. | TRBV7-2*_TRBJ2-2*_CASSLGVGTGELFF | 8. | **TRBV3-1*, TRBV3-2*_TRBJ2-3*_CASSLGTDTQYF** |
| 9. | TRBV7-9*_TRBJ2-7*_CASSSEIGTAGTSHNRQYF | 9. | **TRBV28*_TRBJ2-7*_CASSLDRNEQYF** |
| 10 | TRBV19*_TRBJ2-7*_CASSVRSSYEQYF | 10 | **TRBV19*_TRBJ2-7*_CASSVRSSYEQYF** |

| TRB-Top10-Non-Dedup | TRB-Top10-Non-Dedup |
|---|---|

| Clone Rank | Clone | Clone Rank | Clone |
|---|---|---|---|
| 1. | TRGV9*_TRGJ2*, TRGJ1*_CALWEVPHYYKKLF | 1. | TRGV9*_TRGJ2*, TRGJ1*_CALWEVPHYYKKLF |
| 2. | TRGV4*_TRGJ2*, TRGJ1*_CADQPQAYKKLF | 2. | TRGV4*_TRGJ2*, TRGJ1*_CADQPQAYKKLF |
| 3. | TRGV9*_TRGJP1*_CALWDETGWFKIF | 3. | TRGV9*_TRGJP1*_CALWDETGWFKIF |
| 4. | TRGV11*_TRGJP1*-CACWIRHVRATGWFKIF | 4. | TRGV11*_TRGJP1*_CACWIRHVRATGWFKIF |
| 5. | TRGV5*,TRGV3*_TRGJ2*,TRGJ1*_CATWDREKLF | 5. | TRGV5*,TRGV3*_TRGJ2*,TRGJ1*_CATWDREKLF |
| 6. | TRGV3*,TRGV5*_,TRGJ2*,TRGJ1*_CATWDNPYYKKLF | 6. | TRGV3*,TRGV5*_,TRGJ2*,TRGJ1*_CATWDNPYYKKLF |
| 7. | TRGV3*,TRGV5*,TRGJ2*,TRGJ1*_CATWDSLYYKKLF | 7. | TRGV3*,TRGV5*,TRGJ2*,TRGJ1*_CATWDSLYYKKLF |
| 8. | TRGV9*_TRGJP1*_CALWEVLTLSRTTGWFKIF | 8. | TRGV4*_TRGJ2*,TRGJ1*_CATCLYYKKLF |
| 9. | TRGV10*_TRGJP1*CAAHTTGWFKIF | 9. | TRGV9*_TRGJP1*_CALWEVLTLSRTTGWFKIF |
| 10 | TRGV4*_TRGJ2*,TRGJ1*_CATCLYYKKLF | 10 | TRGV10*_TRGJP1*CAAHTTGWFKIF |

Example 2: Experimental Protocol—RNA or mRNA Based Immuno-PETE

A modification of the immuno-PETE assay (e.g., as set forth in Example 1) is provided for starting material comprising total RNA or purified mRNA. Total RNA or purified mRNA can be obtained from whole blood, PBMC, sorted lymphocytes, lymphocyte culture, fresh or fresh-frozen tumor tissue, FFPE tissue samples, and the like. A schematic outlining an exemplary method for RNA or mRNA based immuno-PETE is set forth in FIG. 4. Briefly, a cDNA synthesis step is introduced prior to the immuno-PETE method essentially set forth in Example 1.

Here, an oligo-dT primer, set of random primers (e.g., hexamers, heptamers, octamers or nanomers, etc.,) or one or more C-segment primers (e.g., comprising one or more C-segment primers selected from SEQ ID NOS:205-213; see Table 8) is added to an aliquot of total RNA or purified mRNA to form a reaction mixture. A reverse transcriptase (e.g., SuperScript III™) and amplification components (such as buffers, dNTPs and salts (e.g., MgCl$_2$)) is added to the reaction mixture to initiate first and second strand synthesis to form double-stranded cDNA molecules. The cDNA molecules can be purified, for example using SPRI beads, and quantified for later use. The purified cDNA is then used as a starting template for the Immuno-PETE protocol set forth in Example 1. For example, purified cDNA is used as a starting template and a V gene specific probe set (e.g., comprising SEQ ID NOS:1-121) is used in the first round of extension (gPE primer pool), followed by second round of extension using the C-segment probe set (PE2 primer pool, e.g., comprising SEQ ID NOS:205-213). Alternatively, the first round of extension can include use of the C-segment gPE primers, followed by a second round of extension using the plurality of V gene specific PE2 primers (e.g., comprising SEQ ID NOS:122-204).

Several advantages are achieved through the application of a cDNA synthesis step to the immuno-PETE assay (e.g., as described in Example 1) including (1) improved assay sensitivity (more copies of immune receptor mRNA exist in immune cells as compared to the single copy of somatically rearranged V(D)J locus in genomic DNA); (2) decrease in amplification bias (use of fewer C-segment primers/probes as compared to J-segment primers/probes in the immuno-PETE protocol of Example 1); (3) identification of immune receptor isotypes (resulting amplions from the RNA or mRNA based Immuno-PETE assay span the V(D)J immune receptor domain. For TCR, there are α-1, β-1 and β-2 constant genes. For immunoglobulins, the distinguishable isotypes are κ and λ for light chains, and IgA, IgD, IgG, and IgM for the heavy chains). As such, the total RNA and/or mRNA based immuno-PETE assay is advantageous for high-throughput sequencing and/or immune repertoire profiling.

TABLE 8

| Sequence ID | Sequence name | Sequence 5'->3' |
|---|---|---|
| 205 | IgM | GATGGAGTCGGGAAGGAAGTCCTGTGCGAG |
| 206 | IgG | GGGAAGACSGATGGGCCCTTGGTGG |
| 207 | IgA | CAGGCAKGCGAYGACCACGTTCCCATC |
| 208 | IgD | CCACAGGGCTGTTATCCTTT |
| 209 | IgE | AGGGAATGTTTTTGCAGCAG |
| 210 | Igκ | CATCAGATGGCGGGAAGATGAAGACAGATGGTGC |
| 211 | Igλ | CCTCAGAGGAGGGTGGGAACAGAGTGAC |
| 212 | TCRB | GCTCAAACACAGCGACCTCGGGTGGGAACAC |
| 213 | TCRA | TCTCTCAGCTGGTACACGGCAGGGTCAGGG |

Example 3: Combined Immuno-PETE and Oncology Targets Panel

In immuno-oncology applications, it would be advantageous to profile both the somatic mutations in a tumor cell genome and the clonotype repertoire of tumor infiltrating T-cells, using a sample of tumor tissue (e.g., tumor biopsy or FFPE tumor tissue). Designing and optimizing such an assay by repeated design of multiple opposing (forward and reverse) multiplex-PCR primers is not practical. However, Immuno-PETE minimizes probe-probe (or primer-primer) interactions by using a design algorithm that separately designs gPE probe sets and PE2 probe sets to minimize primer dimers. The design algorithm can also place primers on +/−strands of genomic DNA such that primers are not pointed toward each other in the same reaction step, to prevent production of a shorter target. A further feature of the immuno-PETE assay is that each of the two probe hybridization and extension steps of the assay occur in separate (distinct) reactions after removal of residual probes from the previous step. Here, we demonstrate the immuno-PETE assay efficiently targets cancer genes and T-cell receptors in a combined assay, without prior optimization of the combined probe set, where there was no overlap or probe coordinates between the Oncology and TCR gene targets.

Experimental Design:

In order to demonstrate the utility of enriching both tumor cell genome targets and the somatically rearranged TCR targets from immune cells, we combined an oncology panel (Signature or "Sig" panel) containing 181 target regions from 21 cancer genes with a panel of V (n=60) and J (n=13) gene probes targeting TCRB. Specifically, SEQ ID NOS:1-60 were used as the V-gene probes and SEQ ID NOS:188-200 were used as the J-gene probes. Each of the panels was tested independently, but no attempts were made to optimize the combined probe set, all probes were used at equimolar concentrations.

Protocol:

Human genomic DNA (Promega Cat #G1471) was used as an input at 100 ng or 450 ng per reaction. This DNA sample is a mixture from multiple donors; it is not expected to contain oncology relevant somatic mutations, and assuming it has been isolated from PBMC, it contains T-cell genomic DNA. TCRB repertoire is expected to be very diverse due to the pooled nature of the DNA sample. Reaction mixtures were prepared and incubated as set forth in Table 9.

TABLE 9

| Qiagen Multiplex Taq and Phusion HS2 MM (16 + 1 samples) | |
|---|---|
| Reagent | Vol (ul) |
| Water | 1.5 |
| 2× (Taq or Phusion) Master Mix | 12.5 |
| gPE Mix Signature, +Fix, +TCRB | 1 |
| Sheared gDNA template (10 ng/ul, 45 ng/ul) | 10 |

Mix and place into thermal cycler
Run program <gPE Taq-Hyb Extend>
Remove tubes from the thermal cycler
Add 1 ul of Exonuclease I to the sample and mix
Place into thermal cycler
Run program <Exonuclease & Heat Kill>
Remove tubes from the thermal cycler
Prepare ligation master mix

| Ligation Master Mix (6 + 1 samples) | |
|---|---|
| Reagent | Vol (ul) |
| 2× ligase Buffer | 25 |
| T7 DNA ligase (30 U/μl) | 1 |

Add 25 ul to the sample and mix
Add 1 uL of barcoded adapter to each sample
Place into thermal cycler
Run program <Ligation>
Prepare KapaPure Reagent for ligation Cleanup

| KapaPure Reagent for Ligation Cleanup (6 + 1 samples) | |
|---|---|
| Reagent | Vol (ul) |
| KapaPure or Am pure | 70 |
| H2O | 50 |

Remove tubes from the thermal cycler
Add 120 uL KapaPure Reagent for Ligation Cleanup to the sample
Completely mix by vortexing or pipetting
Pop spin tubes to get oil droplets off of tube cap
Incubate at room temperature for at least 2 minutes
Place on magnet until beads are completely on sidewall
Completely remove supernatant and discard
Wash 2 times with 180 uL of 85% ethanol
Completely remove ethanol and dry pellet for 5 minutes
Resuspend m 10 uL of 10 mM Tris pH 8.0
Prepare PE2 Reagent Mix

| PE2 Reagent Mix (6 + 1 samples) | |
|---|---|
| Reagent | Vol (ul) |
| Phusion HF Mix (2×) | 25 |
| XC7/LP5-8 10 uM each | 2 |
| Ammonium sulfate (200 mM) | 5 |
| ETSSB | 1 |
| PE2 primer mix 12 uM | 1 |
| Betaine 5M | 6 |
| Sample | 10 |

Place into thermal cycler
Run program <PE2_PETE-CR>

| gPE Tag-Hyb Extend SOP | | |
|---|---|---|
| Step | Temperature | Time |
| Initial Denaturation | 95° C. | 5 min |
| Annealing | 54° C. | 30 minutes |

TABLE 9-continued

| Extension | 68° C. | 2 min |
| End | 4° C. | Hold (∞) |

| Exonuclease & Heat Kill | | |
| --- | --- | --- |
| Step | Temperature | Time |
| Exonuclease | 37° C. | 10 min |
| Heat Kill | 75° C. | 10 min |
| End | 4° C. | Hold (∞) |

| PE2 PETE-CR SubCyc 55-65 | | | |
| --- | --- | --- | --- |
| Step | Temperature | Time | |
| Initial Denaturation | 98° C. | 1 min | |
| Denaturation | 98° C. | 10 sec | 5× |
| Annealing (ramp at 0.2° C./sec) | 55° C. | 30 sec | |
| Annealing low | 55° C. | 30 sec | 4× |
| Annealing high | 65° C. | 30 sec | |
| Extension | 72° C. | 30 sec | |
| Denaturation | 98° C. | 10 sec | n |
| Annealing | 64° C. | 15 sec | |
| Extension 72° C. | 72° C. | 30 sec | |
| Stop | 4 °C | Hold (∞) | | n = 20 cycles for 100 ng
n = 18 cycles for 450 ng

Figure 5:
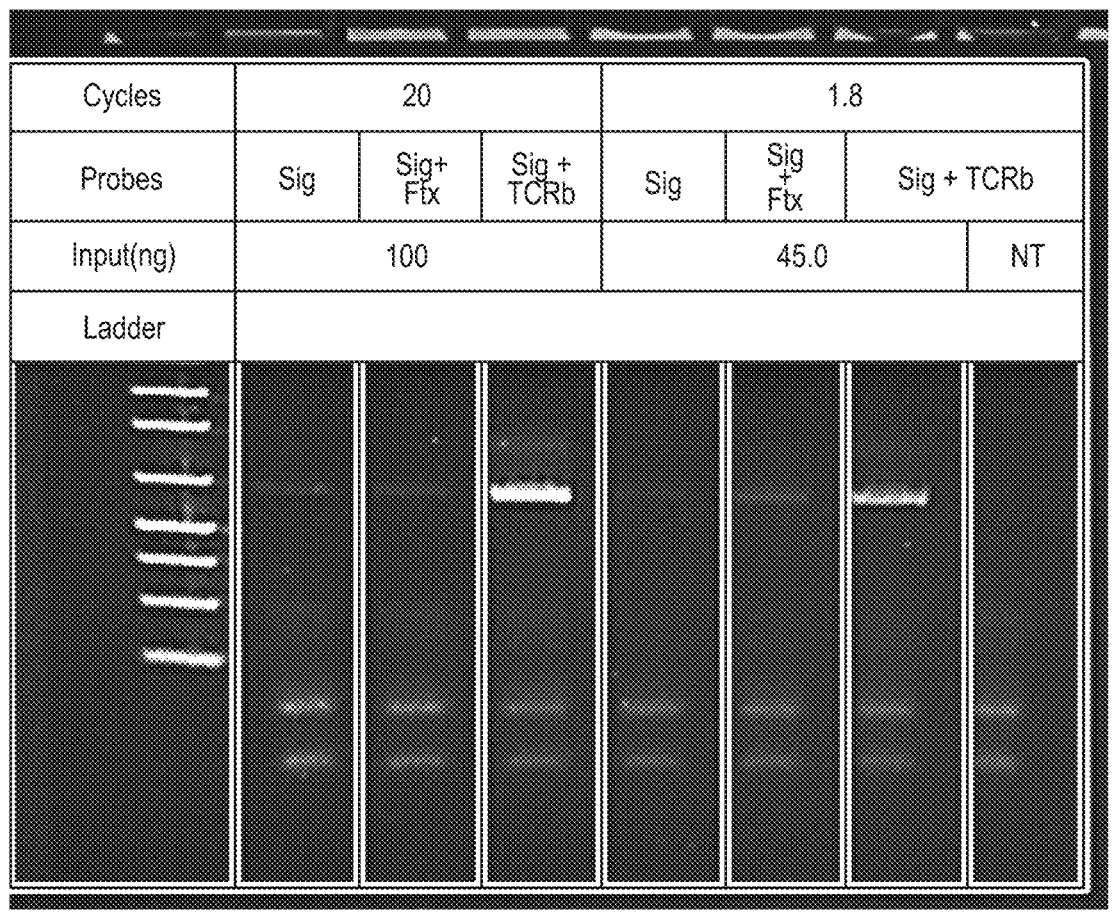
FIG. 5 is an image of exemplary primer extension products obtained by the immuno-PETE assay of Example 3 analyzed by agarose gel electrophoresis.

Results:

After completion of the immuno-PETE protocol set forth in Table 9, an aliquot of the reaction products from the 100 ng and 450 ng input gDNA was analyzed by agarose gel electrophoresis (FIG. 5). In FIG. 5, lanes 1-8 correspond as follows, lane 1: MW ladder; lanes 2,3: Oncology panel only, 100 ng gDNA; lanes 5, 6: Oncology panel only, 450 ng gDNA; lane 4: Oncology panel+TCRB, 10 ng gDNA; lane 7: Oncology panel+TCRB, 450 ng gDNA; lane 8: No Template (NT), negative control.

The enriched libraries were sequenced using Illumina MiSeq sequencer and Illumina MiSeq sequencing kit v3 using 2×300 cycles as per manufacturer's protocols.

Sequencing Analysis:

Analysis of oncology targets in the combined panel assay are provided in Table 10. A total of 543,000 read pairs for each of the 100 ng and 450 ng input gDNA was assessed. For the 450 ng gDNA sample a total of 153,138 unique pairs were identified. By comparison, 118,098 unique pairs were identified in the 100 ng gDNA sample. Additionally, analysis of the TCRB targets in the combined panel assay for each of the 100 ng or 450 ng input gDNA are summarized in Table 11.

TABLE 10

| Sample | Total input read pairs | Total read pairs after filtering | UNIQUE pairs | % Duplicate | Deduped trimmed reads mapped | % Deduped trimmed reads mapped | Dedup On-target reads | Dedup % On-target | PETE sw Mean UIDs per non-zero probe | Median target coverage | % bases >= 100× Coverage | Uniformity (0.5×-2× of mean) |
| --- | --- | --- | --- | --- | --- | --- | --- | --- | --- | --- | --- | --- |
| 450 ng-Sig-TCRb_S6_L00 | 543000 | 520443 | 153138 | 68.2 | 152217 | 29.2 | 138948 | 91.3 | 846.1 | 1367 | 99.9 | 81.2 |
| 100 ng-Sig-TCRb_S5_L00 | 543000 | 522924 | 118098 | 75.2 | 117291 | 22.4 | 101989 | 87 | 652.5 | 970 | 99.6 | 77.9 |

TABLE 11

(SEQ ID NO: 318-337)

| Sample | Total_input_read_pairs | Total_reads_pairs_after_filtering | %_input_reads_after_filtering | Unique_read_pairs | Duplicate_read_pairs | Unassigned_read_pairs | % Duplicate_Rate | Consensus_reads | TCRB_productive_unique_consensus_reads | d50 | Shannon_entropy |
| --- | --- | --- | --- | --- | --- | --- | --- | --- | --- | --- | --- |
| 100 ng-Sig-TCRb_S5_L001 | 3036337 | 2923802 | 96.3 | 748 | 8265 | 2912059 | 91.7 | 747 | 85 | 0.97619048 | 83.6249492 |

| Clone count | Clone fraction | AA. Seq. CDR3 |
| --- | --- | --- |
| 2 | 0.02352941 | CATSRGSPNYGYTF |
| 1 | 0.01176471 | CASSPGTSGSASSTDTQYF |
| 1 | 0.01176471 | CASSLALIVGGENTEAFF |
| 1 | 0.01176471 | CASSKGGTGGGWAGELFF |

TABLE 11-continued (SEQ ID NO: 318-337)

| Sample | Total_input_read_pairs | Total_reads_pairs_after_filtering | %_input_reads_after_filtering | Unique_read_pairs | Duplicate_read_pairs | Unassigned_read_pairs | % Duplicate Rate | Consensus_reads | TCRB_productive_unique_consensus_reads | d50 | Shannon_entropy |
|---|---|---|---|---|---|---|---|---|---|---|---|
| 1 | 0.01176471 | CASSQAFLPSLVTDTQYF | | | | | | | | | |
| 1 | 0.01176471 | CASSADTGTFMNTEAFF | | | | | | | | | |
| 1 | 0.01176471 | CASSLGERGALSETQYF | | | | | | | | | |
| 1 | 0.01176471 | CASSFSKNSRPYNEQFF | | | | | | | | | |
| 1 | 0.01176471 | CASSLGSRGQRLLEQYF | | | | | | | | | |
| 1 | 0.01176471 | CASSLVAGGFSYNEQFF | | | | | | | | | |
| 450 ng Sig · TCRb_S6_L001 | 1393309 | 1335599 | 95.9 | 580 | 2904 | 1330803 | 83.4 | 569 | 140 | 0.98550725 | 137.254685 |

| Clone count | Clone fraction | AA. Seq. CDR3 |
|---|---|---|
| 2 | 0.01428571 | CASSPGTGIDTQYF |
| 2 | 0.01428571 | CASSRQGNSPLHF |
| 1 | 0.00714286 | CASSQGRTRLQRGGRTDTQYF |
| 1 | 0.00714286 | CASSIGLAGALRDTGELFF |
| 1 | 0.00714286 | CASSLRGPGQGEGGSPLHF |
| 1 | 0.00714286 | CASSYPFPLTGGNQPQHF |
| 1 | 0.00714286 | CASSYAGTRLGNQPQHF |
| 1 | 0.00714286 | CASSLGLAGVRQETQYF |
| 1 | 0.00714286 | CASSLNRAFSGANVLTF |
| 1 | 0.00714286 | CASSEARSGPDTDTQYF |

Here, the data demonstrates the potential of immuno-PETE assays to sequence both oncology targets in the tumor cell genome and the clonotype repertoire of tumor infiltrating T-cells. The combined assay is a single tube reaction requiring as little as 100 ng DNA input, thus making it suitable for analysis of tumor tissue biopsies or FFPE tissue samples in immuno-oncology applications.

Immune-sequencing assays compatible with clinically relevant sample types, such as enriched T cell population or formalin fixed paraffin embedded tissue (FFPE) would provide valuable clinical utility.

Example 4 demonstrates Immuno-PETE, as described herein, in the context of FACS sorted T cells; while Example 5 demonstrates Immuno-PETE in the context of FFPE tissue cells.

Example 4: Immuno-PETE Using Antigen Positive FACS Sorted Human T-Cells

Experimental Design:

The amino acid sequences of CDR3 were determined for T cell receptor alpha and beta chains. Here, Immuno-PETE was performed essentially as set forth in Example 1 with DNA extracted from formalin fixed human T cells that were FACS sorted for M1 antigen (using 113 ng, 57 ng, or 11 ng DNA input; see Table 12 and FIG. 6).

Figure 6:
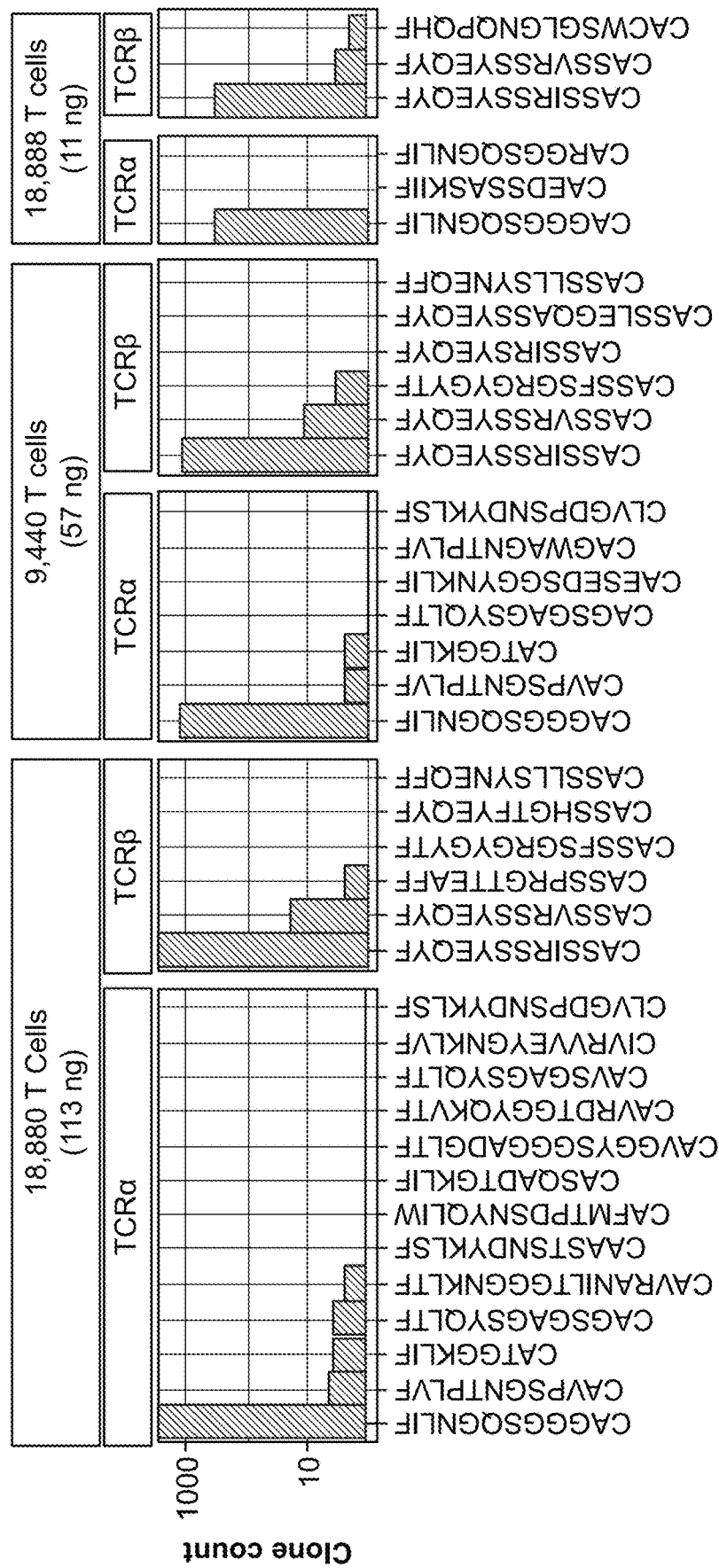
FIG. 6 is a graph showing clonotyping of T cell receptor alpha and beta chains using human FACS sorted T cells (SEQ ID NO: 274-311).

Results:

Clonotyping of T cell receptor alpha and beta chains was determined, see Table 12 and FIG. 6.

TABLE 12

| Sample type | | ng | T cell count * |
|---|---|---|---|
| FACS sorted | M1 specific T cells | 113 | 18,880 |
| | | 57 | 9,440 |
| | | 11 | 1,888 |
| FFPE | 90% Tumor 10% | 27 | 443 |
| | M1 specific T cells | 6 | 100 |

* 1 TCR template per 6 pg of DNA

Conclusion:

This example demonstrated the ability to predict T cell receptor alpha and beta CDR3 sequences at low input amounts in FACS sorted T cells. The T cell population was highly clonal as expected, and the most frequently observed CDR3 sequences were the same for all input amounts, for both alpha and beta chains.

Here, the immuno-PETE assay utilized at most 113 ng DNA input and as little as 11 ng DNA input, thus making it very suitable for analysis of tumor tissue biopsies or FFPE tissue samples in immuno-oncology applications.

Example 5: Immuno-PETE Using FFPE Tissue Sample

Figure 7:
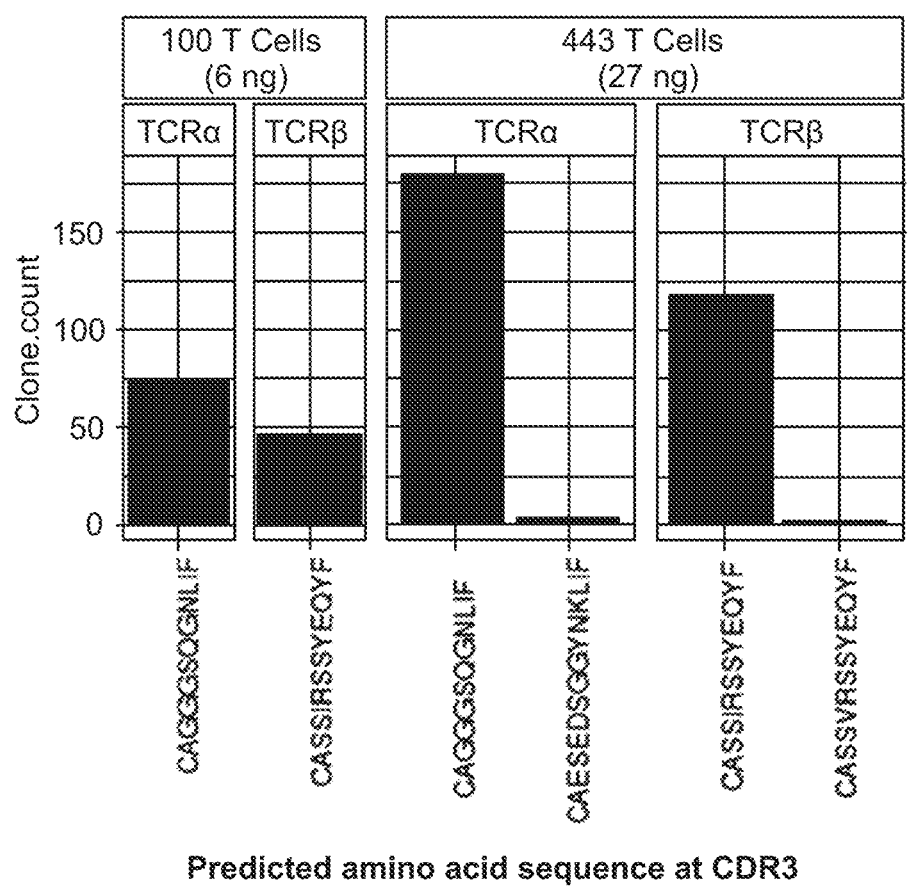
FIG. 7 is a graph showing clonotyping of T cell receptor alpha and beta chains using low DNA input amounts from FFPE tissue sample cells (SEQ ID NO:312-317).

Experimental Design:

As in Example 4, the amino acid sequences of CDR3 were determined for T cell receptor alpha and beta chains. Here, human T cells that were FACS sorted for M1 antigen were mixed with adenocarcinomic human alveolar basal epithelial cells (A549) at 1:9 ratio. Mixed cells were pelleted and fixed with formalin and embedded in paraffin (FFPE). DNA was extracted from the sectioned FFPE cell pellet, and Immuno-PETE was performed essentially according to Example 1 with either 6 ng or 27 ng DNA input. The DNA input amount was determined with qPCR (KAPA Human Genomic DNA Quantification and QC kit, Catalog Number 07960590001, Roche Diagnostics Corp., IN, USA).
Results:
Clonotyping of T cell receptor alpha and beta chains was determined, see Table 12 and FIG. 7.
Conclusion:
This Example demonstrates the ability to predict T cell receptor alpha and beta CDR3 sequences at low input amounts in FFPE tissue cells mixed with tumor cells (1:9 ratio). The T cell population was highly clonal as expected, and the most frequently observed CDR3 sequences were the same for both input amounts, for both alpha and beta chains.

Here, the immuno-PETE assay utilized less than 30 ng DNA input making it very suitable for analysis of tumor tissue biopsies or FFPE tissue samples in immuno-oncology applications.

What is claimed is:

1. A method for enriching from a sample a plurality of structurally different target polynucleotides, the method comprising:
   a) providing a reaction mixture comprising:
      i) a plurality of structurally different target polynucleotides, wherein individual target polynucleotides of the plurality comprise immune cell receptor V, J, and optionally C or D gene regions; and
      ii) a plurality of immune cell receptor V gene specific primers, wherein the immune cell receptor V gene specific primers comprise at least 10 structurally distinct primers having the following regions from 5' to 3': [SPLINT], [BARCODE], and [FW], wherein:
         [SPLINT] comprises an adaptor hybridization site of 2-8 nucleotides in length;
         [BARCODE] comprises a barcode region of at least 6 nucleotides in length, wherein each nucleotide of the barcode region is independently selected from the group consisting of N and W; and
         [FW] of each immune cell receptor V gene specific primer comprises a structurally distinct region that specifically hybridizes to a framework 1, framework 2, or framework 3 region of an immune cell receptor V gene, wherein the immune cell receptor V gene specific primers are hybridized to the V gene regions of the target polynucleotides;
   b) extending the hybridized immune cell receptor V gene specific primers with a polymerase, and then removing un-extended immune cell receptor V gene specific primers, if present, wherein the extended immune cell receptor V gene specific primers comprise at least a portion of the immune cell receptor V region, optionally the immune cell receptor D region, at least a portion of the immune cell receptor C region, and at least a portion of the immune cell receptor J region;

c) hybridizing a first universal adaptor to the [SPLINT] adaptor hybridization site of the extended immune cell receptor V gene specific primers;

d) hybridizing a plurality of immune cell receptor J gene specific primers to the J region portions of the extended immune cell receptor V gene specific primers, wherein the immune cell receptor J gene specific primers comprise a 3' J gene hybridizing region and a 5' second universal adapter region or hybridizing a plurality of immune cell receptor C gene specific primers to the C region portions of the extended immune cell receptor V gene specific primers, wherein the immune cell receptor C gene specific primers comprise a 3' C gene hybridizing region and a 5' second universal adapter region; and e) extending the hybridized immune cell receptor J gene specific primers or C gene specific primers with a polymerase, thereby forming a plurality of structurally different double-stranded products, each comprising at least a portion of the immune cell receptor V region, optionally the immune cell receptor D region, and at least a portion of the immune cell receptor J region or C region flanked by a first and second universal adapter sequence.

2. The method of claim 1, wherein e) and f) are repeated 2 to 15 times by heating to denature double-stranded products, cooling to hybridize un-extended immune cell receptor J or C gene specific primers to the J region portions of the extended immune cell receptor V gene specific primers or the C region portions of the extended immune cell receptor V gene specific primers, and extending hybridized primers.

3. The method of claim 1, wherein the removing un-extended immune cell receptor V gene specific primers comprises digesting by single-stranded DNA exonuclease digestion.

4. The method of claim 1, wherein the method further comprises amplifying double-stranded products comprising first and second universal adapters by universal PCR.

5. The method of claim 1, wherein the method further comprises determining an isotype or clonotype of at least one of the plurality of structurally different double-stranded products or amplified double-stranded products.

6. The method of claim 1, wherein the [FW] of each immune cell receptor V gene specific primer specifically hybridizes to a framework 1, framework 2, or framework 3 region of a T cell receptor V gene.

7. The method of claim 1, wherein the plurality comprises at least 10 of the primers set forth in SEQ ID Nos:1-121.

8. The method of claim 1, wherein the [SPLINT] consists of 6 consecutive nucleotides.

9. The method of claim 1, wherein the [BARCODE] consists of thirteen consecutive nucleotides selected from the group consisting of N and W.

10. The method of claim 1, wherein the plurality comprises at least 50 of the primers set forth in SEQ ID NOs:1-121.

* * * * *

```
                           SEQUENCE LISTING

<160> NUMBER OF SEQ ID NOS: 337

<210> SEQ ID NO 1
   <211> LENGTH: 26
   <212> TYPE: DNA
   <213> ORGANISM: Artificial Sequence
   <220> FEATURE:
   <223> OTHER INFORMATION: Synthetic Construct

<400> SEQUENCE: 1
gaatgccctg acagctctcg cttata                                           26

<210> SEQ ID NO 2
   <211> LENGTH: 41
   <212> TYPE: DNA
   <213> ORGANISM: Artificial Sequence
   <220> FEATURE:
   <223> OTHER INFORMATION: Synthetic Construct

<400> SEQUENCE: 2
ctcagagaag tctgaaatat tcgatgatca attctcagtt g                          41

<210> SEQ ID NO 3
   <211> LENGTH: 34
   <212> TYPE: DNA
   <213> ORGANISM: Artificial Sequence
   <220> FEATURE:
   <223> OTHER INFORMATION: Synthetic Construct

<400> SEQUENCE: 3
ccaaatcgmt tctcacctaa atctccagac aaag                                  34

<210> SEQ ID NO 4
   <211> LENGTH: 26
   <212> TYPE: DNA
   <213> ORGANISM: Artificial Sequence
   <220> FEATURE:
   <223> OTHER INFORMATION: Synthetic Construct

<400> SEQUENCE: 4
cacctgactc tccagacaaa gctcat                                           26

<210> SEQ ID NO 5
   <211> LENGTH: 22
   <212> TYPE: DNA
   <213> ORGANISM: Artificial Sequence
   <220> FEATURE:
   <223> OTHER INFORMATION: Synthetic Construct

<400> SEQUENCE: 5
cctgaatgcc ccaacagctc tc                                               22

<210> SEQ ID NO 6
   <211> LENGTH: 24
   <212> TYPE: DNA
```

```
<213> ORGANISM: Artificial Sequence
<220> FEATURE:
<223> OTHER INFORMATION: Synthetic Construct

<400> SEQUENCE: 6
gattctcagg gcgccagttc tcta                                              24

<210> SEQ ID NO 7
<211> LENGTH: 31
<212> TYPE: DNA
<213> ORGANISM: Artificial Sequence
<220> FEATURE:
<223> OTHER INFORMATION: Synthetic Construct

<400> SEQUENCE: 7
cctaattgat tctcagctca ccacgtccat a                                      31

<210> SEQ ID NO 8
<211> LENGTH: 19
<212> TYPE: DNA
<213> ORGANISM: Artificial Sequence
<220> FEATURE:
<223> OTHER INFORMATION: Synthetic Construct

<400> SEQUENCE: 8
tcagggcgcc agttccatg                                                    19

<210> SEQ ID NO 9
<211> LENGTH: 29
<212> TYPE: DNA
<213> ORGANISM: Artificial Sequence
<220> FEATURE:
<223> OTHER INFORMATION: Synthetic Construct

<400> SEQUENCE: 9
tcctagattc tcaggtctcc agttccta                                          29

<210> SEQ ID NO 10
<211> LENGTH: 28
<212> TYPE: DNA
<213> ORGANISM: Artificial Sequence
<220> FEATURE:
<223> OTHER INFORMATION: Synthetic Construct

<400> SEQUENCE: 10
gaggaaactt ccctgatcga ttctcagc                                          28

<210> SEQ ID NO 11
<211> LENGTH: 27
<212> TYPE: DNA
<213> ORGANISM: Artificial Sequence
<220> FEATURE:
<223> OTHER INFORMATION: Synthetic Construct

<400> SEQUENCE: 11
caacttccct gatcgattct caggtca                                           27

<210> SEQ ID NO 12
<211> LENGTH: 30
<212> TYPE: DNA
<213> ORGANISM: Artificial Sequence
<220> FEATURE:
<223> OTHER INFORMATION: Synthetic Construct

<400> SEQUENCE: 12
aggaaacttc cctgatcaat tctcaggtca                                        30
```

<210> SEQ ID NO 13
<211> LENGTH: 29
<212> TYPE: DNA
<213> ORGANISM: Artificial Sequence
<220> FEATURE:
<223> OTHER INFORMATION: Synthetic Construct

<400> SEQUENCE: 13
ggaaacttcc ctcctagatt ttcaggtcg                              29

<210> SEQ ID NO 14
<211> LENGTH: 27
<212> TYPE: DNA
<213> ORGANISM: Artificial Sequence
<220> FEATURE:
<223> OTHER INFORMATION: Synthetic Construct

<400> SEQUENCE: 14
ccccaatggc tacaatgtct ccagatt                                27

<210> SEQ ID NO 15
<211> LENGTH: 23
<212> TYPE: DNA
<213> ORGANISM: Artificial Sequence
<220> FEATURE:
<223> OTHER INFORMATION: Synthetic Construct

<400> SEQUENCE: 15
ggagaggtcc ctgatggcta caa                                    23

<210> SEQ ID NO 16
<211> LENGTH: 28
<212> TYPE: DNA
<213> ORGANISM: Artificial Sequence
<220> FEATURE:
<223> OTHER INFORMATION: Synthetic Construct

<400> SEQUENCE: 16
tccctgatgg ttatagtgtc tccagagc                               28

<210> SEQ ID NO 17
<211> LENGTH: 27
<212> TYPE: DNA
<213> ORGANISM: Artificial Sequence
<220> FEATURE:
<223> OTHER INFORMATION: Synthetic Construct

<400> SEQUENCE: 17
ggagaagtcc ccaatggcta caatgtc                                27

<210> SEQ ID NO 18
<211> LENGTH: 26
<212> TYPE: DNA
<213> ORGANISM: Artificial Sequence
<220> FEATURE:
<223> OTHER INFORMATION: Synthetic Construct

<400> SEQUENCE: 18
aaaggagaag tcccgaatgg ctacaa                                 26

<210> SEQ ID NO 19
<211> LENGTH: 29
<212> TYPE: DNA
<213> ORGANISM: Artificial Sequence
<220> FEATURE:

<223> OTHER INFORMATION: Synthetic Construct

<400> SEQUENCE: 19
gttcccaatg gctacaatgt ctccagatc                                      29

<210> SEQ ID NO 20
<211> LENGTH: 32
<212> TYPE: DNA
<213> ORGANISM: Artificial Sequence
<220> FEATURE:
<223> OTHER INFORMATION: Synthetic Construct

<400> SEQUENCE: 20
gaagtcccca atggctacaa tgtctctaga tt                                  32

<210> SEQ ID NO 21
<211> LENGTH: 26
<212> TYPE: DNA
<213> ORGANISM: Artificial Sequence
<220> FEATURE:
<223> OTHER INFORMATION: Synthetic Construct

<400> SEQUENCE: 21
gagaagtccc cgatggctac aatgta                                         26

<210> SEQ ID NO 22
<211> LENGTH: 24
<212> TYPE: DNA
<213> ORGANISM: Artificial Sequence
<220> FEATURE:
<223> OTHER INFORMATION: Synthetic Construct

<400> SEQUENCE: 22
gtgatcggtt ctctgcacag aggt                                           24

<210> SEQ ID NO 23
<211> LENGTH: 23
<212> TYPE: DNA
<213> ORGANISM: Artificial Sequence
<220> FEATURE:
<223> OTHER INFORMATION: Synthetic Construct

<400> SEQUENCE: 23
cgcttctctg cagagaggac tgg                                            23

<210> SEQ ID NO 24
<211> LENGTH: 22
<212> TYPE: DNA
<213> ORGANISM: Artificial Sequence
<220> FEATURE:
<223> OTHER INFORMATION: Synthetic Construct

<400> SEQUENCE: 24
ggttctttgc agtcaggcct ga                                             22

<210> SEQ ID NO 25
<211> LENGTH: 22
<212> TYPE: DNA
<213> ORGANISM: Artificial Sequence
<220> FEATURE:
<223> OTHER INFORMATION: Synthetic Construct

<400> SEQUENCE: 25
cagtggtcgg ttctctgcag ag                                             22

```
<210> SEQ ID NO 26
<211> LENGTH: 29
<212> TYPE: DNA
<213> ORGANISM: Artificial Sequence
<220> FEATURE:
<223> OTHER INFORMATION: Synthetic Construct

<400> SEQUENCE: 26
gctcagtgat caattctcca cagagaggt                                    29

<210> SEQ ID NO 27
<211> LENGTH: 22
<212> TYPE: DNA
<213> ORGANISM: Artificial Sequence
<220> FEATURE:
<223> OTHER INFORMATION: Synthetic Construct

<400> SEQUENCE: 27
ttctctgcag agaggcctga gg                                           22

<210> SEQ ID NO 28
<211> LENGTH: 25
<212> TYPE: DNA
<213> ORGANISM: Artificial Sequence
<220> FEATURE:
<223> OTHER INFORMATION: Synthetic Construct

<400> SEQUENCE: 28
cccagtgatc gcttctttgc agaaa                                        25

<210> SEQ ID NO 29
<211> LENGTH: 23
<212> TYPE: DNA
<213> ORGANISM: Artificial Sequence
<220> FEATURE:
<223> OTHER INFORMATION: Synthetic Construct

<400> SEQUENCE: 29
ctgcagagag gcctaaggga tct                                          23

<210> SEQ ID NO 30
<211> LENGTH: 33
<212> TYPE: DNA
<213> ORGANISM: Artificial Sequence
<220> FEATURE:
<223> OTHER INFORMATION: Synthetic Construct

<400> SEQUENCE: 30
gaagggtaca atgtctctgg aaacaaactc aag                               33

<210> SEQ ID NO 31
<211> LENGTH: 31
<212> TYPE: DNA
<213> ORGANISM: Artificial Sequence
<220> FEATURE:
<223> OTHER INFORMATION: Synthetic Construct

<400> SEQUENCE: 31
ggggtactgt gtttcttgaa acaagcttga g                                 31

<210> SEQ ID NO 32
<211> LENGTH: 30
<212> TYPE: DNA
<213> ORGANISM: Artificial Sequence
<220> FEATURE:
<223> OTHER INFORMATION: Synthetic Construct
```

-continued

<400> SEQUENCE: 32
cagttccctg acttgcactc tgaactaaac                                    30

<210> SEQ ID NO 33
<211> LENGTH: 32
<212> TYPE: DNA
<213> ORGANISM: Artificial Sequence
<220> FEATURE:
<223> OTHER INFORMATION: Synthetic Construct

<400> SEQUENCE: 33
actaacaaag gagaagtctc agatggctac ag                                 32

<210> SEQ ID NO 34
<211> LENGTH: 27
<212> TYPE: DNA
<213> ORGANISM: Artificial Sequence
<220> FEATURE:
<223> OTHER INFORMATION: Synthetic Construct

<400> SEQUENCE: 34
agataaagga gaagtccccg atggcta                                       27

<210> SEQ ID NO 35
<211> LENGTH: 35
<212> TYPE: DNA
<213> ORGANISM: Artificial Sequence
<220> FEATURE:
<223> OTHER INFORMATION: Synthetic Construct

<400> SEQUENCE: 35
gatactgaca aaggagaagt ctcagatggc tatag                              35

<210> SEQ ID NO 36
<211> LENGTH: 29
<212> TYPE: DNA
<213> ORGANISM: Artificial Sequence
<220> FEATURE:
<223> OTHER INFORMATION: Synthetic Construct

<400> SEQUENCE: 36
ctaaggatcg attttctgca gagaggctc                                     29

<210> SEQ ID NO 37
<211> LENGTH: 27
<212> TYPE: DNA
<213> ORGANISM: Artificial Sequence
<220> FEATURE:
<223> OTHER INFORMATION: Synthetic Construct

<400> SEQUENCE: 37
ttgattctca gcacagatgc ctgatgt                                       27

<210> SEQ ID NO 38
<211> LENGTH: 24
<212> TYPE: DNA
<213> ORGANISM: Artificial Sequence
<220> FEATURE:
<223> OTHER INFORMATION: Synthetic Construct

<400> SEQUENCE: 38
attctcagct gagaggcctg atgg                                          24

<210> SEQ ID NO 39
<211> LENGTH: 30

```
<212> TYPE: DNA
<213> ORGANISM: Artificial Sequence
<220> FEATURE:
<223> OTHER INFORMATION: Synthetic Construct

<400> SEQUENCE: 39
ggatcgattc tcagctaaga tgcctaatgc                                         30

<210> SEQ ID NO 40
<211> LENGTH: 28
<212> TYPE: DNA
<213> ORGANISM: Artificial Sequence
<220> FEATURE:
<223> OTHER INFORMATION: Synthetic Construct

<400> SEQUENCE: 40
ctcagcagag atgcctgatg caacttta                                           28

<210> SEQ ID NO 41
<211> LENGTH: 29
<212> TYPE: DNA
<213> ORGANISM: Artificial Sequence
<220> FEATURE:
<223> OTHER INFORMATION: Synthetic Construct

<400> SEQUENCE: 41
ctgatcgatt ctcagctcaa cagttcagt                                          29

<210> SEQ ID NO 42
<211> LENGTH: 26
<212> TYPE: DNA
<213> ORGANISM: Artificial Sequence
<220> FEATURE:
<223> OTHER INFORMATION: Synthetic Construct

<400> SEQUENCE: 42
tagctgaaag gactggaggg acgtat                                             26

<210> SEQ ID NO 43
<211> LENGTH: 24
<212> TYPE: DNA
<213> ORGANISM: Artificial Sequence
<220> FEATURE:
<223> OTHER INFORMATION: Synthetic Construct

<400> SEQUENCE: 43
ccaggaggcc gaacacttct ttct                                               24

<210> SEQ ID NO 44
<211> LENGTH: 25
<212> TYPE: DNA
<213> ORGANISM: Artificial Sequence
<220> FEATURE:
<223> OTHER INFORMATION: Synthetic Construct

<400> SEQUENCE: 44
gctaagtgcc tcccaaattc accct                                              25

<210> SEQ ID NO 45
<211> LENGTH: 26
<212> TYPE: DNA
<213> ORGANISM: Artificial Sequence
<220> FEATURE:
<223> OTHER INFORMATION: Synthetic Construct

<400> SEQUENCE: 45
```

```
cacagctgaa agacctaacg gaacgt                                              26

<210> SEQ ID NO 46
<211> LENGTH: 24
<212> TYPE: DNA
<213> ORGANISM: Artificial Sequence
<220> FEATURE:
<223> OTHER INFORMATION: Synthetic Construct

<400> SEQUENCE: 46
ctgctgaatt tcccaaagag ggcc                                                24

<210> SEQ ID NO 47
<211> LENGTH: 20
<212> TYPE: DNA
<213> ORGANISM: Artificial Sequence
<220> FEATURE:
<223> OTHER INFORMATION: Synthetic Construct

<400> SEQUENCE: 47
agggtacagc gtctctcggg                                                     20

<210> SEQ ID NO 48
<211> LENGTH: 23
<212> TYPE: DNA
<213> ORGANISM: Artificial Sequence
<220> FEATURE:
<223> OTHER INFORMATION: Synthetic Construct

<400> SEQUENCE: 48
gcctgacctt gtccactctg aca                                                 23

<210> SEQ ID NO 49
<211> LENGTH: 27
<212> TYPE: DNA
<213> ORGANISM: Artificial Sequence
<220> FEATURE:
<223> OTHER INFORMATION: Synthetic Construct

<400> SEQUENCE: 49
atgagcgatt tttagcccaa tgctcca                                             27

<210> SEQ ID NO 50
<211> LENGTH: 24
<212> TYPE: DNA
<213> ORGANISM: Artificial Sequence
<220> FEATURE:
<223> OTHER INFORMATION: Synthetic Construct

<400> SEQUENCE: 50
tgaaggctac gtgtctgcca agag                                                24

<210> SEQ ID NO 51
<211> LENGTH: 24
<212> TYPE: DNA
<213> ORGANISM: Artificial Sequence
<220> FEATURE:
<223> OTHER INFORMATION: Synthetic Construct

<400> SEQUENCE: 51
ctcatctcaa tgccccaaga acgc                                                24

<210> SEQ ID NO 52
<211> LENGTH: 31
<212> TYPE: DNA
<213> ORGANISM: Artificial Sequence
```

```
<220> FEATURE:
<223> OTHER INFORMATION: Synthetic Construct

<400> SEQUENCE: 52
agatctctga tggatacagt gtctctcgac a                              31

<210> SEQ ID NO 53
<211> LENGTH: 34
<212> TYPE: DNA
<213> ORGANISM: Artificial Sequence
<220> FEATURE:
<223> OTHER INFORMATION: Synthetic Construct

<400> SEQUENCE: 53
agatctttcc tctgagtcaa cagtctccag aata                           34

<210> SEQ ID NO 54
<211> LENGTH: 35
<212> TYPE: DNA
<213> ORGANISM: Artificial Sequence
<220> FEATURE:
<223> OTHER INFORMATION: Synthetic Construct

<400> SEQUENCE: 54
cactgaaaaa ggagatatct ctgaggggta tcatg                          35

<210> SEQ ID NO 55
<211> LENGTH: 31
<212> TYPE: DNA
<213> ORGANISM: Artificial Sequence
<220> FEATURE:
<223> OTHER INFORMATION: Synthetic Construct

<400> SEQUENCE: 55
gttcctgaag ggtacaaagt ctctcgaaaa g                              31

<210> SEQ ID NO 56
<211> LENGTH: 27
<212> TYPE: DNA
<213> ORGANISM: Artificial Sequence
<220> FEATURE:
<223> OTHER INFORMATION: Synthetic Construct

<400> SEQUENCE: 56
ctgaggggta cagtgtctct agagaga                                   27

<210> SEQ ID NO 57
<211> LENGTH: 25
<212> TYPE: DNA
<213> ORGANISM: Artificial Sequence
<220> FEATURE:
<223> OTHER INFORMATION: Synthetic Construct

<400> SEQUENCE: 57
agccgcccaa acctaacatt ctcaa                                     25

<210> SEQ ID NO 58
<211> LENGTH: 18
<212> TYPE: DNA
<213> ORGANISM: Artificial Sequence
<220> FEATURE:
<223> OTHER INFORMATION: Synthetic Construct

<400> SEQUENCE: 58
cccaggaccg gcagttca                                             18
```

<210> SEQ ID NO 59
<211> LENGTH: 40
<212> TYPE: DNA
<213> ORGANISM: Artificial Sequence
<220> FEATURE:
<223> OTHER INFORMATION: Synthetic Construct

<400> SEQUENCE: 59
ttgattagag acatatccct attgaaaata tttcctggca              40

<210> SEQ ID NO 60
<211> LENGTH: 31
<212> TYPE: DNA
<213> ORGANISM: Artificial Sequence
<220> FEATURE:
<223> OTHER INFORMATION: Synthetic Construct

<400> SEQUENCE: 60
agatgccctg agtcagcata gtcattctaa c                       31

<210> SEQ ID NO 61
<211> LENGTH: 26
<212> TYPE: DNA
<213> ORGANISM: Artificial Sequence
<220> FEATURE:
<223> OTHER INFORMATION: Synthetic Construct

<400> SEQUENCE: 61
ggaggggaag gccccacagc gtcttc                             26

<210> SEQ ID NO 62
<211> LENGTH: 27
<212> TYPE: DNA
<213> ORGANISM: Artificial Sequence
<220> FEATURE:
<223> OTHER INFORMATION: Synthetic Construct

<400> SEQUENCE: 62
tgaagtcata cagttcctgg tgtccat                            27

<210> SEQ ID NO 63
<211> LENGTH: 28
<212> TYPE: DNA
<213> ORGANISM: Artificial Sequence
<220> FEATURE:
<223> OTHER INFORMATION: Synthetic Construct

<400> SEQUENCE: 63
ccaaatcagg ctttggagca cctgatct                           28

<210> SEQ ID NO 64
<211> LENGTH: 33
<212> TYPE: DNA
<213> ORGANISM: Artificial Sequence
<220> FEATURE:
<223> OTHER INFORMATION: Synthetic Construct

<400> SEQUENCE: 64
ccaaacaaag gcttagaata tttattacat gtc                     33

<210> SEQ ID NO 65
<211> LENGTH: 27
<212> TYPE: DNA
<213> ORGANISM: Artificial Sequence
<220> FEATURE:
<223> OTHER INFORMATION: Synthetic Construct

<400> SEQUENCE: 65
ccaggtccct gaggcactcc accagct                                            27

<210> SEQ ID NO 66
<211> LENGTH: 28
<212> TYPE: DNA
<213> ORGANISM: Artificial Sequence
<220> FEATURE:
<223> OTHER INFORMATION: Synthetic Construct

<400> SEQUENCE: 66
ctgaatctaa attatgagcc atctgaca                                           28

<210> SEQ ID NO 67
<211> LENGTH: 32
<212> TYPE: DNA
<213> ORGANISM: Artificial Sequence
<220> FEATURE:
<223> OTHER INFORMATION: Synthetic Construct

<400> SEQUENCE: 67
tcattcctta gtcgctctga tagttatggt ta                                      32

<210> SEQ ID NO 68
<211> LENGTH: 31
<212> TYPE: DNA
<213> ORGANISM: Artificial Sequence
<220> FEATURE:
<223> OTHER INFORMATION: Synthetic Construct

<400> SEQUENCE: 68
cattccttag tcggtctaaa gggtacagtt a                                       31

<210> SEQ ID NO 69
<211> LENGTH: 31
<212> TYPE: DNA
<213> ORGANISM: Artificial Sequence
<220> FEATURE:
<223> OTHER INFORMATION: Synthetic Construct

<400> SEQUENCE: 69
acaacatgac ctatgaacgg ttctcttcat c                                       31

<210> SEQ ID NO 70
<211> LENGTH: 31
<212> TYPE: DNA
<213> ORGANISM: Artificial Sequence
<220> FEATURE:
<223> OTHER INFORMATION: Synthetic Construct

<400> SEQUENCE: 70
ctgaatttaa caagagccaa acctccttcc a                                       31

<210> SEQ ID NO 71
<211> LENGTH: 25
<212> TYPE: DNA
<213> ORGANISM: Artificial Sequence
<220> FEATURE:
<223> OTHER INFORMATION: Synthetic Construct

<400> SEQUENCE: 71
ccgacagaaa gtccagcact ctgag                                              25

<210> SEQ ID NO 72

<211> LENGTH: 36
<212> TYPE: DNA
<213> ORGANISM: Artificial Sequence
<220> FEATURE:
<223> OTHER INFORMATION: Synthetic Construct

<400> SEQUENCE: 72
cactgttcta ttgaataaaa aggataaaca tctgtc          36

<210> SEQ ID NO 73
<211> LENGTH: 32
<212> TYPE: DNA
<213> ORGANISM: Artificial Sequence
<220> FEATURE:
<223> OTHER INFORMATION: Synthetic Construct

<400> SEQUENCE: 73
gtcacctttg ataccaccct taaacagagt tt          32

<210> SEQ ID NO 74
<211> LENGTH: 35
<212> TYPE: DNA
<213> ORGANISM: Artificial Sequence
<220> FEATURE:
<223> OTHER INFORMATION: Synthetic Construct

<400> SEQUENCE: 74
agactaaatg ctacattact gaagaatgga agcag          35

<210> SEQ ID NO 75
<211> LENGTH: 36
<212> TYPE: DNA
<213> ORGANISM: Artificial Sequence
<220> FEATURE:
<223> OTHER INFORMATION: Synthetic Construct

<400> SEQUENCE: 75
tgaggctgaa tttataaaga gtaaattctc ctttaa          36

<210> SEQ ID NO 76
<211> LENGTH: 32
<212> TYPE: DNA
<213> ORGANISM: Artificial Sequence
<220> FEATURE:
<223> OTHER INFORMATION: Synthetic Construct

<400> SEQUENCE: 76
gctgaattta agaagagtga aacctccttc ca          32

<210> SEQ ID NO 77
<211> LENGTH: 33
<212> TYPE: DNA
<213> ORGANISM: Artificial Sequence
<220> FEATURE:
<223> OTHER INFORMATION: Synthetic Construct

<400> SEQUENCE: 77
ggctgaattt aagaggagtc aatcttcctt caa          33

<210> SEQ ID NO 78
<211> LENGTH: 30
<212> TYPE: DNA
<213> ORGANISM: Artificial Sequence
<220> FEATURE:
<223> OTHER INFORMATION: Synthetic Construct

<400> SEQUENCE: 78
gacacttatc acttccccaa tcaatacccc    30

<210> SEQ ID NO 79
<211> LENGTH: 33
<212> TYPE: DNA
<213> ORGANISM: Artificial Sequence
<220> FEATURE:
<223> OTHER INFORMATION: Synthetic Construct

<400> SEQUENCE: 79
ggctgaattt aacaagagtc aaacttcctt cca    33

<210> SEQ ID NO 80
<211> LENGTH: 32
<212> TYPE: DNA
<213> ORGANISM: Artificial Sequence
<220> FEATURE:
<223> OTHER INFORMATION: Synthetic Construct

<400> SEQUENCE: 80
gctgaattta agaagagcga aacctccttc ta    32

<210> SEQ ID NO 81
<211> LENGTH: 31
<212> TYPE: DNA
<213> ORGANISM: Artificial Sequence
<220> FEATURE:
<223> OTHER INFORMATION: Synthetic Construct

<400> SEQUENCE: 81
ccatgtaccg taaagaaacc acttctttcc a    31

<210> SEQ ID NO 82
<211> LENGTH: 31
<212> TYPE: DNA
<213> ORGANISM: Artificial Sequence
<220> FEATURE:
<223> OTHER INFORMATION: Synthetic Construct

<400> SEQUENCE: 82
ccacataccg taaagaaacc acttctttcc a    31

<210> SEQ ID NO 83
<211> LENGTH: 25
<212> TYPE: DNA
<213> ORGANISM: Artificial Sequence
<220> FEATURE:
<223> OTHER INFORMATION: Synthetic Construct

<400> SEQUENCE: 83
tggatgcaga cacaaagcaa agctc    25

<210> SEQ ID NO 84
<211> LENGTH: 36
<212> TYPE: DNA
<213> ORGANISM: Artificial Sequence
<220> FEATURE:
<223> OTHER INFORMATION: Synthetic Construct

<400> SEQUENCE: 84
taaagaactg cttggaaaag aaaaattta tagtgt    36

<210> SEQ ID NO 85
<211> LENGTH: 30
<212> TYPE: DNA

<210> SEQ ID NO 86
<211> LENGTH: 29
<212> TYPE: DNA
<213> ORGANISM: Artificial Sequence
<220> FEATURE:
<223> OTHER INFORMATION: Synthetic Construct

<400> SEQUENCE: 85
acagctcaat agagccagcc agtatatttc					30

<210> SEQ ID NO 86
<211> LENGTH: 29
<212> TYPE: DNA
<213> ORGANISM: Artificial Sequence
<220> FEATURE:
<223> OTHER INFORMATION: Synthetic Construct

<400> SEQUENCE: 86
cagctcaata agccagcca gtatgtttc					29

<210> SEQ ID NO 87
<211> LENGTH: 32
<212> TYPE: DNA
<213> ORGANISM: Artificial Sequence
<220> FEATURE:
<223> OTHER INFORMATION: Synthetic Construct

<400> SEQUENCE: 87
gcacaggtcg ataaatccag caagtatatc tc					32

<210> SEQ ID NO 88
<211> LENGTH: 34
<212> TYPE: DNA
<213> ORGANISM: Artificial Sequence
<220> FEATURE:
<223> OTHER INFORMATION: Synthetic Construct

<400> SEQUENCE: 88
ctgttacatt gaacaagaca gccaaacatt tctc					34

<210> SEQ ID NO 89
<211> LENGTH: 36
<212> TYPE: DNA
<213> ORGANISM: Artificial Sequence
<220> FEATURE:
<223> OTHER INFORMATION: Synthetic Construct

<400> SEQUENCE: 89
caccgtttta ttgaataaga cagtgaaaca tctctc					36

<210> SEQ ID NO 90
<211> LENGTH: 24
<212> TYPE: DNA
<213> ORGANISM: Artificial Sequence
<220> FEATURE:
<223> OTHER INFORMATION: Synthetic Construct

<400> SEQUENCE: 90
ccagaaggca agaaaatccg ccaa					24

<210> SEQ ID NO 91
<211> LENGTH: 33
<212> TYPE: DNA
<213> ORGANISM: Artificial Sequence
<220> FEATURE:
<223> OTHER INFORMATION: Synthetic Construct

<400> SEQUENCE: 91
agaagcgctt ggaaaagaga agttttatag tgt					33

<210> SEQ ID NO 92
<211> LENGTH: 30
<212> TYPE: DNA
<213> ORGANISM: Artificial Sequence
<220> FEATURE:
<223> OTHER INFORMATION: Synthetic Construct

<400> SEQUENCE: 92
tgaccttaac aaaggcgaga catctttcca                                    30

<210> SEQ ID NO 93
<211> LENGTH: 28
<212> TYPE: DNA
<213> ORGANISM: Artificial Sequence
<220> FEATURE:
<223> OTHER INFORMATION: Synthetic Construct

<400> SEQUENCE: 93
cgcttgacac ttccaagaaa agcagttc                                      28

<210> SEQ ID NO 94
<211> LENGTH: 30
<212> TYPE: DNA
<213> ORGANISM: Artificial Sequence
<220> FEATURE:
<223> OTHER INFORMATION: Synthetic Construct

<400> SEQUENCE: 94
cagtcctatc aagagtgaca gttccttcca                                    30

<210> SEQ ID NO 95
<211> LENGTH: 30
<212> TYPE: DNA
<213> ORGANISM: Artificial Sequence
<220> FEATURE:
<223> OTHER INFORMATION: Synthetic Construct

<400> SEQUENCE: 95
gaacttccag aaatccacca gttccttcaa                                    30

<210> SEQ ID NO 96
<211> LENGTH: 33
<212> TYPE: DNA
<213> ORGANISM: Artificial Sequence
<220> FEATURE:
<223> OTHER INFORMATION: Synthetic Construct

<400> SEQUENCE: 96
gctaaaagcc acattaacaa agaaggaaag ctt                                33

<210> SEQ ID NO 97
<211> LENGTH: 30
<212> TYPE: DNA
<213> ORGANISM: Artificial Sequence
<220> FEATURE:
<223> OTHER INFORMATION: Synthetic Construct

<400> SEQUENCE: 97
ctcgctggat aaatcatcag gacgtagtac                                    30

<210> SEQ ID NO 98
<211> LENGTH: 22
<212> TYPE: DNA
<213> ORGANISM: Artificial Sequence
<220> FEATURE:

<223> OTHER INFORMATION: Synthetic Construct

<400> SEQUENCE: 98
tcgctacgga acgctacagc tt                                          22

<210> SEQ ID NO 99
<211> LENGTH: 30
<212> TYPE: DNA
<213> ORGANISM: Artificial Sequence
<220> FEATURE:
<223> OTHER INFORMATION: Synthetic Construct

<400> SEQUENCE: 99
ctccttcaat aaaagtgcca agcagttctc                                  30

<210> SEQ ID NO 100
<211> LENGTH: 30
<212> TYPE: DNA
<213> ORGANISM: Artificial Sequence
<220> FEATURE:
<223> OTHER INFORMATION: Synthetic Construct

<400> SEQUENCE: 100
cactcttaat accaaggagg gttacagcta                                  30

<210> SEQ ID NO 101
<211> LENGTH: 30
<212> TYPE: DNA
<213> ORGANISM: Artificial Sequence
<220> FEATURE:
<223> OTHER INFORMATION: Synthetic Construct

<400> SEQUENCE: 101
tcagtttgga gaagcaaaaa agaacagctc                                  30

<210> SEQ ID NO 102
<211> LENGTH: 30
<212> TYPE: DNA
<213> ORGANISM: Artificial Sequence
<220> FEATURE:
<223> OTHER INFORMATION: Synthetic Construct

<400> SEQUENCE: 102
gatcatcaca gaagacagaa agtccagcac                                  30

<210> SEQ ID NO 103
<211> LENGTH: 29
<212> TYPE: DNA
<213> ORGANISM: Artificial Sequence
<220> FEATURE:
<223> OTHER INFORMATION: Synthetic Construct

<400> SEQUENCE: 103
gcaatcgctg aagacagaaa gtccagtac                                   29

<210> SEQ ID NO 104
<211> LENGTH: 29
<212> TYPE: DNA
<213> ORGANISM: Artificial Sequence
<220> FEATURE:
<223> OTHER INFORMATION: Synthetic Construct

<400> SEQUENCE: 104
cagtttggtg atgcaagaaa ggacagttc                                   29

```
<210> SEQ ID NO 105
<211> LENGTH: 28
<212> TYPE: DNA
<213> ORGANISM: Artificial Sequence
<220> FEATURE:
<223> OTHER INFORMATION: Synthetic Construct

<400> SEQUENCE: 105
cagtcaaagc tgaggaactt tatggcca                                        28

<210> SEQ ID NO 106
<211> LENGTH: 30
<212> TYPE: DNA
<213> ORGANISM: Artificial Sequence
<220> FEATURE:
<223> OTHER INFORMATION: Synthetic Construct

<400> SEQUENCE: 106
cttcttaaac aaaagtgcca agcacctctc                                      30

<210> SEQ ID NO 107
<211> LENGTH: 34
<212> TYPE: DNA
<213> ORGANISM: Artificial Sequence
<220> FEATURE:
<223> OTHER INFORMATION: Synthetic Construct

<400> SEQUENCE: 107
ctgcttcatt taatgaaaaa aagcagcaaa gctc                                 34

<210> SEQ ID NO 108
<211> LENGTH: 36
<212> TYPE: DNA
<213> ORGANISM: Artificial Sequence
<220> FEATURE:
<223> OTHER INFORMATION: Synthetic Construct

<400> SEQUENCE: 108
ttctgtgagc ttccagaaaa caactaaaac tattca                               36

<210> SEQ ID NO 109
<211> LENGTH: 36
<212> TYPE: DNA
<213> ORGANISM: Artificial Sequence
<220> FEATURE:
<223> OTHER INFORMATION: Synthetic Construct

<400> SEQUENCE: 109
cactgtactg ttgaataaaa atgctaaaca tgtctc                               36

<210> SEQ ID NO 110
<211> LENGTH: 36
<212> TYPE: DNA
<213> ORGANISM: Artificial Sequence
<220> FEATURE:
<223> OTHER INFORMATION: Synthetic Construct

<400> SEQUENCE: 110
gcctgtgaac tttgaaaaaa agaaaaagtt catcaa                               36

<210> SEQ ID NO 111
<211> LENGTH: 31
<212> TYPE: DNA
<213> ORGANISM: Artificial Sequence
<220> FEATURE:
<223> OTHER INFORMATION: Synthetic Construct
```

```
<400> SEQUENCE: 111
ccaagttgga tgagaaaaag cagcaaagtt c                              31

<210> SEQ ID NO 112
<211> LENGTH: 30
<212> TYPE: DNA
<213> ORGANISM: Artificial Sequence
<220> FEATURE:
<223> OTHER INFORMATION: Synthetic Construct

<400> SEQUENCE: 112
tcagtttggt ataaccagaa aggacagctt                                30

<210> SEQ ID NO 113
<211> LENGTH: 36
<212> TYPE: DNA
<213> ORGANISM: Artificial Sequence
<220> FEATURE:
<223> OTHER INFORMATION: Synthetic Construct

<400> SEQUENCE: 113
aagtagcata ttagataaga aagaactttc cagcat                         36

<210> SEQ ID NO 114
<211> LENGTH: 30
<212> TYPE: DNA
<213> ORGANISM: Artificial Sequence
<220> FEATURE:
<223> OTHER INFORMATION: Synthetic Construct

<400> SEQUENCE: 114
caggcttaaa aaaggagacc agcacatttc                                30

<210> SEQ ID NO 115
<211> LENGTH: 27
<212> TYPE: DNA
<213> ORGANISM: Artificial Sequence
<220> FEATURE:
<223> OTHER INFORMATION: Synthetic Construct

<400> SEQUENCE: 115
cttccagaaa gcagccaaat ccttcag                                   27

<210> SEQ ID NO 116
<211> LENGTH: 24
<212> TYPE: DNA
<213> ORGANISM: Artificial Sequence
<220> FEATURE:
<223> OTHER INFORMATION: Synthetic Construct

<400> SEQUENCE: 116
tgataccaaa gcccgtctca gcac                                      24

<210> SEQ ID NO 117
<211> LENGTH: 31
<212> TYPE: DNA
<213> ORGANISM: Artificial Sequence
<220> FEATURE:
<223> OTHER INFORMATION: Synthetic Construct

<400> SEQUENCE: 117
gaggcggaaa tattaaagac aaaaactccc c                              31

<210> SEQ ID NO 118
<211> LENGTH: 31
```

<212> TYPE: DNA
<213> ORGANISM: Artificial Sequence
<220> FEATURE:
<223> OTHER INFORMATION: Synthetic Construct

<400> SEQUENCE: 118
ccacaataaa catacaggaa aagcacagct c                                      31

<210> SEQ ID NO 119
<211> LENGTH: 22
<212> TYPE: DNA
<213> ORGANISM: Artificial Sequence
<220> FEATURE:
<223> OTHER INFORMATION: Synthetic Construct

<400> SEQUENCE: 119
agaaagcagc gaaatccgtc gc                                                22

<210> SEQ ID NO 120
<211> LENGTH: 30
<212> TYPE: DNA
<213> ORGANISM: Artificial Sequence
<220> FEATURE:
<223> OTHER INFORMATION: Synthetic Construct

<400> SEQUENCE: 120
tgacattgat attgcaaaga acctggctgt                                        30

<210> SEQ ID NO 121
<211> LENGTH: 30
<212> TYPE: DNA
<213> ORGANISM: Artificial Sequence
<220> FEATURE:
<223> OTHER INFORMATION: Synthetic Construct

<400> SEQUENCE: 121
gaaacacatt ctgacccaga aagcctttca                                        30

<210> SEQ ID NO 122
<211> LENGTH: 83
<212> TYPE: DNA
<213> ORGANISM: Artificial Sequence
<220> FEATURE:
<223> OTHER INFORMATION: Synthetic Construct

<400> SEQUENCE: 122
aatgatacgg cgaccaccga gatctacact ctttccctac acgacgctct tccgatctgg       60
ggagaagtgg aaactctggt tcc                                               83

<210> SEQ ID NO 123
<211> LENGTH: 90
<212> TYPE: DNA
<213> ORGANISM: Artificial Sequence
<220> FEATURE:
<223> OTHER INFORMATION: Synthetic Construct

<400> SEQUENCE: 123
aatgatacgg cgaccaccga gatctacact ctttccctac acgacgctct tccgatctga       60
ctcaccagat ataatgaata catgggtccc                                        90

<210> SEQ ID NO 124
<211> LENGTH: 79
<212> TYPE: DNA
<213> ORGANISM: Artificial Sequence
<220> FEATURE:

<223> OTHER INFORMATION: Synthetic Construct

<400> SEQUENCE: 124
aatgatacgg cgaccaccga gatctacact ctttccctac acgacgctct tccgatctcc    60
ggatgctgag tctggtccc                                                  79

<210> SEQ ID NO 125
<211> LENGTH: 78
<212> TYPE: DNA
<213> ORGANISM: Artificial Sequence
<220> FEATURE:
<223> OTHER INFORMATION: Synthetic Construct

<400> SEQUENCE: 125
aatgatacgg cgaccaccga gatctacact ctttccctac acgacgctct tccgatcttg    60
tacagccagc ctggtccc                                                   78

<210> SEQ ID NO 126
<211> LENGTH: 84
<212> TYPE: DNA
<213> ORGANISM: Artificial Sequence
<220> FEATURE:
<223> OTHER INFORMATION: Synthetic Construct

<400> SEQUENCE: 126
aatgatacgg cgaccaccga gatctacact ctttccctac acgacgctct tccgatctct    60
tggttgcact tggagtcttg ttcc                                            84

<210> SEQ ID NO 127
<211> LENGTH: 84
<212> TYPE: DNA
<213> ORGANISM: Artificial Sequence
<220> FEATURE:
<223> OTHER INFORMATION: Synthetic Construct

<400> SEQUENCE: 127
aatgatacgg cgaccaccga gatctacact ctttccctac acgacgctct tccgatctca    60
cggatgaaca ataaggctgg ttcc                                            84

<210> SEQ ID NO 128
<211> LENGTH: 83
<212> TYPE: DNA
<213> ORGANISM: Artificial Sequence
<220> FEATURE:
<223> OTHER INFORMATION: Synthetic Construct

<400> SEQUENCE: 128
aatgatacgg cgaccaccga gatctacact ctttccctac acgacgctct tccgatcttt    60
ggtatgacca ccacttggtt ccc                                             83

<210> SEQ ID NO 129
<211> LENGTH: 79
<212> TYPE: DNA
<213> ORGANISM: Artificial Sequence
<220> FEATURE:
<223> OTHER INFORMATION: Synthetic Construct

<400> SEQUENCE: 129
aatgatacgg cgaccaccga gatctacact ctttccctac acgacgctct tccgatctac    60
tgaccagaag tcgggtgcc                                                  79

```
<210> SEQ ID NO 130
<211> LENGTH: 94
<212> TYPE: DNA
<213> ORGANISM: Artificial Sequence
<220> FEATURE:
<223> OTHER INFORMATION: Synthetic Construct

<400> SEQUENCE: 130
aatgatacgg cgaccaccga gatctacact ctttccctac acgacgctct tccgatctat    60
ggaacttact tgctttaaca aatagtcttg ttcc                                94

<210> SEQ ID NO 131
<211> LENGTH: 85
<212> TYPE: DNA
<213> ORGANISM: Artificial Sequence
<220> FEATURE:
<223> OTHER INFORMATION: Synthetic Construct

<400> SEQUENCE: 131
aatgatacgg cgaccaccga gatctacact ctttccctac acgacgctct tccgatctac    60
tgagttccac ttttagctga gtgcc                                          85

<210> SEQ ID NO 132
<211> LENGTH: 85
<212> TYPE: DNA
<213> ORGANISM: Artificial Sequence
<220> FEATURE:
<223> OTHER INFORMATION: Synthetic Construct

<400> SEQUENCE: 132
aatgatacgg cgaccaccga gatctacact ctttccctac acgacgctct tccgatctac    60
ctggagagac tagaagcata gtccc                                          85

<210> SEQ ID NO 133
<211> LENGTH: 79
<212> TYPE: DNA
<213> ORGANISM: Artificial Sequence
<220> FEATURE:
<223> OTHER INFORMATION: Synthetic Construct

<400> SEQUENCE: 133
aatgatacgg cgaccaccga gatctacact ctttccctac acgacgctct tccgatctcc    60
tgaccagcag tctggtccc                                                 79

<210> SEQ ID NO 134
<211> LENGTH: 84
<212> TYPE: DNA
<213> ORGANISM: Artificial Sequence
<220> FEATURE:
<223> OTHER INFORMATION: Synthetic Construct

<400> SEQUENCE: 134
aatgatacgg cgaccaccga gatctacact ctttccctac acgacgctct tccgatctct    60
tgggatgact tggagctttg ttcc                                           84

<210> SEQ ID NO 135
<211> LENGTH: 92
<212> TYPE: DNA
<213> ORGANISM: Artificial Sequence
<220> FEATURE:
<223> OTHER INFORMATION: Synthetic Construct

<400> SEQUENCE: 135
```

```
aatgatacgg cgaccaccga gatctacact ctttccctac acgacgctct tccgatctcc    60
tacttaccag gttttactga taatcttgtc cc                                  92

<210> SEQ ID NO 136
<211> LENGTH: 86
<212> TYPE: DNA
<213> ORGANISM: Artificial Sequence
<220> FEATURE:
<223> OTHER INFORMATION: Synthetic Construct

<400> SEQUENCE: 136
aatgatacgg cgaccaccga gatctacact ctttccctac acgacgctct tccgatctta    60
ctggaactca ctgataaggt ggttcc                                         86

<210> SEQ ID NO 137
<211> LENGTH: 85
<212> TYPE: DNA
<213> ORGANISM: Artificial Sequence
<220> FEATURE:
<223> OTHER INFORMATION: Synthetic Construct

<400> SEQUENCE: 137
aatgatacgg cgaccaccga gatctacact ctttccctac acgacgctct tccgatctct    60
ggaactcact gataaggtgg gttcc                                          85

<210> SEQ ID NO 138
<211> LENGTH: 90
<212> TYPE: DNA
<213> ORGANISM: Artificial Sequence
<220> FEATURE:
<223> OTHER INFORMATION: Synthetic Construct

<400> SEQUENCE: 138
aatgatacgg cgaccaccga gatctacact ctttccctac acgacgctct tccgatctta    60
cttactaaga tccacctta acatggttcc                                      90

<210> SEQ ID NO 139
<211> LENGTH: 85
<212> TYPE: DNA
<213> ORGANISM: Artificial Sequence
<220> FEATURE:
<223> OTHER INFORMATION: Synthetic Construct

<400> SEQUENCE: 139
aatgatacgg cgaccaccga gatctacact ctttccctac acgacgctct tccgatctac    60
ttggtttaac tagcaccctg gttcc                                          85

<210> SEQ ID NO 140
<211> LENGTH: 82
<212> TYPE: DNA
<213> ORGANISM: Artificial Sequence
<220> FEATURE:
<223> OTHER INFORMATION: Synthetic Construct

<400> SEQUENCE: 140
aatgatacgg cgaccaccga gatctacact ctttccctac acgacgctct tccgatctag    60
gccagacagt caactgagtt cc                                             82

<210> SEQ ID NO 141
<211> LENGTH: 92
<212> TYPE: DNA
<213> ORGANISM: Artificial Sequence
```

<220> FEATURE:
<223> OTHER INFORMATION: Synthetic Construct

<400> SEQUENCE: 141
aatgatacgg cgaccaccga gatctacact ctttccctac acgacgctct tccgatctct    60
cacttacttg gagtgacatt atgtttggat cc    92

<210> SEQ ID NO 142
<211> LENGTH: 90
<212> TYPE: DNA
<213> ORGANISM: Artificial Sequence
<220> FEATURE:
<223> OTHER INFORMATION: Synthetic Construct

<400> SEQUENCE: 142
aatgatacgg cgaccaccga gatctacact ctttccctac acgacgctct tccgatctta    60
cttacttgct cttacagtta ctgtggttcc    90

<210> SEQ ID NO 143
<211> LENGTH: 91
<212> TYPE: DNA
<213> ORGANISM: Artificial Sequence
<220> FEATURE:
<223> OTHER INFORMATION: Synthetic Construct

<400> SEQUENCE: 143
aatgatacgg cgaccaccga gatctacact ctttccctac acgacgctct tccgatctta    60
acttacttgg ttttacattg agtttggtcc c    91

<210> SEQ ID NO 144
<211> LENGTH: 86
<212> TYPE: DNA
<213> ORGANISM: Artificial Sequence
<220> FEATURE:
<223> OTHER INFORMATION: Synthetic Construct

<400> SEQUENCE: 144
aatgatacgg cgaccaccga gatctacact ctttccctac acgacgctct tccgatctta    60
ccaggtaaaa cagtcaattg tgtccc    86

<210> SEQ ID NO 145
<211> LENGTH: 85
<212> TYPE: DNA
<213> ORGANISM: Artificial Sequence
<220> FEATURE:
<223> OTHER INFORMATION: Synthetic Construct

<400> SEQUENCE: 145
aatgatacgg cgaccaccga gatctacact ctttccctac acgacgctct tccgatctac    60
tgggtttcac agataactcc gttcc    85

<210> SEQ ID NO 146
<211> LENGTH: 79
<212> TYPE: DNA
<213> ORGANISM: Artificial Sequence
<220> FEATURE:
<223> OTHER INFORMATION: Synthetic Construct

<400> SEQUENCE: 146
aatgatacgg cgaccaccga gatctacact ctttccctac acgacgctct tccgatctgg    60
tgaccacaac ctgggtccc    79

```
<210> SEQ ID NO 147
<211> LENGTH: 80
<212> TYPE: DNA
<213> ORGANISM: Artificial Sequence
<220> FEATURE:
<223> OTHER INFORMATION: Synthetic Construct

<400> SEQUENCE: 147
aatgatacgg cgaccaccga gatctacact ctttccctac acgacgctct tccgatctgc    60
ttgacaagca gccttgtccc                                                80

<210> SEQ ID NO 148
<211> LENGTH: 80
<212> TYPE: DNA
<213> ORGANISM: Artificial Sequence
<220> FEATURE:
<223> OTHER INFORMATION: Synthetic Construct

<400> SEQUENCE: 148
aatgatacgg cgaccaccga gatctacact ctttccctac acgacgctct tccgatctgc    60
agcacggaca atctggttcc                                                80

<210> SEQ ID NO 149
<211> LENGTH: 81
<212> TYPE: DNA
<213> ORGANISM: Artificial Sequence
<220> FEATURE:
<223> OTHER INFORMATION: Synthetic Construct

<400> SEQUENCE: 149
aatgatacgg cgaccaccga gatctacact ctttccctac acgacgctct tccgatctgg    60
cttcacagtg agcgtagtcc c                                              81

<210> SEQ ID NO 150
<211> LENGTH: 84
<212> TYPE: DNA
<213> ORGANISM: Artificial Sequence
<220> FEATURE:
<223> OTHER INFORMATION: Synthetic Construct

<400> SEQUENCE: 150
aatgatacgg cgaccaccga gatctacact ctttccctac acgacgctct tccgatctct    60
tggtatgacc gagagtttgg tccc                                           84

<210> SEQ ID NO 151
<211> LENGTH: 85
<212> TYPE: DNA
<213> ORGANISM: Artificial Sequence
<220> FEATURE:
<223> OTHER INFORMATION: Synthetic Construct

<400> SEQUENCE: 151
aatgatacgg cgaccaccga gatctacact ctttccctac acgacgctct tccgatctac    60
ttgcaatcac agaaagtctt gtgcc                                          85

<210> SEQ ID NO 152
<211> LENGTH: 84
<212> TYPE: DNA
<213> ORGANISM: Artificial Sequence
<220> FEATURE:
<223> OTHER INFORMATION: Synthetic Construct

<400> SEQUENCE: 152
```
aatgatacgg cgaccaccga gatctacact ctttccctac acgacgctct tccgatctct    60
ggggagaata tgaagtcgtg tccc    84

<210> SEQ ID NO 153
<211> LENGTH: 80
<212> TYPE: DNA
<213> ORGANISM: Artificial Sequence
<220> FEATURE:
<223> OTHER INFORMATION: Synthetic Construct

<400> SEQUENCE: 153
aatgatacgg cgaccaccga gatctacact ctttccctac acgacgctct tccgatctgc    60
ttcaccacca gctgagttcc    80

<210> SEQ ID NO 154
<211> LENGTH: 79
<212> TYPE: DNA
<213> ORGANISM: Artificial Sequence
<220> FEATURE:
<223> OTHER INFORMATION: Synthetic Construct

<400> SEQUENCE: 154
aatgatacgg cgaccaccga gatctacact ctttccctac acgacgctct tccgatctct    60
ggacagcaag cagagtgcc    79

<210> SEQ ID NO 155
<211> LENGTH: 90
<212> TYPE: DNA
<213> ORGANISM: Artificial Sequence
<220> FEATURE:
<223> OTHER INFORMATION: Synthetic Construct

<400> SEQUENCE: 155
aatgatacgg cgaccaccga gatctacact ctttccctac acgacgctct tccgatctga    60
cttacctggc tttataatta gcttggtccc    90

<210> SEQ ID NO 156
<211> LENGTH: 90
<212> TYPE: DNA
<213> ORGANISM: Artificial Sequence
<220> FEATURE:
<223> OTHER INFORMATION: Synthetic Construct

<400> SEQUENCE: 156
aatgatacgg cgaccaccga gatctacact ctttccctac acgacgctct tccgatctta    60
cttacttgga aagacttgta atctggtccc    90

<210> SEQ ID NO 157
<211> LENGTH: 88
<212> TYPE: DNA
<213> ORGANISM: Artificial Sequence
<220> FEATURE:
<223> OTHER INFORMATION: Synthetic Construct

<400> SEQUENCE: 157
aatgatacgg cgaccaccga gatctacact ctttccctac acgacgctct tccgatctct    60
tacgtggtaa aacaatcact tgagtgcc    88

<210> SEQ ID NO 158
<211> LENGTH: 83
<212> TYPE: DNA

<213> ORGANISM: Artificial Sequence
<220> FEATURE:
<223> OTHER INFORMATION: Synthetic Construct

<400> SEQUENCE: 158

```
aatgatacgg cgaccaccga gatctacact ctttccctac acgacgctct tccgatctgg    60
ggaataacgg tgagtctcgt tcc                                            83
```

<210> SEQ ID NO 159
<211> LENGTH: 89
<212> TYPE: DNA
<213> ORGANISM: Artificial Sequence
<220> FEATURE:
<223> OTHER INFORMATION: Synthetic Construct

<400> SEQUENCE: 159

```
aatgatacgg cgaccaccga gatctacact ctttccctac acgacgctct tccgatctcc    60
tacctggttt tacttggtaa agttgtccc                                      89
```

<210> SEQ ID NO 160
<211> LENGTH: 82
<212> TYPE: DNA
<213> ORGANISM: Artificial Sequence
<220> FEATURE:
<223> OTHER INFORMATION: Synthetic Construct

<400> SEQUENCE: 160

```
aatgatacgg cgaccaccga gatctacact ctttccctac acgacgctct tccgatctcg    60
gatttactgc caggcttgtt cc                                             82
```

<210> SEQ ID NO 161
<211> LENGTH: 84
<212> TYPE: DNA
<213> ORGANISM: Artificial Sequence
<220> FEATURE:
<223> OTHER INFORMATION: Synthetic Construct

<400> SEQUENCE: 161

```
aatgatacgg cgaccaccga gatctacact ctttccctac acgacgctct tccgatctcg    60
gggtttgacc attaaccttg ttcc                                           84
```

<210> SEQ ID NO 162
<211> LENGTH: 81
<212> TYPE: DNA
<213> ORGANISM: Artificial Sequence
<220> FEATURE:
<223> OTHER INFORMATION: Synthetic Construct

<400> SEQUENCE: 162

```
aatgatacgg cgaccaccga gatctacact ctttccctac acgacgctct tccgatctgc    60
taaaaccttc agcctggtgc c                                              81
```

<210> SEQ ID NO 163
<211> LENGTH: 78
<212> TYPE: DNA
<213> ORGANISM: Artificial Sequence
<220> FEATURE:
<223> OTHER INFORMATION: Synthetic Construct

<400> SEQUENCE: 163

```
aatgatacgg cgaccaccga gatctacact ctttccctac acgacgctct tccgatctgt    60
gaccaacagc gaggtgcc                                                  78
```

<210> SEQ ID NO 164
<211> LENGTH: 91
<212> TYPE: DNA
<213> ORGANISM: Artificial Sequence
<220> FEATURE:
<223> OTHER INFORMATION: Synthetic Construct

<400> SEQUENCE: 164
aatgatacgg cgaccaccga gatctacact ctttccctac acgacgctct tccgatctac    60
acttacttgg tttaacagag agtttagtgc c                                   91

<210> SEQ ID NO 165
<211> LENGTH: 85
<212> TYPE: DNA
<213> ORGANISM: Artificial Sequence
<220> FEATURE:
<223> OTHER INFORMATION: Synthetic Construct

<400> SEQUENCE: 165
aatgatacgg cgaccaccga gatctacact ctttccctac acgacgctct tccgatctac    60
ttggttttac tgtcagtctg gtccc                                          85

<210> SEQ ID NO 166
<211> LENGTH: 83
<212> TYPE: DNA
<213> ORGANISM: Artificial Sequence
<220> FEATURE:
<223> OTHER INFORMATION: Synthetic Construct

<400> SEQUENCE: 166
aatgatacgg cgaccaccga gatctacact ctttccctac acgacgctct tccgatctcg    60
agcgtgacct gaagtcttgt tcc                                            83

<210> SEQ ID NO 167
<211> LENGTH: 84
<212> TYPE: DNA
<213> ORGANISM: Artificial Sequence
<220> FEATURE:
<223> OTHER INFORMATION: Synthetic Construct

<400> SEQUENCE: 167
aatgatacgg cgaccaccga gatctacact ctttccctac acgacgctct tccgatctca    60
gggctggatg attagatgag tccc                                           84

<210> SEQ ID NO 168
<211> LENGTH: 82
<212> TYPE: DNA
<213> ORGANISM: Artificial Sequence
<220> FEATURE:
<223> OTHER INFORMATION: Synthetic Construct

<400> SEQUENCE: 168
aatgatacgg cgaccaccga gatctacact ctttccctac acgacgctct tccgatctgg    60
gcctaactgc taaacgagtc cc                                             82

<210> SEQ ID NO 169
<211> LENGTH: 86
<212> TYPE: DNA
<213> ORGANISM: Artificial Sequence
<220> FEATURE:
<223> OTHER INFORMATION: Synthetic Construct

<400> SEQUENCE: 169
aatgatacgg cgaccaccga gatctacact ctttccctac acgacgctct tccgatctca    60
caggacttga ctctcagaat ggttcc    86

<210> SEQ ID NO 170
<211> LENGTH: 85
<212> TYPE: DNA
<213> ORGANISM: Artificial Sequence
<220> FEATURE:
<223> OTHER INFORMATION: Synthetic Construct

<400> SEQUENCE: 170
aatgatacgg cgaccaccga gatctacact ctttccctac acgacgctct tccgatctac    60
tgggtatgat ggtgagtctt gttcc    85

<210> SEQ ID NO 171
<211> LENGTH: 84
<212> TYPE: DNA
<213> ORGANISM: Artificial Sequence
<220> FEATURE:
<223> OTHER INFORMATION: Synthetic Construct

<400> SEQUENCE: 171
aatgatacgg cgaccaccga gatctacact ctttccctac acgacgctct tccgatctct    60
tggaatgacc gtcaaacttg tccc    84

<210> SEQ ID NO 172
<211> LENGTH: 89
<212> TYPE: DNA
<213> ORGANISM: Artificial Sequence
<220> FEATURE:
<223> OTHER INFORMATION: Synthetic Construct

<400> SEQUENCE: 172
aatgatacgg cgaccaccga gatctacact ctttccctac acgacgctct tccgatctac    60
ttacttggaa tgactgataa gcttgtccc    89

<210> SEQ ID NO 173
<211> LENGTH: 86
<212> TYPE: DNA
<213> ORGANISM: Artificial Sequence
<220> FEATURE:
<223> OTHER INFORMATION: Synthetic Construct

<400> SEQUENCE: 173
aatgatacgg cgaccaccga gatctacact ctttccctac acgacgctct tccgatcttg    60
cttggcttca cagttagtca tgtctc    86

<210> SEQ ID NO 174
<211> LENGTH: 84
<212> TYPE: DNA
<213> ORGANISM: Artificial Sequence
<220> FEATURE:
<223> OTHER INFORMATION: Synthetic Construct

<400> SEQUENCE: 174
aatgatacgg cgaccaccga gatctacact ctttccctac acgacgctct tccgatctct    60
tggatggaca gtcaagatgg tccc    84

<210> SEQ ID NO 175
<211> LENGTH: 90

<212> TYPE: DNA
<213> ORGANISM: Artificial Sequence
<220> FEATURE:
<223> OTHER INFORMATION: Synthetic Construct

<400> SEQUENCE: 175
aatgatacgg cgaccaccga gatctacact ctttccctac acgacgctct tccgatctaa    60
cttacttgga ttcacggtta agagagttcc                                     90

<210> SEQ ID NO 176
<211> LENGTH: 83
<212> TYPE: DNA
<213> ORGANISM: Artificial Sequence
<220> FEATURE:
<223> OTHER INFORMATION: Synthetic Construct

<400> SEQUENCE: 176
aatgatacgg cgaccaccga gatctacact ctttccctac acgacgctct tccgatcttt    60
gggttgatag tcagcctggt tcc                                            83

<210> SEQ ID NO 177
<211> LENGTH: 94
<212> TYPE: DNA
<213> ORGANISM: Artificial Sequence
<220> FEATURE:
<223> OTHER INFORMATION: Synthetic Construct

<400> SEQUENCE: 177
aatgatacgg cgaccaccga gatctacact ctttccctac acgacgctct tccgatctcc    60
acacttactt ggatttattt ttgtactcat cccc                                94

<210> SEQ ID NO 178
<211> LENGTH: 93
<212> TYPE: DNA
<213> ORGANISM: Artificial Sequence
<220> FEATURE:
<223> OTHER INFORMATION: Synthetic Construct

<400> SEQUENCE: 178
aatgatacgg cgaccaccga gatctacact ctttccctac acgacgctct tccgatctta    60
aaacatacct ggtctaacac tcagagttat tcc                                 93

<210> SEQ ID NO 179
<211> LENGTH: 86
<212> TYPE: DNA
<213> ORGANISM: Artificial Sequence
<220> FEATURE:
<223> OTHER INFORMATION: Synthetic Construct

<400> SEQUENCE: 179
aatgatacgg cgaccaccga gatctacact ctttccctac acgacgctct tccgatctta    60
catgggttta ctgtcagttt cgttcc                                         86

<210> SEQ ID NO 180
<211> LENGTH: 84
<212> TYPE: DNA
<213> ORGANISM: Artificial Sequence
<220> FEATURE:
<223> OTHER INFORMATION: Synthetic Construct

<400> SEQUENCE: 180
aatgatacgg cgaccaccga gatctacact ctttccctac acgacgctct tccgatctcc    60
aggattcact gtgagctgtg ttcc                                                    84

<210> SEQ ID NO 181
<211> LENGTH: 81
<212> TYPE: DNA
<213> ORGANISM: Artificial Sequence
<220> FEATURE:
<223> OTHER INFORMATION: Synthetic Construct

<400> SEQUENCE: 181
aatgatacgg cgaccaccga gatctacact ctttccctac acgacgctct tccgatctag    60
cttcactctc acttgcgtcc c                                               81

<210> SEQ ID NO 182
<211> LENGTH: 84
<212> TYPE: DNA
<213> ORGANISM: Artificial Sequence
<220> FEATURE:
<223> OTHER INFORMATION: Synthetic Construct

<400> SEQUENCE: 182
aatgatacgg cgaccaccga gatctacact ctttccctac acgacgctct tccgatctcc    60
caggctcaca attaactcag tccc                                            84

<210> SEQ ID NO 183
<211> LENGTH: 90
<212> TYPE: DNA
<213> ORGANISM: Artificial Sequence
<220> FEATURE:
<223> OTHER INFORMATION: Synthetic Construct

<400> SEQUENCE: 183
aatgatacgg cgaccaccga gatctacact ctttccctac acgacgctct tccgatctta    60
cttgctgagt ttcatgattc ctctagtgtt                                      90

<210> SEQ ID NO 184
<211> LENGTH: 80
<212> TYPE: DNA
<213> ORGANISM: Artificial Sequence
<220> FEATURE:
<223> OTHER INFORMATION: Synthetic Construct

<400> SEQUENCE: 184
aatgatacgg cgaccaccga gatctacact ctttccctac acgacgctct tccgatctgt    60
tccacagtca cacgggttcc                                                 80

<210> SEQ ID NO 185
<211> LENGTH: 83
<212> TYPE: DNA
<213> ORGANISM: Artificial Sequence
<220> FEATURE:
<223> OTHER INFORMATION: Synthetic Construct

<400> SEQUENCE: 185
aatgatacgg cgaccaccga gatctacact ctttccctac acgacgctct tccgatctct    60
ggttccacga tgagttgtgt tcc                                             83

<210> SEQ ID NO 186
<211> LENGTH: 81
<212> TYPE: DNA
<213> ORGANISM: Artificial Sequence
<220> FEATURE:
<223> OTHER INFORMATION: Synthetic Construct

<400> SEQUENCE: 186
aatgatacgg cgaccaccga gatctacact ctttccctac acgacgctct tccgatctgg     60
ctccacgaag agtttgatgc c                                              81

<210> SEQ ID NO 187
<211> LENGTH: 88
<212> TYPE: DNA
<213> ORGANISM: Artificial Sequence
<220> FEATURE:
<223> OTHER INFORMATION: Synthetic Construct

<400> SEQUENCE: 187
aatgatacgg cgaccaccga gatctacact ctttccctac acgacgctct tccgatctct     60
tacgttgttg tacctccaga taggttcc                                       88

<210> SEQ ID NO 188
<211> LENGTH: 87
<212> TYPE: DNA
<213> ORGANISM: Artificial Sequence
<220> FEATURE:
<223> OTHER INFORMATION: Synthetic Construct

<400> SEQUENCE: 188
aatgatacgg cgaccaccga gatctacact ctttccctac acgacgctct tccgatctgt     60
cttacctaca actgtgagtc tggtgcc                                        87

<210> SEQ ID NO 189
<211> LENGTH: 86
<212> TYPE: DNA
<213> ORGANISM: Artificial Sequence
<220> FEATURE:
<223> OTHER INFORMATION: Synthetic Construct

<400> SEQUENCE: 189
aatgatacgg cgaccaccga gatctacact ctttccctac acgacgctct tccgatctcc     60
ttacctacaa cggttaacct ggtccc                                         86

<210> SEQ ID NO 190
<211> LENGTH: 89
<212> TYPE: DNA
<213> ORGANISM: Artificial Sequence
<220> FEATURE:
<223> OTHER INFORMATION: Synthetic Construct

<400> SEQUENCE: 190
aatgatacgg cgaccaccga gatctacact ctttccctac acgacgctct tccgatctct     60
tactcaccta caacagtgag ccaacttcc                                      89

<210> SEQ ID NO 191
<211> LENGTH: 84
<212> TYPE: DNA
<213> ORGANISM: Artificial Sequence
<220> FEATURE:
<223> OTHER INFORMATION: Synthetic Construct

<400> SEQUENCE: 191
aatgatacgg cgaccaccga gatctacact ctttccctac acgacgctct tccgatctat     60
acccaagaca gagagctggg ttcc                                           84

<210> SEQ ID NO 192

```
<211> LENGTH: 87
<212> TYPE: DNA
<213> ORGANISM: Artificial Sequence
<220> FEATURE:
<223> OTHER INFORMATION: Synthetic Construct

<400> SEQUENCE: 192
aatgatacgg cgaccaccga gatctacact ctttccctac acgacgctct tccgatctaa    60
cttacctagg atggagagtc gagtccc                                        87

<210> SEQ ID NO 193
<211> LENGTH: 80
<212> TYPE: DNA
<213> ORGANISM: Artificial Sequence
<220> FEATURE:
<223> OTHER INFORMATION: Synthetic Construct

<400> SEQUENCE: 193
aatgatacgg cgaccaccga gatctacact ctttccctac acgacgctct tccgatctct    60
gtcacagtga gcctggtccc                                                80

<210> SEQ ID NO 194
<211> LENGTH: 76
<212> TYPE: DNA
<213> ORGANISM: Artificial Sequence
<220> FEATURE:
<223> OTHER INFORMATION: Synthetic Construct

<400> SEQUENCE: 194
aatgatacgg cgaccaccga gatctacact ctttccctac acgacgctct tccgatctca    60
cggtgagccg tgtccc                                                    76

<210> SEQ ID NO 195
<211> LENGTH: 80
<212> TYPE: DNA
<213> ORGANISM: Artificial Sequence
<220> FEATURE:
<223> OTHER INFORMATION: Synthetic Construct

<400> SEQUENCE: 195
aatgatacgg cgaccaccga gatctacact ctttccctac acgacgctct tccgatctcc    60
agtacggtca gcctagagcc                                                80

<210> SEQ ID NO 196
<211> LENGTH: 76
<212> TYPE: DNA
<213> ORGANISM: Artificial Sequence
<220> FEATURE:
<223> OTHER INFORMATION: Synthetic Construct

<400> SEQUENCE: 196
aatgatacgg cgaccaccga gatctacact ctttccctac acgacgctct tccgatctca    60
ctgtcagccg ggtgcc                                                    76

<210> SEQ ID NO 197
<211> LENGTH: 76
<212> TYPE: DNA
<213> ORGANISM: Artificial Sequence
<220> FEATURE:
<223> OTHER INFORMATION: Synthetic Construct

<400> SEQUENCE: 197
aatgatacgg cgaccaccga gatctacact ctttccctac acgacgctct tccgatctca    60
```

```
ctgagagccg ggtccc                                              76

<210> SEQ ID NO 198
<211> LENGTH: 75
<212> TYPE: DNA
<213> ORGANISM: Artificial Sequence
<220> FEATURE:
<223> OTHER INFORMATION: Synthetic Construct

<400> SEQUENCE: 198
aatgatacgg cgaccaccga gatctacact ctttccctac acgacgctct tccgatctac   60
caggagccgc gtgcc                                              75

<210> SEQ ID NO 199
<211> LENGTH: 76
<212> TYPE: DNA
<213> ORGANISM: Artificial Sequence
<220> FEATURE:
<223> OTHER INFORMATION: Synthetic Construct

<400> SEQUENCE: 199
aatgatacgg cgaccaccga gatctacact ctttccctac acgacgctct tccgatctca   60
cggtcagcct gctgcc                                              76

<210> SEQ ID NO 200
<211> LENGTH: 76
<212> TYPE: DNA
<213> ORGANISM: Artificial Sequence
<220> FEATURE:
<223> OTHER INFORMATION: Synthetic Construct

<400> SEQUENCE: 200
aatgatacgg cgaccaccga gatctacact ctttccctac acgacgctct tccgatctga   60
ccgtgagcct ggtgcc                                              76

<210> SEQ ID NO 201
<211> LENGTH: 92
<212> TYPE: DNA
<213> ORGANISM: Artificial Sequence
<220> FEATURE:
<223> OTHER INFORMATION: Synthetic Construct

<400> SEQUENCE: 201
aatgatacgg cgaccaccga gatctacact ctttccctac acgacgctct tccgatctgt   60
gaagttacta tgagcttagt cccttcagca aa                              92

<210> SEQ ID NO 202
<211> LENGTH: 91
<212> TYPE: DNA
<213> ORGANISM: Artificial Sequence
<220> FEATURE:
<223> OTHER INFORMATION: Synthetic Construct

<400> SEQUENCE: 202
aatgatacgg cgaccaccga gatctacact ctttccctac acgacgctct tccgatctcg   60
aagttactat gagcctagtc ccttttgcaa a                              91

<210> SEQ ID NO 203
<211> LENGTH: 86
<212> TYPE: DNA
<213> ORGANISM: Artificial Sequence
<220> FEATURE:
```

```
<223> OTHER INFORMATION: Synthetic Construct

<400> SEQUENCE: 203
aatgatacgg cgaccaccga gatctacact ctttccctac acgacgctct tccgatcttg    60
acaacaagtg ttgttccact gccaaa                                        86

<210> SEQ ID NO 204
<211> LENGTH: 89
<212> TYPE: DNA
<213> ORGANISM: Artificial Sequence
<220> FEATURE:
<223> OTHER INFORMATION: Synthetic Construct

<400> SEQUENCE: 204
aatgatacgg cgaccaccga gatctacact ctttccctac acgacgctct tccgatctct    60
gtaatgataa gctttgttcc gggaccaaa                                     89

<210> SEQ ID NO 205
<211> LENGTH: 30
<212> TYPE: DNA
<213> ORGANISM: Artificial Sequence
<220> FEATURE:
<223> OTHER INFORMATION: Synthetic Construct

<400> SEQUENCE: 205
gatggagtcg ggaaggaagt cctgtgcgag                                    30

<210> SEQ ID NO 206
<211> LENGTH: 25
<212> TYPE: DNA
<213> ORGANISM: Artificial Sequence
<220> FEATURE:
<223> OTHER INFORMATION: Synthetic Construct

<400> SEQUENCE: 206
gggaagacsg atgggccctt ggtgg                                         25

<210> SEQ ID NO 207
<211> LENGTH: 27
<212> TYPE: DNA
<213> ORGANISM: Artificial Sequence
<220> FEATURE:
<223> OTHER INFORMATION: Synthetic Construct

<400> SEQUENCE: 207
caggcakgcg aygaccacgt tcccatc                                       27

<210> SEQ ID NO 208
<211> LENGTH: 20
<212> TYPE: DNA
<213> ORGANISM: Artificial Sequence
<220> FEATURE:
<223> OTHER INFORMATION: Synthetic Construct

<400> SEQUENCE: 208
ccacagggct gttatccttt                                               20

<210> SEQ ID NO 209
<211> LENGTH: 20
<212> TYPE: DNA
<213> ORGANISM: Artificial Sequence
<220> FEATURE:
<223> OTHER INFORMATION: Synthetic Construct

<400> SEQUENCE: 209
```

```
agggaatgtt tttgcagcag                                              20

<210> SEQ ID NO 210
<211> LENGTH: 34
<212> TYPE: DNA
<213> ORGANISM: Artificial Sequence
<220> FEATURE:
<223> OTHER INFORMATION: Synthetic Construct

<400> SEQUENCE: 210
catcagatgg cgggaagatg aagacagatg gtgc                              34

<210> SEQ ID NO 211
<211> LENGTH: 28
<212> TYPE: DNA
<213> ORGANISM: Artificial Sequence
<220> FEATURE:
<223> OTHER INFORMATION: Synthetic Construct

<400> SEQUENCE: 211
cctcagagga gggtgggaac agagtgac                                     28

<210> SEQ ID NO 212
<211> LENGTH: 31
<212> TYPE: DNA
<213> ORGANISM: Artificial Sequence
<220> FEATURE:
<223> OTHER INFORMATION: Synthetic Construct

<400> SEQUENCE: 212
gctcaaacac agcgacctcg ggtgggaaca c                                 31

<210> SEQ ID NO 213
<211> LENGTH: 30
<212> TYPE: DNA
<213> ORGANISM: Artificial Sequence
<220> FEATURE:
<223> OTHER INFORMATION: Synthetic Construct

<400> SEQUENCE: 213
tctctcagct ggtacacggc agggtcaggg                                   30

<210> SEQ ID NO 214
<211> LENGTH: 12
<212> TYPE: PRT
<213> ORGANISM: Artificial Sequence
<220> FEATURE:
<223> OTHER INFORMATION: Synthetic Construct

<400> SEQUENCE: 214

Cys Ala Gly Gly Gly Ser Gln Gly Asn Leu Ile Phe
1               5                   10

<210> SEQ ID NO 215
<211> LENGTH: 7
<212> TYPE: PRT
<213> ORGANISM: Artificial Sequence
<220> FEATURE:
<223> OTHER INFORMATION: Synthetic Construct

<400> SEQUENCE: 215

Trp Pro Thr Gly Met Arg Phe
1               5

<210> SEQ ID NO 216
```

```
<211> LENGTH: 14
<212> TYPE: PRT
<213> ORGANISM: Artificial Sequence
<220> FEATURE:
<223> OTHER INFORMATION: Synthetic Construct

<400> SEQUENCE: 216

Cys Ala Phe Met Thr Pro Asp Ser Asn Tyr Gln Leu Ile Trp
1               5                   10

<210> SEQ ID NO 217
<211> LENGTH: 16
<212> TYPE: PRT
<213> ORGANISM: Artificial Sequence
<220> FEATURE:
<223> OTHER INFORMATION: Synthetic Construct

<400> SEQUENCE: 217

Cys Ala Val Gly Gly Tyr Ser Gly Gly Gly Ala Asp Gly Leu Thr Phe
1               5                   10                  15

<210> SEQ ID NO 218
<211> LENGTH: 13
<212> TYPE: PRT
<213> ORGANISM: Artificial Sequence
<220> FEATURE:
<223> OTHER INFORMATION: Synthetic Construct

<400> SEQUENCE: 218

Cys Ala Gly Ser Gly Ala Gly Ser Tyr Gln Leu Thr Phe
1               5                   10

<210> SEQ ID NO 219
<211> LENGTH: 12
<212> TYPE: PRT
<213> ORGANISM: Artificial Sequence
<220> FEATURE:
<223> OTHER INFORMATION: Synthetic Construct

<400> SEQUENCE: 219

Cys Ala Val Ser Thr Asn Ala Gly Lys Ser Thr Phe
1               5                   10

<210> SEQ ID NO 220
<211> LENGTH: 15
<212> TYPE: PRT
<213> ORGANISM: Artificial Sequence
<220> FEATURE:
<223> OTHER INFORMATION: Synthetic Construct

<400> SEQUENCE: 220

Cys Ala Ala Lys Gly Arg Gly Ser Thr Lys Gly Arg Leu Tyr Phe
1               5                   10                  15

<210> SEQ ID NO 221
<211> LENGTH: 12
<212> TYPE: PRT
<213> ORGANISM: Artificial Sequence
<220> FEATURE:
<223> OTHER INFORMATION: Synthetic Construct

<400> SEQUENCE: 221

Cys Ala Gly Gly Gly Ser Gln Gly Asn Leu Ile Phe
1               5                   10

<210> SEQ ID NO 222
<211> LENGTH: 14
```

```
<212> TYPE: PRT
<213> ORGANISM: Artificial Sequence
<220> FEATURE:
<223> OTHER INFORMATION: Synthetic Construct

<400> SEQUENCE: 222

Cys Ile Val Arg Val Val Glu Tyr Gly Asn Lys Leu Val Phe
1               5                   10

<210> SEQ ID NO 223
<211> LENGTH: 15
<212> TYPE: PRT
<213> ORGANISM: Artificial Sequence
<220> FEATURE:
<223> OTHER INFORMATION: Synthetic Construct

<400> SEQUENCE: 223

Cys Ala Glu Ser Glu Asp Ser Gly Gly Tyr Asn Lys Leu Ile Phe
1               5                   10                  15

<210> SEQ ID NO 224
<211> LENGTH: 13
<212> TYPE: PRT
<213> ORGANISM: Artificial Sequence
<220> FEATURE:
<223> OTHER INFORMATION: Synthetic Construct

<400> SEQUENCE: 224

Cys Ala Ser Ser Ile Arg Ser Ser Tyr Glu Gln Tyr Phe
1               5                   10

<210> SEQ ID NO 225
<211> LENGTH: 13
<212> TYPE: PRT
<213> ORGANISM: Artificial Sequence
<220> FEATURE:
<223> OTHER INFORMATION: Synthetic Construct

<400> SEQUENCE: 225

Cys Ala Ser Ser Leu Leu Ser Tyr Asn Glu Gln Phe Phe
1               5                   10

<210> SEQ ID NO 226
<211> LENGTH: 18
<212> TYPE: PRT
<213> ORGANISM: Artificial Sequence
<220> FEATURE:
<223> OTHER INFORMATION: Synthetic Construct

<400> SEQUENCE: 226

Cys Ser Ala Pro Arg Thr Ser Gly Gly Leu Leu Asn Pro Tyr Glu Gln
1               5                   10                  15

Tyr Phe

<210> SEQ ID NO 227
<211> LENGTH: 19
<212> TYPE: PRT
<213> ORGANISM: Artificial Sequence
<220> FEATURE:
<223> OTHER INFORMATION: Synthetic Construct

<400> SEQUENCE: 227

Cys Ala Ser Ser Ser Gln Glu Ala Gly Gly Arg Tyr Asn Ser Tyr Glu
1               5                   10                  15

Gln Tyr Phe
```

<210> SEQ ID NO 228
<211> LENGTH: 15
<212> TYPE: PRT
<213> ORGANISM: Artificial Sequence
<220> FEATURE:
<223> OTHER INFORMATION: Synthetic Construct

<400> SEQUENCE: 228

Cys Ala Ser Ser Leu Lys Arg Asp Gly Gln Glu Thr Gln Tyr Phe
1               5                   10                  15

<210> SEQ ID NO 229
<211> LENGTH: 16
<212> TYPE: PRT
<213> ORGANISM: Artificial Sequence
<220> FEATURE:
<223> OTHER INFORMATION: Synthetic Construct

<400> SEQUENCE: 229

Cys Ala Ser Ser Leu Glu Gly Gln Ala Ser Ser Tyr Glu Gln Tyr Phe
1               5                   10                  15

<210> SEQ ID NO 230
<211> LENGTH: 12
<212> TYPE: PRT
<213> ORGANISM: Artificial Sequence
<220> FEATURE:
<223> OTHER INFORMATION: Synthetic Construct

<400> SEQUENCE: 230

Cys Ala Ser Ser Leu Gly Thr Asp Thr Gln Tyr Phe
1               5                   10

<210> SEQ ID NO 231
<211> LENGTH: 14
<212> TYPE: PRT
<213> ORGANISM: Artificial Sequence
<220> FEATURE:
<223> OTHER INFORMATION: Synthetic Construct

<400> SEQUENCE: 231

Cys Ala Ser Ser Leu Gly Val Gly Thr Gly Glu Leu Phe Phe
1               5                   10

<210> SEQ ID NO 232
<211> LENGTH: 19
<212> TYPE: PRT
<213> ORGANISM: Artificial Sequence
<220> FEATURE:
<223> OTHER INFORMATION: Synthetic Construct

<400> SEQUENCE: 232

Cys Ala Ser Ser Ser Glu Ile Gly Thr Ala Gly Thr Ser His Asn Arg
1               5                   10                  15

Gln Tyr Phe

<210> SEQ ID NO 233
<211> LENGTH: 13
<212> TYPE: PRT
<213> ORGANISM: Artificial Sequence
<220> FEATURE:
<223> OTHER INFORMATION: Synthetic Construct

<400> SEQUENCE: 233

Cys Ala Ser Ser Val Arg Ser Ser Tyr Glu Gln Tyr Phe
1               5                   10

<210> SEQ ID NO 234
<211> LENGTH: 14
<212> TYPE: PRT
<213> ORGANISM: Artificial Sequence
<220> FEATURE:
<223> OTHER INFORMATION: Synthetic Construct

<400> SEQUENCE: 234

Cys Ala Leu Trp Glu Val Pro His Tyr Tyr Lys Lys Leu Phe
1               5                   10

<210> SEQ ID NO 235
<211> LENGTH: 12
<212> TYPE: PRT
<213> ORGANISM: Artificial Sequence
<220> FEATURE:
<223> OTHER INFORMATION: Synthetic Construct

<400> SEQUENCE: 235

Cys Ala Asp Gln Pro Gln Ala Tyr Lys Lys Leu Phe
1               5                   10

<210> SEQ ID NO 236
<211> LENGTH: 13
<212> TYPE: PRT
<213> ORGANISM: Artificial Sequence
<220> FEATURE:
<223> OTHER INFORMATION: Synthetic Construct

<400> SEQUENCE: 236

Cys Ala Leu Trp Asp Glu Thr Gly Trp Phe Lys Ile Phe
1               5                   10

<210> SEQ ID NO 237
<211> LENGTH: 17
<212> TYPE: PRT
<213> ORGANISM: Artificial Sequence
<220> FEATURE:
<223> OTHER INFORMATION: Synthetic Construct

<400> SEQUENCE: 237

Cys Ala Cys Trp Ile Arg His Val Arg Ala Thr Gly Trp Phe Lys Ile
1               5                   10                  15

Phe

<210> SEQ ID NO 238
<211> LENGTH: 11
<212> TYPE: PRT
<213> ORGANISM: Artificial Sequence
<220> FEATURE:
<223> OTHER INFORMATION: Synthetic Construct

<400> SEQUENCE: 238

Cys Ala Thr Trp Asp Arg Pro Glu Lys Leu Phe
1               5                   10

<210> SEQ ID NO 239
<211> LENGTH: 13
<212> TYPE: PRT
<213> ORGANISM: Artificial Sequence
<220> FEATURE:
<223> OTHER INFORMATION: Synthetic Construct

<400> SEQUENCE: 239

Cys Ala Thr Trp Asp Asn Pro Tyr Tyr Lys Lys Leu Phe

```
<210> SEQ ID NO 240
<211> LENGTH: 13
<212> TYPE: PRT
<213> ORGANISM: Artificial Sequence
<220> FEATURE:
<223> OTHER INFORMATION: Synthetic Construct

<400> SEQUENCE: 240

Cys Ala Thr Trp Asp Ser Leu Tyr Tyr Lys Lys Leu Phe
1               5                   10

<210> SEQ ID NO 241
<211> LENGTH: 19
<212> TYPE: PRT
<213> ORGANISM: Artificial Sequence
<220> FEATURE:
<223> OTHER INFORMATION: Synthetic Construct

<400> SEQUENCE: 241

Cys Ala Leu Trp Glu Val Leu Thr Leu Ser Arg Thr Thr Gly Trp Phe
1               5                   10                  15

Lys Ile Phe

<210> SEQ ID NO 242
<211> LENGTH: 12
<212> TYPE: PRT
<213> ORGANISM: Artificial Sequence
<220> FEATURE:
<223> OTHER INFORMATION: Synthetic Construct

<400> SEQUENCE: 242

Cys Ala Ala His Thr Thr Gly Trp Phe Lys Ile Phe
1               5                   10

<210> SEQ ID NO 243
<211> LENGTH: 11
<212> TYPE: PRT
<213> ORGANISM: Artificial Sequence
<220> FEATURE:
<223> OTHER INFORMATION: Synthetic Construct

<400> SEQUENCE: 243

Cys Ala Thr Cys Leu Tyr Tyr Lys Lys Leu Phe
1               5                   10

<210> SEQ ID NO 244
<211> LENGTH: 12
<212> TYPE: PRT
<213> ORGANISM: Artificial Sequence
<220> FEATURE:
<223> OTHER INFORMATION: Synthetic Construct

<400> SEQUENCE: 244

Cys Ala Gly Gly Gly Ser Gln Gly Asn Leu Ile Phe
1               5                   10

<210> SEQ ID NO 245
<211> LENGTH: 7
<212> TYPE: PRT
<213> ORGANISM: Artificial Sequence
<220> FEATURE:
<223> OTHER INFORMATION: Synthetic Construct

<400> SEQUENCE: 245
```

```
Trp Pro Thr Gly Met Arg Phe
1               5
```

<210> SEQ ID NO 246
<211> LENGTH: 14
<212> TYPE: PRT
<213> ORGANISM: Artificial Sequence
<220> FEATURE:
<223> OTHER INFORMATION: Synthetic Construct

<400> SEQUENCE: 246

```
Cys Ala Phe Met Thr Pro Asp Ser Asn Tyr Gln Leu Ile Trp
1               5                   10
```

<210> SEQ ID NO 247
<211> LENGTH: 16
<212> TYPE: PRT
<213> ORGANISM: Artificial Sequence
<220> FEATURE:
<223> OTHER INFORMATION: Synthetic Construct

<400> SEQUENCE: 247

```
Cys Ala Val Gly Gly Tyr Ser Gly Gly Gly Ala Asp Gly Leu Thr Phe
1               5                   10                  15
```

<210> SEQ ID NO 248
<211> LENGTH: 13
<212> TYPE: PRT
<213> ORGANISM: Artificial Sequence
<220> FEATURE:
<223> OTHER INFORMATION: Synthetic Construct

<400> SEQUENCE: 248

```
Cys Ala Gly Ser Gly Ala Gly Ser Tyr Gln Leu Thr Phe
1               5                   10
```

<210> SEQ ID NO 249
<211> LENGTH: 15
<212> TYPE: PRT
<213> ORGANISM: Artificial Sequence
<220> FEATURE:
<223> OTHER INFORMATION: Synthetic Construct

<400> SEQUENCE: 249

```
Cys Ala Ala Lys Gly Arg Gly Ser Thr Leu Gly Arg Leu Tyr Phe
1               5                   10                  15
```

<210> SEQ ID NO 250
<211> LENGTH: 11
<212> TYPE: PRT
<213> ORGANISM: Artificial Sequence
<220> FEATURE:
<223> OTHER INFORMATION: Synthetic Construct

<400> SEQUENCE: 250

```
Cys Ala Gly Gly Gly Gln Gly Asn Leu Ile Phe
1               5                   10
```

<210> SEQ ID NO 251
<211> LENGTH: 12
<212> TYPE: PRT
<213> ORGANISM: Artificial Sequence
<220> FEATURE:
<223> OTHER INFORMATION: Synthetic Construct

<400> SEQUENCE: 251

```
Cys Ala Val Ser Thr Asn Ala Phe Lys Ser Thr Phe
```

```
1               5                   10
```

<210> SEQ ID NO 252
<211> LENGTH: 14
<212> TYPE: PRT
<213> ORGANISM: Artificial Sequence
<220> FEATURE:
<223> OTHER INFORMATION: Synthetic Construct

<400> SEQUENCE: 252

```
Cys Ile Val Arg Val Val Glu Tyr Gly Asn Lys Leu Val Phe
1               5                   10
```

<210> SEQ ID NO 253
<211> LENGTH: 14
<212> TYPE: PRT
<213> ORGANISM: Artificial Sequence
<220> FEATURE:
<223> OTHER INFORMATION: Synthetic Construct

<400> SEQUENCE: 253

```
Cys Ala Glu Met Ala Pro Gly Gly Tyr Gln Lys Val Thr Phe
1               5                   10
```

<210> SEQ ID NO 254
<211> LENGTH: 13
<212> TYPE: PRT
<213> ORGANISM: Artificial Sequence
<220> FEATURE:
<223> OTHER INFORMATION: Synthetic Construct

<400> SEQUENCE: 254

```
Cys Ala Ser Ser Ile Arg Ser Ser Tyr Glu Gln Tyr Phe
1               5                   10
```

<210> SEQ ID NO 255
<211> LENGTH: 13
<212> TYPE: PRT
<213> ORGANISM: Artificial Sequence
<220> FEATURE:
<223> OTHER INFORMATION: Synthetic Construct

<400> SEQUENCE: 255

```
Cys Ala Ser Ser Leu Leu Ser Tyr Asn Glu Gln Phe Phe
1               5                   10
```

<210> SEQ ID NO 256
<211> LENGTH: 18
<212> TYPE: PRT
<213> ORGANISM: Artificial Sequence
<220> FEATURE:
<223> OTHER INFORMATION: Synthetic Construct

<400> SEQUENCE: 256

```
Cys Ser Ala Pro Arg Thr Ser Phe Phe Leu Leu Asn Pro Tyr Glu Gln
1               5                   10                  15

Tyr Phe
```

<210> SEQ ID NO 257
<211> LENGTH: 16
<212> TYPE: PRT
<213> ORGANISM: Artificial Sequence
<220> FEATURE:
<223> OTHER INFORMATION: Synthetic Construct

<400> SEQUENCE: 257

Cys Ala Ser Ser Leu Glu Gly Gln Ala Ser Ser Tyr Glu Gln Tyr Phe
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Synthetic Construct

<400> SEQUENCE: 258

Cys Ala Ser Ser Leu Lys Arg Asp Gly Gln Glu Thr Gln Tyr Phe
1               5                   10                  15

<210> SEQ ID NO 259
<211> LENGTH: 18
<212> TYPE: PRT
<213> ORGANISM: Artificial Sequence
<220> FEATURE:
<223> OTHER INFORMATION: Synthetic Construct

<400> SEQUENCE: 259

Cys Ala Ser Ser Trp Glu Ala Gly Gly Arg Tyr Asn Ser Tyr Glu Gln
1               5                   10                  15

Tyr Phe

<210> SEQ ID NO 260
<211> LENGTH: 14
<212> TYPE: PRT
<213> ORGANISM: Artificial Sequence
<220> FEATURE:
<223> OTHER INFORMATION: Synthetic Construct

<400> SEQUENCE: 260

Cys Ala Ser Ser Leu Gly Val Gly Thr Gly Glu Leu Phe Phe
1               5                   10

<210> SEQ ID NO 261
<211> LENGTH: 12
<212> TYPE: PRT
<213> ORGANISM: Artificial Sequence
<220> FEATURE:
<223> OTHER INFORMATION: Synthetic Construct

<400> SEQUENCE: 261

Cys Ala Ser Ser Leu Gly Thr Asp Thr Gln Tyr Phe
1               5                   10

<210> SEQ ID NO 262
<211> LENGTH: 12
<212> TYPE: PRT
<213> ORGANISM: Artificial Sequence
<220> FEATURE:
<223> OTHER INFORMATION: Synthetic Construct

<400> SEQUENCE: 262

Cys Ala Ser Ser Leu Asp Arg Asn Glu Gln Tyr Phe
1               5                   10

<210> SEQ ID NO 263
<211> LENGTH: 13
<212> TYPE: PRT
<213> ORGANISM: Artificial Sequence
<220> FEATURE:
<223> OTHER INFORMATION: Synthetic Construct

<400> SEQUENCE: 263

Cys Ala Ser Ser Val Arg Ser Ser Tyr Glu Gln Tyr Phe
1               5                   10

<210> SEQ ID NO 264
<211> LENGTH: 14
<212> TYPE: PRT
<213> ORGANISM: Artificial Sequence
<220> FEATURE:
<223> OTHER INFORMATION: Synthetic Construct

<400> SEQUENCE: 264

Cys Ala Leu Trp Glu Val Pro His Tyr Tyr Lys Lys Leu Phe
1               5                   10

<210> SEQ ID NO 265
<211> LENGTH: 12
<212> TYPE: PRT
<213> ORGANISM: Artificial Sequence
<220> FEATURE:
<223> OTHER INFORMATION: Synthetic Construct

<400> SEQUENCE: 265

Cys Ala Asp Gln Pro Gln Ala Tyr Lys Lys Leu Phe
1               5                   10

<210> SEQ ID NO 266
<211> LENGTH: 13
<212> TYPE: PRT
<213> ORGANISM: Artificial Sequence
<220> FEATURE:
<223> OTHER INFORMATION: Synthetic Construct

<400> SEQUENCE: 266

Cys Ala Leu Trp Asp Glu Thr Gly Trp Phe Lys Ile Phe
1               5                   10

<210> SEQ ID NO 267
<211> LENGTH: 17
<212> TYPE: PRT
<213> ORGANISM: Artificial Sequence
<220> FEATURE:
<223> OTHER INFORMATION: Synthetic Construct

<400> SEQUENCE: 267

Cys Ala Cys Trp Ile Arg His Val Arg Ala Thr Gly Trp Phe Lys Ile
1               5                   10                  15

Phe

<210> SEQ ID NO 268
<211> LENGTH: 11
<212> TYPE: PRT
<213> ORGANISM: Artificial Sequence
<220> FEATURE:
<223> OTHER INFORMATION: Synthetic Construct

<400> SEQUENCE: 268

Cys Ala Thr Trp Asp Arg Pro Glu Lys Leu Phe
1               5                   10

<210> SEQ ID NO 269
<211> LENGTH: 13
<212> TYPE: PRT
<213> ORGANISM: Artificial Sequence
<220> FEATURE:
<223> OTHER INFORMATION: Synthetic Construct

```
<400> SEQUENCE: 269

Cys Ala Thr Trp Asp Asn Pro Tyr Tyr Lys Lys Leu Phe
1               5                   10

<210> SEQ ID NO 270
<211> LENGTH: 13
<212> TYPE: PRT
<213> ORGANISM: Artificial Sequence
<220> FEATURE:
<223> OTHER INFORMATION: Synthetic Construct

<400> SEQUENCE: 270

Cys Ala Thr Trp Asp Ser Leu Tyr Tyr Lys Lys Leu Phe
1               5                   10

<210> SEQ ID NO 271
<211> LENGTH: 11
<212> TYPE: PRT
<213> ORGANISM: Artificial Sequence
<220> FEATURE:
<223> OTHER INFORMATION: Synthetic Construct

<400> SEQUENCE: 271

Cys Ala Thr Cys Leu Tyr Tyr Lys Lys Leu Phe
1               5                   10

<210> SEQ ID NO 272
<211> LENGTH: 19
<212> TYPE: PRT
<213> ORGANISM: Artificial Sequence
<220> FEATURE:
<223> OTHER INFORMATION: Synthetic Construct

<400> SEQUENCE: 272

Cys Ala Leu Trp Glu Val Leu Thr Leu Ser Arg Thr Thr Gly Trp Phe
1               5                   10                  15

Lys Ile Phe

<210> SEQ ID NO 273
<211> LENGTH: 12
<212> TYPE: PRT
<213> ORGANISM: Artificial Sequence
<220> FEATURE:
<223> OTHER INFORMATION: Synthetic Construct

<400> SEQUENCE: 273

Cys Ala Ala His Thr Thr Gly Trp Phe Lys Ile Phe
1               5                   10

<210> SEQ ID NO 274
<211> LENGTH: 12
<212> TYPE: PRT
<213> ORGANISM: Artificial Sequence
<220> FEATURE:
<223> OTHER INFORMATION: Synthetic Construct

<400> SEQUENCE: 274

Cys Ala Gly Gly Gly Ser Gln Gly Asn Leu Ile Phe
1               5                   10

<210> SEQ ID NO 275
<211> LENGTH: 12
<212> TYPE: PRT
<213> ORGANISM: Artificial Sequence
<220> FEATURE:
<223> OTHER INFORMATION: Synthetic Construct
```

```
<400> SEQUENCE: 275

Cys Ala Val Pro Ser Gly Asn Thr Pro Leu Val Phe
1               5                   10

<210> SEQ ID NO 276
<211> LENGTH: 9
<212> TYPE: PRT
<213> ORGANISM: Artificial Sequence
<220> FEATURE:
<223> OTHER INFORMATION: Synthetic Construct

<400> SEQUENCE: 276

Cys Ala Thr Gly Gly Lys Leu Ile Phe
1               5

<210> SEQ ID NO 277
<211> LENGTH: 13
<212> TYPE: PRT
<213> ORGANISM: Artificial Sequence
<220> FEATURE:
<223> OTHER INFORMATION: Synthetic Construct

<400> SEQUENCE: 277

Cys Ala Gly Ser Gly Ala Gly Ser Tyr Gln Leu Thr Phe
1               5                   10

<210> SEQ ID NO 278
<211> LENGTH: 17
<212> TYPE: PRT
<213> ORGANISM: Artificial Sequence
<220> FEATURE:
<223> OTHER INFORMATION: Synthetic Construct

<400> SEQUENCE: 278

Cys Ala Val Arg Ala Asn Ile Leu Thr Gly Gly Gly Asn Lys Leu Thr
1               5                   10                  15

Phe

<210> SEQ ID NO 279
<211> LENGTH: 13
<212> TYPE: PRT
<213> ORGANISM: Artificial Sequence
<220> FEATURE:
<223> OTHER INFORMATION: Synthetic Construct

<400> SEQUENCE: 279

Cys Ala Ala Ser Thr Ser Asn Asp Tyr Lys Leu Ser Phe
1               5                   10

<210> SEQ ID NO 280
<211> LENGTH: 14
<212> TYPE: PRT
<213> ORGANISM: Artificial Sequence
<220> FEATURE:
<223> OTHER INFORMATION: Synthetic Construct

<400> SEQUENCE: 280

Cys Ala Phe Met Thr Pro Asp Ser Asn Tyr Gln Leu Ile Trp
1               5                   10

<210> SEQ ID NO 281
<211> LENGTH: 12
<212> TYPE: PRT
<213> ORGANISM: Artificial Sequence
<220> FEATURE:
```

```
<223> OTHER INFORMATION: Synthetic Construct

<400> SEQUENCE: 281

Cys Ala Ser Gln Ala Asp Thr Gly Lys Leu Ile Phe
1               5                   10

<210> SEQ ID NO 282
<211> LENGTH: 16
<212> TYPE: PRT
<213> ORGANISM: Artificial Sequence
<220> FEATURE:
<223> OTHER INFORMATION: Synthetic Construct

<400> SEQUENCE: 282

Cys Ala Val Gly Gly Tyr Ser Gly Gly Gly Ala Asp Gly Leu Thr Phe
1               5                   10                  15

<210> SEQ ID NO 283
<211> LENGTH: 14
<212> TYPE: PRT
<213> ORGANISM: Artificial Sequence
<220> FEATURE:
<223> OTHER INFORMATION: Synthetic Construct

<400> SEQUENCE: 283

Cys Ala Val Arg Asp Thr Gly Gly Tyr Gln Lys Val Thr Phe
1               5                   10

<210> SEQ ID NO 284
<211> LENGTH: 13
<212> TYPE: PRT
<213> ORGANISM: Artificial Sequence
<220> FEATURE:
<223> OTHER INFORMATION: Synthetic Construct

<400> SEQUENCE: 284

Cys Ala Val Ser Gly Ala Gly Ser Tyr Gln Leu Thr Phe
1               5                   10

<210> SEQ ID NO 285
<211> LENGTH: 14
<212> TYPE: PRT
<213> ORGANISM: Artificial Sequence
<220> FEATURE:
<223> OTHER INFORMATION: Synthetic Construct

<400> SEQUENCE: 285

Cys Ile Val Arg Val Val Glu Tyr Gly Asn Lys Leu Val Phe
1               5                   10

<210> SEQ ID NO 286
<211> LENGTH: 14
<212> TYPE: PRT
<213> ORGANISM: Artificial Sequence
<220> FEATURE:
<223> OTHER INFORMATION: Synthetic Construct

<400> SEQUENCE: 286

Cys Leu Val Gly Asp Pro Ser Asn Asp Tyr Lys Leu Ser Phe
1               5                   10

<210> SEQ ID NO 287
<211> LENGTH: 13
<212> TYPE: PRT
<213> ORGANISM: Artificial Sequence
<220> FEATURE:
<223> OTHER INFORMATION: Synthetic Construct
```

<400> SEQUENCE: 287

Cys Ala Ser Ser Ile Arg Ser Ser Tyr Glu Gln Tyr Phe
1               5                   10

<210> SEQ ID NO 288
<211> LENGTH: 13
<212> TYPE: PRT
<213> ORGANISM: Artificial Sequence
<220> FEATURE:
<223> OTHER INFORMATION: Synthetic Construct

<400> SEQUENCE: 288

Cys Ala Ser Ser Val Arg Ser Ser Tyr Glu Gln Tyr Phe
1               5                   10

<210> SEQ ID NO 289
<211> LENGTH: 13
<212> TYPE: PRT
<213> ORGANISM: Artificial Sequence
<220> FEATURE:
<223> OTHER INFORMATION: Synthetic Construct

<400> SEQUENCE: 289

Cys Ala Ser Ser Pro Arg Gly Thr Thr Glu Ala Phe Phe
1               5                   10

<210> SEQ ID NO 290
<211> LENGTH: 14
<212> TYPE: PRT
<213> ORGANISM: Artificial Sequence
<220> FEATURE:
<223> OTHER INFORMATION: Synthetic Construct

<400> SEQUENCE: 290

Cys Ala Ser Ser Phe Ser Gly Arg Gly Tyr Gly Tyr Thr Phe
1               5                   10

<210> SEQ ID NO 291
<211> LENGTH: 13
<212> TYPE: PRT
<213> ORGANISM: Artificial Sequence
<220> FEATURE:
<223> OTHER INFORMATION: Synthetic Construct

<400> SEQUENCE: 291

Cys Ala Ser Ser His Gly Thr Phe Tyr Glu Gln Tyr Phe
1               5                   10

<210> SEQ ID NO 292
<211> LENGTH: 13
<212> TYPE: PRT
<213> ORGANISM: Artificial Sequence
<220> FEATURE:
<223> OTHER INFORMATION: Synthetic Construct

<400> SEQUENCE: 292

Cys Ala Ser Ser Leu Leu Ser Tyr Asn Glu Gln Phe Phe
1               5                   10

<210> SEQ ID NO 293
<211> LENGTH: 12
<212> TYPE: PRT
<213> ORGANISM: Artificial Sequence
<220> FEATURE:
<223> OTHER INFORMATION: Synthetic Construct

<400> SEQUENCE: 293

Cys Ala Gly Gly Gly Ser Gln Gly Asn Leu Ile Phe
1               5                   10

<210> SEQ ID NO 294
<211> LENGTH: 12
<212> TYPE: PRT
<213> ORGANISM: Artificial Sequence
<220> FEATURE:
<223> OTHER INFORMATION: Synthetic Construct

<400> SEQUENCE: 294

Cys Ala Val Pro Ser Gly Asn Thr Pro Leu Val Phe
1               5                   10

<210> SEQ ID NO 295
<211> LENGTH: 9
<212> TYPE: PRT
<213> ORGANISM: Artificial Sequence
<220> FEATURE:
<223> OTHER INFORMATION: Synthetic Construct

<400> SEQUENCE: 295

Cys Ala Thr Gly Gly Lys Leu Ile Phe
1               5

<210> SEQ ID NO 296
<211> LENGTH: 13
<212> TYPE: PRT
<213> ORGANISM: Artificial Sequence
<220> FEATURE:
<223> OTHER INFORMATION: Synthetic Construct

<400> SEQUENCE: 296

Cys Ala Gly Ser Gly Ala Gly Ser Tyr Gln Leu Thr Phe
1               5                   10

<210> SEQ ID NO 297
<211> LENGTH: 15
<212> TYPE: PRT
<213> ORGANISM: Artificial Sequence
<220> FEATURE:
<223> OTHER INFORMATION: Synthetic Construct

<400> SEQUENCE: 297

Cys Ala Glu Ser Glu Asp Ser Gly Gly Tyr Asn Lys Leu Ile Phe
1               5                   10                  15

<210> SEQ ID NO 298
<211> LENGTH: 12
<212> TYPE: PRT
<213> ORGANISM: Artificial Sequence
<220> FEATURE:
<223> OTHER INFORMATION: Synthetic Construct

<400> SEQUENCE: 298

Cys Ala Gly Trp Ala Gly Asn Thr Pro Leu Val Phe
1               5                   10

<210> SEQ ID NO 299
<211> LENGTH: 14
<212> TYPE: PRT
<213> ORGANISM: Artificial Sequence
<220> FEATURE:
<223> OTHER INFORMATION: Synthetic Construct

<400> SEQUENCE: 299

Cys Leu Val Gly Asp Pro Ser Asn Asp Tyr Lys Leu Ser Phe
1               5                   10

<210> SEQ ID NO 300
<211> LENGTH: 13
<212> TYPE: PRT
<213> ORGANISM: Artificial Sequence
<220> FEATURE:
<223> OTHER INFORMATION: Synthetic Construct

<400> SEQUENCE: 300

Cys Ala Ser Ser Ile Arg Ser Ser Tyr Glu Gln Tyr Phe
1               5                   10

<210> SEQ ID NO 301
<211> LENGTH: 13
<212> TYPE: PRT
<213> ORGANISM: Artificial Sequence
<220> FEATURE:
<223> OTHER INFORMATION: Synthetic Construct

<400> SEQUENCE: 301

Cys Ala Ser Ser Val Arg Ser Ser Tyr Glu Gln Tyr Phe
1               5                   10

<210> SEQ ID NO 302
<211> LENGTH: 14
<212> TYPE: PRT
<213> ORGANISM: Artificial Sequence
<220> FEATURE:
<223> OTHER INFORMATION: Synthetic Construct

<400> SEQUENCE: 302

Cys Ala Ser Ser Phe Ser Gly Arg Gly Tyr Gly Tyr Thr Phe
1               5                   10

<210> SEQ ID NO 303
<211> LENGTH: 13
<212> TYPE: PRT
<213> ORGANISM: Artificial Sequence
<220> FEATURE:
<223> OTHER INFORMATION: Synthetic Construct

<400> SEQUENCE: 303

Cys Ala Ser Ser Ile Arg Ser Ser Tyr Glu Gln Tyr Phe
1               5                   10

<210> SEQ ID NO 304
<211> LENGTH: 16
<212> TYPE: PRT
<213> ORGANISM: Artificial Sequence
<220> FEATURE:
<223> OTHER INFORMATION: Synthetic Construct

<400> SEQUENCE: 304

Cys Ala Ser Ser Leu Glu Gly Gln Ala Ser Ser Tyr Glu Gln Tyr Phe
1               5                   10                  15

<210> SEQ ID NO 305
<211> LENGTH: 13
<212> TYPE: PRT
<213> ORGANISM: Artificial Sequence
<220> FEATURE:
<223> OTHER INFORMATION: Synthetic Construct

<400> SEQUENCE: 305

Cys Ala Ser Ser Leu Leu Ser Tyr Asn Glu Gln Phe Phe
1               5                   10

<210> SEQ ID NO 306
<211> LENGTH: 12
<212> TYPE: PRT
<213> ORGANISM: Artificial Sequence
<220> FEATURE:
<223> OTHER INFORMATION: Synthetic Construct

<400> SEQUENCE: 306

Cys Ala Gly Gly Gly Ser Gln Gly Asn Leu Ile Phe
1               5                   10

<210> SEQ ID NO 307
<211> LENGTH: 12
<212> TYPE: PRT
<213> ORGANISM: Artificial Sequence
<220> FEATURE:
<223> OTHER INFORMATION: Synthetic Construct

<400> SEQUENCE: 307

Cys Ala Glu Asp Ser Ser Ala Ser Lys Ile Ile Phe
1               5                   10

<210> SEQ ID NO 308
<211> LENGTH: 12
<212> TYPE: PRT
<213> ORGANISM: Artificial Sequence
<220> FEATURE:
<223> OTHER INFORMATION: Synthetic Construct

<400> SEQUENCE: 308

Cys Ala Arg Gly Gly Ser Gln Gly Asn Leu Ile Phe
1               5                   10

<210> SEQ ID NO 309
<211> LENGTH: 13
<212> TYPE: PRT
<213> ORGANISM: Artificial Sequence
<220> FEATURE:
<223> OTHER INFORMATION: Synthetic Construct

<400> SEQUENCE: 309

Cys Ala Ser Ser Ile Arg Ser Ser Tyr Glu Gln Tyr Phe
1               5                   10

<210> SEQ ID NO 310
<211> LENGTH: 13
<212> TYPE: PRT
<213> ORGANISM: Artificial Sequence
<220> FEATURE:
<223> OTHER INFORMATION: Synthetic Construct

<400> SEQUENCE: 310

Cys Ala Ser Ser Val Arg Ser Ser Tyr Glu Gln Tyr Phe
1               5                   10

<210> SEQ ID NO 311
<211> LENGTH: 14
<212> TYPE: PRT
<213> ORGANISM: Artificial Sequence
<220> FEATURE:
<223> OTHER INFORMATION: Synthetic Construct

<400> SEQUENCE: 311

Cys Ala Cys Trp Ser Gly Leu Gly Asn Gln Pro Gln His Phe

```
1               5                   10
```

<210> SEQ ID NO 312
<211> LENGTH: 12
<212> TYPE: PRT
<213> ORGANISM: Artificial Sequence
<220> FEATURE:
<223> OTHER INFORMATION: Synthetic Construct

<400> SEQUENCE: 312

```
Cys Ala Gly Gly Gly Ser Gln Gly Asn Leu Ile Phe
1               5                   10
```

<210> SEQ ID NO 313
<211> LENGTH: 13
<212> TYPE: PRT
<213> ORGANISM: Artificial Sequence
<220> FEATURE:
<223> OTHER INFORMATION: Synthetic Construct

<400> SEQUENCE: 313

```
Cys Ala Ser Ser Ile Arg Ser Ser Tyr Glu Gln Tyr Phe
1               5                   10
```

<210> SEQ ID NO 314
<211> LENGTH: 12
<212> TYPE: PRT
<213> ORGANISM: Artificial Sequence
<220> FEATURE:
<223> OTHER INFORMATION: Synthetic Construct

<400> SEQUENCE: 314

```
Cys Ala Gly Gly Gly Ser Gln Gly Asn Leu Ile Phe
1               5                   10
```

<210> SEQ ID NO 315
<211> LENGTH: 15
<212> TYPE: PRT
<213> ORGANISM: Artificial Sequence
<220> FEATURE:
<223> OTHER INFORMATION: Synthetic Construct

<400> SEQUENCE: 315

```
Cys Ala Glu Ser Glu Asp Ser Gly Gly Tyr Asn Lys Leu Ile Phe
1               5                   10                  15
```

<210> SEQ ID NO 316
<211> LENGTH: 13
<212> TYPE: PRT
<213> ORGANISM: Artificial Sequence
<220> FEATURE:
<223> OTHER INFORMATION: Synthetic Construct

<400> SEQUENCE: 316

```
Cys Ala Ser Ser Ile Arg Ser Ser Tyr Glu Gln Tyr Phe
1               5                   10
```

<210> SEQ ID NO 317
<211> LENGTH: 13
<212> TYPE: PRT
<213> ORGANISM: Artificial Sequence
<220> FEATURE:
<223> OTHER INFORMATION: Synthetic Construct

<400> SEQUENCE: 317

```
Cys Ala Ser Ser Val Arg Ser Ser Tyr Glu Gln Tyr Phe
1               5                   10
```

<210> SEQ ID NO 318
<211> LENGTH: 14
<212> TYPE: PRT
<213> ORGANISM: Artificial Sequence
<220> FEATURE:
<223> OTHER INFORMATION: Synthetic Construct

<400> SEQUENCE: 318

Cys Ala Thr Ser Arg Gly Ser Pro Asn Tyr Gly Tyr Thr Phe
1               5                   10

<210> SEQ ID NO 319
<211> LENGTH: 19
<212> TYPE: PRT
<213> ORGANISM: Artificial Sequence
<220> FEATURE:
<223> OTHER INFORMATION: Synthetic Construct

<400> SEQUENCE: 319

Cys Ala Ser Ser Pro Gly Thr Ser Gly Ser Ala Ser Thr Asp Thr
1               5                   10                  15

Gln Tyr Phe

<210> SEQ ID NO 320
<211> LENGTH: 18
<212> TYPE: PRT
<213> ORGANISM: Artificial Sequence
<220> FEATURE:
<223> OTHER INFORMATION: Synthetic Construct

<400> SEQUENCE: 320

Cys Ala Ser Ser Leu Ala Leu Ile Val Gly Gly Glu Asn Thr Glu Ala
1               5                   10                  15

Phe Phe

<210> SEQ ID NO 321
<211> LENGTH: 18
<212> TYPE: PRT
<213> ORGANISM: Artificial Sequence
<220> FEATURE:
<223> OTHER INFORMATION: Synthetic Construct

<400> SEQUENCE: 321

Cys Ala Ser Ser Lys Gly Gly Thr Gly Gly Trp Ala Gly Glu Leu
1               5                   10                  15

Phe Phe

<210> SEQ ID NO 322
<211> LENGTH: 18
<212> TYPE: PRT
<213> ORGANISM: Artificial Sequence
<220> FEATURE:
<223> OTHER INFORMATION: Synthetic Construct

<400> SEQUENCE: 322

Cys Ala Ser Ser Gln Ala Phe Leu Pro Ser Leu Val Thr Asp Thr Gln
1               5                   10                  15

Tyr Phe

<210> SEQ ID NO 323
<211> LENGTH: 17
<212> TYPE: PRT
<213> ORGANISM: Artificial Sequence

```
<220> FEATURE:
<223> OTHER INFORMATION: Synthetic Construct

<400> SEQUENCE: 323

Cys Ala Ser Ser Ala Asp Thr Gly Thr Phe Met Asn Thr Glu Ala Phe
1               5                   10                  15

Phe

<210> SEQ ID NO 324
<211> LENGTH: 17
<212> TYPE: PRT
<213> ORGANISM: Artificial Sequence
<220> FEATURE:
<223> OTHER INFORMATION: Synthetic Construct

<400> SEQUENCE: 324

Cys Ala Ser Ser Leu Gly Glu Arg Gly Ala Leu Ser Glu Thr Gln Tyr
1               5                   10                  15

Phe

<210> SEQ ID NO 325
<211> LENGTH: 17
<212> TYPE: PRT
<213> ORGANISM: Artificial Sequence
<220> FEATURE:
<223> OTHER INFORMATION: Synthetic Construct

<400> SEQUENCE: 325

Cys Ala Ser Ser Phe Ser Lys Asn Ser Arg Pro Tyr Asn Glu Gln Gly
1               5                   10                  15

Gly

<210> SEQ ID NO 326
<211> LENGTH: 17
<212> TYPE: PRT
<213> ORGANISM: Artificial Sequence
<220> FEATURE:
<223> OTHER INFORMATION: Synthetic Construct

<400> SEQUENCE: 326

Cys Ala Ser Ser Leu Gly Ser Arg Gly Gln Arg Leu Leu Glu Gln Tyr
1               5                   10                  15

Phe

<210> SEQ ID NO 327
<211> LENGTH: 18
<212> TYPE: PRT
<213> ORGANISM: Artificial Sequence
<220> FEATURE:
<223> OTHER INFORMATION: Synthetic Construct

<400> SEQUENCE: 327

Cys Ala Ser Ser Leu Val Ala Gly Gly Phe Ser Tyr Asn Glu Gln Phe
1               5                   10                  15

Phe Phe

<210> SEQ ID NO 328
<211> LENGTH: 14
<212> TYPE: PRT
<213> ORGANISM: Artificial Sequence
<220> FEATURE:
<223> OTHER INFORMATION: Synthetic Construct

<400> SEQUENCE: 328
```

Cys Ala Ser Ser Pro Gly Thr Gly Ile Asp Thr Gln Tyr Phe
1               5                   10

<210> SEQ ID NO 329
<211> LENGTH: 13
<212> TYPE: PRT
<213> ORGANISM: Artificial Sequence
<220> FEATURE:
<223> OTHER INFORMATION: Synthetic Construct

<400> SEQUENCE: 329

Cys Ala Ser Ser Arg Gln Gly Asn Ser Pro Leu His Phe
1               5                   10

<210> SEQ ID NO 330
<211> LENGTH: 21
<212> TYPE: PRT
<213> ORGANISM: Artificial Sequence
<220> FEATURE:
<223> OTHER INFORMATION: Synthetic Construct

<400> SEQUENCE: 330

Cys Ala Ser Ser Gln Gly Arg Thr Arg Leu Gln Arg Gly Gly Arg Thr
1               5                   10                  15

Asp Thr Gln Tyr Phe
            20

<210> SEQ ID NO 331
<211> LENGTH: 19
<212> TYPE: PRT
<213> ORGANISM: Artificial Sequence
<220> FEATURE:
<223> OTHER INFORMATION: Synthetic Construct

<400> SEQUENCE: 331

Cys Ala Ser Ser Ile Gly Leu Ala Gly Ala Leu Arg Asp Thr Gly Glu
1               5                   10                  15

Leu Phe Phe

<210> SEQ ID NO 332
<211> LENGTH: 19
<212> TYPE: PRT
<213> ORGANISM: Artificial Sequence
<220> FEATURE:
<223> OTHER INFORMATION: Synthetic Construct

<400> SEQUENCE: 332

Cys Ala Ser Ser Leu Arg Gly Pro Gly Gln Gly Glu Gly Gly Ser Pro
1               5                   10                  15

Leu His Phe

<210> SEQ ID NO 333
<211> LENGTH: 18
<212> TYPE: PRT
<213> ORGANISM: Artificial Sequence
<220> FEATURE:
<223> OTHER INFORMATION: Synthetic Construct

<400> SEQUENCE: 333

Cys Ala Ser Ser Tyr Pro Phe Pro Leu Thr Gly Gly Asn Gln Pro Gln
1               5                   10                  15

His Phe

```
<210> SEQ ID NO 334
<211> LENGTH: 17
<212> TYPE: PRT
<213> ORGANISM: Artificial Sequence
<220> FEATURE:
<223> OTHER INFORMATION: Synthetic Construct

<400> SEQUENCE: 334

Cys Ala Ser Ser Tyr Ala Gly Thr Arg Leu Gly Asn Gln Pro Gln His
1               5                   10                  15

Phe

<210> SEQ ID NO 335
<211> LENGTH: 17
<212> TYPE: PRT
<213> ORGANISM: Artificial Sequence
<220> FEATURE:
<223> OTHER INFORMATION: Synthetic Construct

<400> SEQUENCE: 335

Cys Ala Ser Ser Leu Gly Leu Ala Gly Val Arg Gln Glu Thr Gln Tyr
1               5                   10                  15

Phe

<210> SEQ ID NO 336
<211> LENGTH: 17
<212> TYPE: PRT
<213> ORGANISM: Artificial Sequence
<220> FEATURE:
<223> OTHER INFORMATION: Synthetic Construct

<400> SEQUENCE: 336

Cys Ala Ser Ser Leu Asn Arg Ala Phe Ser Gly Ala Asn Val Leu Thr
1               5                   10                  15

Phe

<210> SEQ ID NO 337
<211> LENGTH: 16
<212> TYPE: PRT
<213> ORGANISM: Artificial Sequence
<220> FEATURE:
<223> OTHER INFORMATION: Synthetic Construct

<400> SEQUENCE: 337

Cys Ala Ser Ser Glu Ala Arg Ser Gly Pro Asp Thr Asp Gln Tyr Phe
1               5                   10                  15
```